(12) United States Patent
Nesspor

(10) Patent No.: US 11,192,951 B2
(45) Date of Patent: Dec. 7, 2021

(54) METHODS OF ENGINEERING SURFACE CHARGE FOR BISPECIFIC ANTIBODY PRODUCTION

(71) Applicant: Janssen Biotech, Inc., Horsham, PA (US)

(72) Inventor: Thomas Nesspor, Collegeville, PA (US)

(73) Assignee: Janseen Biotech, Inc., Horsham, PA (US)

( * ) Notice: Subject to any disclaimer, the term of this patent is extended or adjusted under 35 U.S.C. 154(b) by 0 days.

(21) Appl. No.: 15/997,318

(22) Filed: Jun. 4, 2018

(65) Prior Publication Data

US 2019/0031764 A1     Jan. 31, 2019

Related U.S. Application Data

(60) Provisional application No. 62/515,297, filed on Jun. 5, 2017.

(51) Int. Cl.
*C07K 16/28* (2006.01)
*C07K 16/24* (2006.01)
*C07K 16/06* (2006.01)

(52) U.S. Cl.
CPC ........ *C07K 16/2875* (2013.01); *C07K 16/065* (2013.01); *C07K 16/241* (2013.01); *C07K 16/2803* (2013.01); *C07K 16/2818* (2013.01); *C07K 16/2848* (2013.01); *C07K 2317/31* (2013.01); *C07K 2317/51* (2013.01); *C07K 2317/515* (2013.01); *C07K 2317/567* (2013.01); *C07K 2317/90* (2013.01); *C07K 2317/92* (2013.01); *C07K 2317/94* (2013.01)

(58) Field of Classification Search
CPC ............ C07K 16/2875; C07K 16/2848; C07K 16/2818; C07K 16/241; C07K 16/2803; C07K 2317/92; C07K 2317/567; C07K 2317/94; C07K 2317/31; C07K 2317/90
See application file for complete search history.

(56) References Cited

U.S. PATENT DOCUMENTS

| | | | |
|---|---|---|---|
| 8,188,231 B2 | 5/2012 | Lazar et al. | |
| 8,216,805 B2 | 7/2012 | Carter et al. | |
| 8,802,820 B2 | 8/2014 | Chamberlain et al. | |
| 9,040,041 B2 | 5/2015 | Desjarlais et al. | |
| 2005/0255532 A1 | 11/2005 | Ruben et al. | |
| 2009/0263392 A1 | 10/2009 | Igawa et al. | |
| 2011/0076275 A1 | 3/2011 | Igawa et al. | |
| 2011/0319597 A1 | 12/2011 | Simpson et al. | |
| 2012/0121587 A1* | 5/2012 | Maeda | C07K 16/303 424/133.1 |
| 2014/0271629 A1 | 9/2014 | Corbit et al. | |
| 2014/0294823 A1 | 10/2014 | Moore et al. | |
| 2015/0284465 A1 | 10/2015 | Igawa et al. | |
| 2015/0285806 A1* | 10/2015 | Ohtomo | A61P 1/16 435/7.92 |
| 2016/0229908 A1* | 8/2016 | Igawa | A61P 17/12 |
| 2017/0096479 A1* | 4/2017 | Koenig | C07K 14/475 |

FOREIGN PATENT DOCUMENTS

| | | |
|---|---|---|
| EP | 2 202 245 B1 | 4/2009 |
| WO | WO 2006/028936 A2 | 3/2006 |
| WO | WO 2006/124269 A2 | 11/2006 |
| WO | WO 2011/107520 A1 | 9/2011 |
| WO | WO2011/131746 A2 | 10/2011 |
| WO | WO 2014/055897 A1 | 4/2014 |
| WO | WO 2016/173605 A1 | 11/2016 |
| WO | WO 2016/207278 A1 | 12/2016 |
| WO | WO 2017/046994 A1 | 3/2017 |
| WO | WO 2017/125897 A1 | 7/2017 |

OTHER PUBLICATIONS

Paul, Fundamental Immunology, 3rd Edition, pp. 292-295 (Year: 1993).*
Rudikoff et al., Proc. Natl. Acad. Sci. USA, 79(6):1979-1983 (Year: 1982).*
Colman et al., Research in Immunology, 145:33-36 (Year: 1994).*
Atwell et al., Stable Heterodimers from Remodeling the Domain Interface of a Homodimer using a Phage Display Library, Journal of Molecular Biology, 270:26-35 (1997).
Gunasekaran et al., "Enhancing Antibody Fc Heterodimer Formation through Electrostatic Steering Effects," The Journal of Biological Chemistry, 285(25):19637-19646 (2010).
Labrijn, et al., "Efficient Generation of Bispecific Murine Antibodies for Pre-Clinical Investigations in Syngeneric Rodent Models," Scientific Reports, 7(2476): 1-14 (2017).
Milstein, et al., "Hybrid hybridomas and their Use in Immunohistochemistry," Nature, 305: 537-540 (1983).
Merchant et al., "An efficient route to huyman bispecific IgG," Nature Biotechnology, 16: 677-681 (1998).
Ridgway et al., "'Knobs-into-holes' engineering of antibody $C_H3$ domains for heavy chain heterodimerization," Protein Engineering 9(7): 617-621 (1996).
Urlaub, et al., "Isolation of Chinese hamster cell mutants deficient in dihydrofolate reductase activity," Proceedings of the National Academy of Science USA, 77: 4216-4220 (1980).
Zapata et al., "Engineering linear F(ab')$_2$ fragments for efficient production in *Escherichia coli* and enhanced antiproliferative activity," Protein Engineering, 8(10):1057-1062 (1995).

(Continued)

*Primary Examiner* — Phuong Huynh
(74) *Attorney, Agent, or Firm* — Kirk Baumeister

(57) ABSTRACT

The present disclosure relates to methods of modifying the isoelectric point of an antibody. The method includes providing an antibody comprising a first polypeptide comprising a heavy chain variable region and a second polypeptide comprising heavy chain variable region and substituting, in at least one of the first and second polypeptides of the antibody, one or more amino acid residues of the heavy chain variable region ($V_H$) at positions 7, 9, 11, 14, 41, 70, 74, 82a, 84, and 113, according to the Kabat numbering system, wherein the substituting increases or decreases the isoelectric point of the antibody.

15 Claims, 50 Drawing Sheets

Specification includes a Sequence Listing.

(56) References Cited

OTHER PUBLICATIONS

PCT International Search Report dated Oct. 30, 2018.
Fan, et al., "Comparison of the three-dimensional structures of a humanized and a chimeric Fab of an anti-γ-interferon antibody," Journal of Molecular Recognition, 12: 19-32 (1999).
Sampei, et al., "Identification and Multidimensional Optimization of an Asymmetric Bispecific IgG Antibody Mimicking the Function of Factor VIII Cofactor Activity," Plos One, 8(2): 1-13 (2013).
Sharkey, et al., "Purification of common light chain IgG-like bispecific antibodies using highly linear pH gradients," mAbs, 9(2): 257-268 (2017).
Shire, et al., "Analytical tools used in the formulation and assessment of stability of monoclonal antibodies (mAbs)," Monoclonal Antibodies: Meeting the Challenges in Manufacturing, Formulation, Delivery and Stability of Final Drug Product, pp. 17-44 (2015).
Supplemental Partial European Search Report send Jan. 28, 2021.
Extended European Search Report dated Jun. 2, 2021.
Cumbers, et al., "Generation and iterative affinity maturation of antibodies in vitro using hypermutating B-cell lines," Nature Biotechnology, 20(11): 1129-1134 (2002).

\* cited by examiner

Plot: SLS at 266nm vs. Temp for 1 mg/mL

Parameter Value
Tagg     68.6°C

Plot: SLS at 266nm vs. Temp for 1 mg/mL

Parameter Value
Tagg     65.7°C

| Sample | kon (1/Ms) | koff (1/s) | KD (nM) | Binding Ratio | Chi2 (%) |
|---|---|---|---|---|---|
| PD1H170_WT (E4) | 2.21E+05 | 4.45E-04 | 2.01 | 1.11 | 8.38 |
| PD1H170_S75D (D3) | 2.45E+05 | 3.37E-04 | 1.38 | 1.08 | 7.21 |
| PD1H170_S84D (B3) | 2.55E+05 | 3.85E-04 | 1.51 | 1.07 | 5.24 |
| PD1H170_S88D (H2) | 2.59E+05 | 3.52E-04 | 1.36 | 1.11 | 6.55 |

Figure 18

METHODS OF ENGINEERING SURFACE CHARGE FOR BISPECIFIC ANTIBODY PRODUCTION

CROSS-REFERENCE TO RELATED APPLICATIONS

This application claims the benefit of U.S. Provisional Application Ser. No. 62/515,297, filed 5 Jun. 2017, the entire contents of which are incorporated herein by reference.

SEQUENCE LISTING

This application contains a Sequence Listing submitted via EFS-Web, the entire content incorporated herein by reference in its entirety. The ASCII text file, created on 16 May 2018, is named JBI5100WOPCTSEQLIST.TXT and is 18 kilobytes in size.

FIELD OF THE INVENTION

The present disclosure relates to methods of engineering surface charge to enhance bispecific antibody production.

BACKGROUND OF THE INVENTION

Antibody-based therapeutics have been used successfully to treat a variety of diseases, including cancer and autoimmune/inflammatory disorders. Yet improvements to this class of drugs are still needed, particularly with respect to enhancing their clinical efficacy. One avenue being explored is the engineering of additional and novel antigen binding sites into antibody-based drugs such that a single immunoglobulin molecule co-engages two different antigens. Such alternate antibody formats that engage two different antigens are often referred to as bispecific antibodies.

Due to their unique mechanisms of action, bispecific antibodies have received increasing attention as biotherapeutic candidates. Historically, production of IgG type bispecific antibodies involved the introduction of four nucleic acid molecules into cells, e.g., nucleic acid molecules encoding the heavy and light chain polypeptides of a first antibody specific to a given antigen, and nucleic acid molecules encoding the heavy and light chain polypeptides of a second antibody specific to a different antigen. In this system, expression of nucleic acid molecules encoding the two heavy chains and two light chains, and the generally random association between the two different heavy chains, and the heavy and light chains, resulted in a small proportion of the antibodies produced having the desired combination of heavy and light chains. Only one out of ten antibodies produced in this way achieves the proper HC and LC pairing to generate the bispecific antibody of interest. To address this issue, engineering strategies that encourage the heterodimerization of the two different HCs and proper pairing of HC with their LC partner to form the desired bispecific were conceived. Such strategies introduced mutations that disfavored undesired pairing as a result of introducing charge, hydrophobicity, steric hindrance, or a combination thereof. While these types of approaches greatly increased the proportion of bispecific antibody, other unwanted antibody species remained. Because these unwanted impurities are closely related to the desired product, they can be difficult to remove.

Mar. 16, 2006, Huang et al. (International Patent Publication No. WO 2006/028936) suggested that to facilitate purification of a desired antibody heteromultimer it may be desirable to manipulate the differential in the isoelectric points (pI) between a first polypeptide pair and a second polypeptide pair by making selective substitutions in the CDR or framework of one or more of the antibodies. Subsequent work by Igawa et al. (U.S. Patent Application Publication Nos. 20090263392 and 20110076275), disclosed methods to enhance the removal of unwanted monospecific homodimeric byproducts formed during the course of bispecific antibody production that involved engineering one or both of the half-antibodies comprising the bispecific to have a different pI. The change in pI is engineered by the introduction of one or more specific amino acid substitutions in the constant and/or variable regions of the antibody. As a result of the change in pI of one or both of the half antibodies, the desired bispecific antibody can be more readily purified from the parental monospecific homodimeric antibodies using cation exchange. Likewise, U.S. Patent Publication No. 20140294823 to Moore et al. describes a similar approach where specific amino acid substitutions in the heavy chain constant region of one of the parental antibodies creates a heterodimeric antibody where the two heavy chains have a different isoelectric point (pI).

Despite these efforts, additional methods for the purification of bispecific antibodies are still needed.

SUMMARY OF THE INVENTION

One aspect of the disclosure is directed to a method of modifying the isoelectric point of an antibody. The method involves providing an antibody comprising a first polypeptide comprising a heavy chain variable region and a second polypeptide comprising a heavy chain variable region, and substituting, in at least one of the first and second polypeptides of the antibody, one or more amino acid residues of the heavy chain variable region ($V_H$) at positions 7, 9, 11, 14, 41, 70, 74, 82a, 84, and 113, according to the Kabat numbering system, wherein the substituting increases or decreases the isoelectric point of the antibody.

A second aspect of the disclosure is directed to an antibody having a modified isoelectric point produced by the methods described herein.

A third aspect of the disclosure is directed to a method of enhancing separation of a bispecific antibody from its two parental antibodies. This method includes providing a first and second parental antibody, each parental antibody comprising a heavy chain variable region, and substituting, in at least one of the first and second parental antibodies, one or more amino acid residues in the heavy chain variable region (VH) at positions 7, 9, 11, 14, 41, 70, 74, 82a, 84, and 113, according to the Kabat numbering system, where the substituting increases or decreases the isoelectric point of the first parental antibody relative to the second parental antibody. This method further involves producing the bispecific antibody from the two parental antibodies after the substituting, and separating the produced bispecific antibody from its two parental antibodies, where the separation of the bispecific antibody is enhanced as a result of the substitutions.

A fourth aspect of the disclosure is directed to a multispecific antibody that includes a first polypeptide comprising a heavy chain variable region and a second polypeptide comprising a heavy chain variable region, wherein the isoelectric point of the first polypeptide is less than the isoelectric point of the second polypeptide. In accordance with this aspect, one or more amino acid residues at positions 9, 70, 74, 82a, and 84 (Kabat numbering) of the heavy chain variable region of the first polypeptide comprise a neutral or negatively charged amino acid residue and one or more amino acid residues at the corresponding positions of the heavy chain variable region of the second polypeptide comprise a differentially charged amino acid residue when compared to the first polypeptide.

A fifth aspect of the disclosure is directed to a multi-specific antibody that includes a first polypeptide comprising a heavy chain variable region and a second polypeptide comprising a heavy chain variable region, wherein the isoelectric point of the first polypeptide is higher than the isoelectric point of the second polypeptide. In accordance with this aspect, one or more amino acid residues at positions 7, 9, 11, 14, 41, 74, 84, and 113 (Kabat numbering) of the heavy chain variable region of the first polypeptide comprise a neutral or positively charged amino acid residue and one or more amino acid residues at the corresponding positions of the heavy chain variable region of the second polypeptide comprise a differentially charged amino acid residue when compared to the first polypeptide.

BRIEF DESCRIPTION OF THE DRAWINGS

FIG. 1A shows TNFα binding of the S75D and N84D antibody variants as compared to wildtype (148 WT and CNTO148). FIG. 1B shows TNFα binding of the A88D antibody variant compared to wildtype. FIG. 1C shows TNFα binding of the G9E and S71E antibody variants compared to wildtype. CNTO95 antibody binding to TNFα is shown as a negative control.

FIG. 2A shows the SE-HPLC profile of the CNTO148 wildtype antibody, FIG. 2B shows the SE-HPLC profile of the N84D variant, and FIG. 2C shows the SE-HPLC profile of the S75D variant.

FIG. 3A shows the SE-HPLC profile of the CNTO148 wildtype antibody, and FIG. 2B shows the SE-HPLC profile of the A88D variant.

FIG. 4A shows the SE-HPLC profile of the CNTO148 wildtype antibody, FIG. 4B shows the SE-HPLC profile of the G9E variant, FIG. 4C shows the SE-HPLC profile for the S71E variant.

FIG. 5A shows the onset of aggregation for the CNTO148 wildtype occurring at 63.9° C., FIG. 5B shows the onset of aggregation for the S75D variant antibody occurring at 66.8° C., and FIG. 5C shows the onset of aggregation for the N84D variant occurring at 65.8° C.

FIG. 6A shows that the onset of aggregation for the wildtype occurs at 67.6° C., and FIG. 6B shows the onset of aggregation for the A88D variant occurs at 66.9° C.

FIG. 7A shows that the onset of aggregation for the wildtype occurs at 68.6° C., FIG. 7B shows the onset of aggregation for the G9E variant occurs at 65.7° C., and FIG. 7C shows the onset of aggregation for the S71E variant occurs at 69.5° C.

FIG. 8A shows the unfolding temperature for the wildtype occurs at 63.9° C., FIG. 8B shows the unfolding temperature for the S75D variant occurs at 67.3° C., and FIG. 8C shows the unfolding temperature for the N84D variant occurs at 65.3° C.

FIG. 9A shows the unfolding temperature for the wildtype occurs at 67.3° C., and FIG. 9B shows the unfolding temperature for the A88D variant occurs at 66.9° C.

FIG. 10A shows the unfolding temperature for the wildtype occurs at 68.8° C., FIG. 10B shows the unfolding temperature for the G9E variant occurs at 65.8° C., and FIG. 10C shows the unfolding temperature for the S71E variant occurs at 69.5° C.

FIG. 11 shows αVβ3 binding of the S7R, G9R, V11R, P14R, P41R, S71K, A88R, and S119R antibody variants compared to CNTO95 wildtype. CNTO148 antibody binding to αVβ3 is shown as a negative control.

FIG. 12A shows the SE-HPLC profile of the CNTO95 wildtype antibody, FIG. 12B shows the SE-HPLC profile of the S7R variant, FIG. 12C shows the SE-HPLC profile of the G9R variant, FIG. 12D shows the SE-HPLC profile of the V11R variant, FIG. 12E shows the SE-HPLC profile of the P14R variant, FIG. 12F shows the SE-HPLC profile of the P41R variant, FIG. 12G shows the SE-HPLC profile of the S71K variant, FIG. 12H shows the SE-HPLC profile of the A88R variant, and FIG. 12I shows the SE-HPLC variant of the S119R variant.

FIG. 13A shows the onset of aggregation for the CNTO95 wildtype occurring at 68.2° C., FIG. 13B shows the onset of aggregation for the S7R variant antibody occurring at 67.2° C., FIG. 13C shows the onset of aggregation for the G9R variant occurring at 57.9° C., FIG. 13D shows the onset of aggregation for the V11R variant occurring at 63.9° C., FIG. 13E shows the onset of aggregation for the P14R variant occurring at 63.5° C., FIG. 13F shows the onset of aggregation for the P41R variant occurring at 66.4° C., FIG. 13G shows the onset of aggregation for the S71K variant occurring at 64.9° C., FIG. 13H shows the onset of aggregation for the A88R variant occurring at 67.6° C., and FIG. 13I shows the onset of aggregation for the S119R variant occurring at 66.7° C.

FIG. 14A shows the unfolding temperature for the wildtype occurs at 68.8° C., FIG. 14B shows the unfolding temperature for the S7R variant occurs at 67.9° C., FIG. 14C shows the unfolding temperature for the G9R variant occurs at 59.4° C., FIG. 14D shows the unfolding temperature for the V11R variant occurs at 64.8° C., FIG. 14E shows the unfolding temperature for the P14R variant occurs at 64.3° C., FIG. 14F shows the unfolding temperature for the P41R variant occurs at 66.8° C., FIG. 14G shows the unfolding temperature for the S71K variant occurs at 65.8° C., FIG. 14H shows the unfolding temperature for the A88R variant occurs at 68.0° C., and FIG. 14I shows the unfolding temperature for the S119R variant occurs at 67.6° C.

FIG. 16A shows the SE-HPLC profile of the TIM3 S75D variant, FIG. 16B shows the SE-HPLC profile of the TIM3 wildtype, FIG. 16C shows the SE-HPLC profile of the TIM3 N84D variant, and FIG. 16D shows the SE-HPLC variant of the TIM3A88D variant.

FIG. 17A shows the onset of aggregation for the S75D variant occurs at 67.5° C., FIG. 17B shows the onset of aggregation for the N84D variant occurs at 68.2° C., FIG. 17C shows the onset of aggregation for the A88D variant occurs at 66.7° C., FIG. 17D shows the onset of aggregation for the wildtype occurs at 68.5° C.

FIG. 18 shows PD1 binding kinetics for anti-PD1 single substitution variants as determined by SPR.

FIG. 19A shows the SE-HPLC profile of the PD1 S75D variant, FIG. 19B shows the SE-HPLC profile of the PD1 wildtype, FIG. 19C shows the SE-HPLC profile of the PD1 S84D variant, and FIG. 19D shows the SE-HPLC variant of the PD1 S88D variant.

FIG. 20A shows the onset of aggregation for the S75D variant occurs at 66.6° C., FIG. 20B shows the onset of aggregation for the S84D variant occurs at 66.1° C., FIG. 20C shows the onset of aggregation for the S88D variant occurs at 66.5° C., FIG. 20D shows the onset of aggregation for the wildtype occurs at 65.7° C.

FIG. 22A shows the SE-HPLC profile of the CNTO148 wildtype, FIG. 22B shows the SE-HPLC profile of the CNTO148 N84D/A88D variant, FIG. 22C shows the SE-HPLC profile of the CNTO148 S75D/A88D variant, FIG. 22D shows the SE-HPLC variant of the CNTO148 N75D/N84D/A88D variant, FIG. 22E shows the SE-HPLC profile of the CNTO148 S75D/N84D variant.

FIG. 23A shows the onset of aggregation for the CNTO148 N84D/A88D variant occurs at 66.8° C., FIG. 23B shows the onset of aggregation for the CNTO148 S75D/A88D variant occurs at 66.8° C., FIG. 23C shows the onset of aggregation for the S75D/N84D/A88D variant occurs at 67.2° C., FIG. 23D shows the onset of aggregation for the S75D/N84D variant occurs at 67.1° C. FIG. 23E shows the onset of aggregation for wildtype occurs at 66.5° C.

FIG. 24A shows the unfolding temperature for the wildtype occurs at 66.4° C., FIG. 24B shows the unfolding temperature for the N84D/A88D variant occurs at 67.1° C., FIG. 24C shows the unfolding temperature for the S75D/A88D variant occurs at 66.8° C., FIG. 24D shows the unfolding temperature for the S75D/N84D/A88D variant occurs at 66.9° C., and FIG. 24E shows the unfolding temperature for the S75D/N84D variant occurs at 67.3° C.

DETAILED DESCRIPTION OF THE INVENTION

Figure 1A:
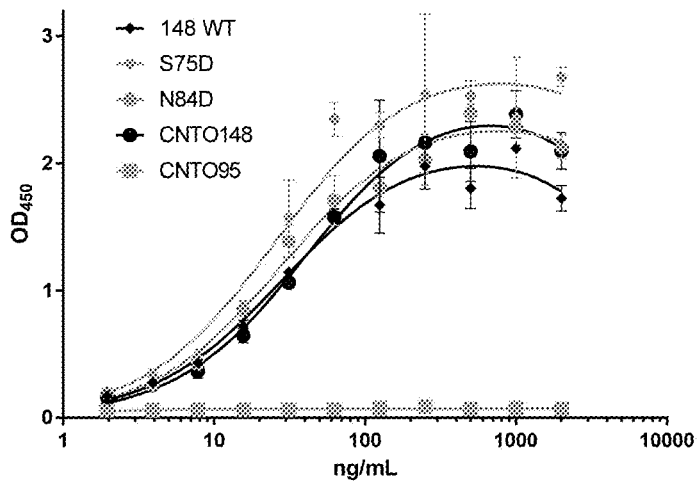
FIGS. 1A-1C are graphs of human TNFα binding ELISA of CNTO148 antibody single substitution variants.

The present disclosure generally relates to methods of engineering surface charge to enhance multi-specific antibody production and purification.

The present disclosure also relates to antibodies generated using the methods of the invention. The present disclosure also relates to anti-PD1 and anti-TIM3 antibodies and bispecific PD-1×TIM3 antibodies generated herein, and to methods of making and using them. The generated anti-PD-1, anti-TIM3 and the bispecific PD-1×TIM3 antibodies are useful as diagnostic and therapeutic agents.

Accordingly, one aspect of the present invention is directed to a method of modifying the isoelectric point of an antibody. This method involves providing an antibody comprising a first polypeptide comprising a heavy chain variable region and a second polypeptide comprising a heavy chain variable region. The method further involves substituting, in at least one of the first and second polypeptides of the antibody, one or more amino acid residues of the heavy chain variable region ($V_H$) at positions 7, 9, 11, 14, 41, 70, 74, 82a, 84, and 113, according to the Kabat numbering system, where the substituting increases or decreases the isoelectric point of the antibody.

The term "antibody" is used in the broadest sense and specifically covers monoclonal antibodies (including full length monoclonal antibodies and smaller molecules derived therefrom) and polyclonal antibodies. The term "antibody" also encompasses monovalent and multi-valent antibodies, e.g., bivalent antibodies, trivalent antibodies, and tetravalent antibodies. The term "antibody" also encompasses mono-specific and multispecific antibodies, e.g., bispecific antibodies, trispecific antibodies, tetraspecific antibodies. A multi-specific antibody is an antibody capable of binding to two or more different antigens or two different epitopes of the same antigen. Accordingly, the method of modifying the isoelectric point of an antibody as described herein is applicable to a broad variety of antibodies In one embodiment, the antibody modified in accordance with the method described herein is an immunoglobulin (Ig) molecule and comprises at least two polypeptide chains, i.e., two heavy (H) chains. Five types of mammalian Ig heavy chains are known: α, δ, ε, γ, and µ, wherein the type of heavy chain defines the class (isotype) of the antibody. Antibodies of the disclosure can be of any class (e.g., IgG, IgE, IgM, IgD, and IgA), and subclass (e.g., IgG1, IgG2, IgG3, IgG4, IgA1 and IgA2). The heavy chain may comprise the variable region ($V_H$) alone, or the variable region and the constant region ($C_H$).

The antibody modified in accordance with the method described herein may further comprise two light (L) chains. Like the heavy chain, a light chain (i.e., lambda (λ) and kappa (κ) light chains) may comprise the variable region ($V_L$) alone, or the variable region and the constant region ($C_L$).

In another embodiment, the antibody comprises heavy chain and light chain variable regions fused together to form a single-chain variable domain antibody (scFv) or a single-chain variable domain with an Fc portion (i.e., a scFv-Fc, e.g., a minibody). In another embodiment, the antibody fragment is a divalent or bivalent single-chain variable fragment, engineered by linking two scFvs together either in tandem (i.e., tandem scFv), or such that they dimerize to form diabodies. In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$-$C_H1$-$V_H$-$C_H1$) that form a pair of antigen binding regions (see Zapata et al. *Protein Eng.* 8(10):1057-1062 (1995), which is hereby incorporated by reference in its entirety).

The method described herein is also suitable for modifying the isoelectric point of chimeric antibodies (i.e., an antibody where one portion of the amino acid sequence of each of the heavy and light chains is homologous to corresponding sequences in an antibody derived from a particular species or belonging to a particular class, while the remaining segment of each chain is homologous to corresponding sequences in another species or class), CDR-grafted antibodies (i.e., antibodies which comprise heavy and light chain variable region sequences of one species, where one or more of the CDR regions are replaced with CDR regions of another species), and humanized antibodies.

Antibodies suitable for modification in accordance with the methods disclosed herein are preferably human antibodies or humanized antibodies (fully or partially humanized) as described supra. Alternatively, the antibodies can be animal antibodies such as, but not limited to, a bird antibody, a shark antibody, a whale antibody, or a mammal, including a non-primate antibody (for example, a cow, a pig, a camel, a llama, a horse, a goat, a rabbit, a sheep, a hamster, a guinea pig, a cat, a dog, a rat, a mouse, etc.) or a non-human primate antibody (for example, a monkey, a chimpanzee, etc.).

The methods described herein involve modifying the isoelectric point of an antibody. The isoelectric point (pI) of an antibody is the pH at which the antibody carries no net electrical charge. The isoelectric point of an antibody or any polypeptide is determined by its amino acid composition. For example, a polypeptide having a high number of basic amino acid residues will have a high pI, whereas a polypeptide having a high number of acidic amino acid residues will have a low pI. Accordingly, the methods of the present invention involve modifying the amino acid composition of the antibody to modify its pI. More specifically, the methods described herein involve modifying one or more amino acid residues within at least one heavy chain variable region of the antibody to modify the pI of the antibody.

The amino acid composition of a heavy chain variable region of an antibody can be modified by amino acid insertion, deletion, or substitution. An amino acid "substitution" encompasses the replacement of an amino acid residue at a particular position in a polypeptide sequence with a different amino acid. In one embodiment, the substitution involves substitution of amino acid residue that is not naturally occurring at the particular position, either not naturally occurring within the organism or in any organism. Alternatively, the one or more substitutions may be amino acid residues that are frequently occurring residues in sequences of similar related polypeptides in the same organism, e.g., conserved amino acid residues that occur frequently in sequences from other antibodies from the same species. Substitutions with conserved residues from naturally occurring sequences from the same species, e.g., human sequences, can reduce the chances of increased antigenicity for the polypeptides harboring the one or more substitutions. In addition, conservation of charge (e.g., relatively higher frequency of the same positively charged, negatively charged, or uncharged species) compared to sequences from related polypeptides in the same organism is also considered in making the amino acid residue selections for substitution. These charge considerations can have an impact on maintaining the structure and/or stability of the antibody that comprises the one or more amino acid substitutions. For purposes of modifying the pI of the antibody, the amino acid substitutions involve substituting an amino acid residue having a positive or negative charge with an amino acid residue having a neutral charge or vice versa. Exemplary substitutions include, but are not limited to: (1) substitution of a neutrally charged amino acid for a positively charged amino acid to increase the pI; (2) substitution of a negatively charged amino acid for a neutral or positively charged amino acid to increase the pI; (3) substitution of a neutrally charged amino acid for a negatively charged amino acid to decrease the pI; and (4) substitution of a positively charged amino acid with a neutral or negatively charged amino acid to decrease the pI.

An amino acid "deletion" includes the removal of one or more amino acid residues to modify the isoelectric point of the antibody, whereas an amino acid "insertion" involves the addition of one or more amino acid residues to modify the isoelectric point of the antibody. Exemplary deletions include, but are not limited to, deletion of a negatively charge amino acid residue to increase the pI or deletion of a positively charge amino acid residue to decrease the pI. Suitable amino acid additions include, but are not limited to, addition of a positive amino acid residue to increase the pI of the antibody or an addition of a negative amino acid residue to decrease the pI of the antibody.

Amino acid residues known in the art to possess a positive charge include, without limitation, those having a basic side chain, e.g., lysine (K), arginine (R), and histidine (H). Amino acid residues known in the art to possess a negative charge include, without limitation, those having an acidic side chain, e.g., glutamic acid (E) and aspartic acid (D). Amino acid residues having uncharged side chains are considered neutral, e.g., serine, threonine, asparagine, glutamine, cysteine, glycine, proline, alanine, valine, isoleucine, leucine, methionine, phenylalanine, tyrosine, and tryptophan.

Such substitutions, insertion, or deletions often involve gene manipulation or mutagenesis that modifies the original nucleic acid molecule encoding the polypeptide to be modified by inserting, deleting, or substituting at least one nucleotide, to produce a codon that encodes an amino acid residue of interest. More specifically, a codon encoding the original amino acid residue is replaced by a codon encoding the amino acid residue to be introduced by the modification. Such nucleic acid modifications can be carried out by those of skill in the art using well known techniques such as site-directed mutagenesis or PCR mutagenesis.

In accordance with the methods described herein, the amino acid substitutions, insertions, or deletions, are introduced into one or more of the heavy chain polypeptides of the antibody of interest. In particular, the amino acid substitutions, insertions, or deletions are introduced in the heavy chain variable region of the antibody of interest. The variable region of the heavy chain is subdivided into regions of hypervariability, termed complementarity determining regions (CDR). The three CDRs in the variable regions of the heavy chain are designated CDR1, CDR2 and CDR3 for each of the variable regions. The CDRs are interspersed with more conserved regions termed framework regions (FR). These FR regions are specific to place in the proper spatial configuration the contact amino acid residues of the CDRs that are responsible for most of the binding capacity of the antibody. Each $V_H$ is composed of three CDRs and four FRs, arranged from amino-terminus to carboxy-terminus in the following order: FR1, CDR1, FR2, CDR2, FR3, CDR3, FR4. The exact boundaries of these CDRs have been defined differently according to different systems. The system described by Kabat (Kabat et al., Sequences of Proteins of Immunological Interest (National Institutes of Health, Bethesda, Md. (1987) and (1991), which is hereby incorporated by reference in its entirety), which is used herein when referencing residues of the heavy chain variable region, not only provides an unambiguous residue numbering system applicable to any variable region of an antibody, but also provides precise residue boundaries defining the three CDRs. These CDRs are referred to as Kabat CDRs.

In accordance with the methods described herein, the isoelectric point of an antibody is modified by substituting, in at least one of the antibody's heavy chain variable regions, at least one amino acid residue where the amino acid residue is at position 7, 9, 11, 14, 41, 70, 74, 82a, 84, and/or 113, Kabat numbering, in the heavy chain variable region. The number of amino acid residues that undergo modification is not particularly limited. For example, in one embodiment, one amino acid substitution sufficiently modifies the isoelectric point of the antibody. In another embodiment, two amino acid substitutions sufficiently modify the isoelectric point of the antibody. In another embodiment, three, or four, or five, or six, or seven, or eight, or nine, or ten amino acid substitutions are required to sufficiently modify the isoelectric point of the antibody.

In one embodiment, the one or more amino acid residues of the $V_H$ at positions 7, 9, 11, 14, 41, 74, 84, and/or 113 (Kabat numbering) are neutrally charged amino acid residues, and the substitution step comprises exchanging the one or more neutrally charged amino acid residues with one or more positively charged amino acid residues. This substitution will increase the isoelectric point of the antibody relative to the antibody in its unmodified state (i.e., the parental or wildtype antibody).

In another embodiment, the one or more amino acid residues of the $V_H$ at positions 7, 9, 11, 14, 41, 74, 84, and/or 113 (Kabat numbering) are negatively charged amino acid residues, and the substitution step comprises exchanging said one or more negatively charged amino acid residues with one or more neutral or positively charged amino acid residues. This substitution will also increase the isoelectric point of the antibody relative to the isoelectric point of the antibody in its unmodified state.

In a further embodiment, the one or more amino acid residues of the $V_H$ at positions 9, 70, 74, 82a, and 84 (Kabat numbering) are neutrally charged amino acid residues, and the substitution step comprises exchanging said one or more neutrally charged amino acid residues with one or more negatively charged amino acid residues. This substitution will decrease the isoelectric point of the antibody relative to the isoelectric point of the unmodified, parental antibody.

In yet another embodiment, the one or more amino acid residues of the $V_H$ at positions 9, 70, 74, 82a and 84 (Kabat numbering) are positively charged amino acid residues, and the substituting comprises exchanging said one or more positively charged amino acid residues with one or more neutral or negatively charged amino acid residues. This substitution will decrease the isoelectric point of the antibody relative to the isoelectric point of the unmodified, parental antibody.

It is not necessary to exchange all of the amino acid residues described above. As noted above, amino acid substitutions can be introduced at 1, 2, 3, 4, 6, 7, 8, 9, or 10 of the identified residues within the heavy chain variable region. The number of amino acid substitutions introduced is dependent on the magnitude of change or difference in isoelectric point that is desired, i.e., 0.1 pH unit change, 0.2 pH unit change, 0.3 pH unit change, 0.4 pH unit change, 0.5 pH unit change, 0.6 pH unit change, 0.7 pH unit change, 0.8 pH unit change, 0.9 pH unit change, 1.0 pH unit change, or greater than 1.0 pH unit change. A change or difference in the isoelectric point of the modified antibody can be observed using isoelectric focusing. Isoelectric focusing is an electrophoretic technique that separates proteins by their isoelectric point. Proteins can be applied to a polyacrylamide gel (IEF gels) or immobilized pH gradient (IPG) strips containing a fixed pH gradient. An electrical field is applied and the protein migrates through the pH gradient, becoming immobilized in the pH gradient as they approach their specific pI. Alternatively, a theoretical isoelectric point can be determined using gene and amino acid sequence analysis software (GENETYX and the like). This is useful when considerable modification of the isoelectric point is necessary, for example, for sufficient separation of bispecific antibodies from parental antibodies.

In one embodiment, the substitution comprises exchanging the $V_H$ amino acid residue at position 74 (Kabat numbering) in at least one of the first or second heavy chain polypeptides of an antibody with a negatively charged amino acid residue.

In another embodiment, the substitution comprises exchanging the $V_H$ amino acid residue at position 82a (Kabat numbering) in at least one of the first or second heavy chain polypeptides of an antibody with a negatively charged amino acid residue.

In a further embodiment, the substitution comprises exchanging the $V_H$ amino acid residue at position 84 (Kabat numbering) in at least one of the first or second heavy chain polypeptides of an antibody with a negatively charged amino acid residue.

In yet another embodiment, the substitution comprises exchanging the $V_H$ amino acid residue at at least two of the positions selected from positions 74, 82a, and 84 (Kabat numbering) in at least one of the first or second heavy chain polypeptides of an antibody with a negatively charged amino acid residue.

In another embodiment, the substitution comprises exchanging the $V_H$ amino acid residue at all three positions 74, 82a, and 84 (Kabat numbering) in at least one of the first or second heavy chain polypeptides of an antibody with a negatively charged amino acid residue.

In carrying out the methods described herein, the amino acid substitutions made to an antibody to modify its isoelectric point do not alter its antigen binding capacity, i.e., the modified antibody retains the antigen-binding activity of the unmodified wildtype or parental antibody. As used herein, "retains the antigen-binding activity" means the antibody maintains at least 75%, at least 80% or more, 85% or more, 90% or more, 95% or more, i.e., 96%, 97%, 98%, 99%, or 100% of the antigen binding activity of the antibody before modification. As long as sufficient binding activity for binding to the antigen can be retained for the antibody to exert its function, the affinity determined at 37° C. under physiological conditions may be, for example, 100 nM or less, preferably 50 nM or less, more preferably 10 nM or less, and still more preferably 1 nM or less. Whether a polypeptide comprising an antibody variable region with a modified isoelectric point obtained by the methods described herein retains the antigen-binding activity can be tested using methods that are well known to those of skill in the art, such as, but not limited to, Biacore (intermolecular interaction analysis), cell proliferation assay, ELISA (enzyme-linked immunosorbent assay), EIA (enzyme immunoassay), RIA (radioimmunoassay), and fluorescence immunoassay.

In carrying out the methods described herein, the amino acid substitutions made to an antibody to modify its isoelectric point do not alter the antibody's stability, e.g., its conformation stability. In other words, the modified antibody exhibits substantially the same stability of the unmodified wildtype or parental antibody. As used herein, "substantially the same stability" means that the modified protein has a less than 25% change in stability, less than 20% change in stability, less 15% change in stability, less than 10% change in stability, less than 5%, 4%, 3%, 2%, or 1% change in stability. Parameters that can be measured as indicators of antibody stability include, but are not limited to, unfolding transition temperature, aggregation onset temperature, and rates of aggregation. Other parameters of antibody stability that can be measured include in vitro serum stability, degradation levels, biological activity, pH, color, clarity, chemical stability, and physical stability.

In one embodiment, the antibody having a modified isoelectric point is a monospecific antibody. In accordance with this embodiment, the first and second polypeptides, each comprising a heavy chain variable region of the parental monospecific antibody are the same, and the same substitutions to the one or more identified amino acid residue positions (i.e., residues 7, 9, 11, 14, 41, 70, 74, 82a, 84, and/or 113) are made in both the first and second heavy chain polypeptides to generate a variant antibody having an isoelectric point that is different than the isoelectric point of the parental antibody.

The methods described herein can be utilized to modify the isoelectric point of virtually any monospecific antibody previously known in the art or to be developed. By way of example only, a monospecific antibody that has been modified using the methods described herein is the monoclonal antibody that binds TNFα known as CNTO148. As described herein the heavy chain variable region of the CNTO148 antibody was modified at Kabat residues 74, 82a, and 84, which correspond to residues 75, 84, and 88, respectively of the SEQ ID NO: 1 (shown below) to decrease its isoelectric point.

```
CNTO148 heavy chain variable region (C14F1)-
                                        SEQ ID NO: 1
QVQLVESGGGVVQPGRSLRLSCAASGFIFSSYAMEIWVRQAPGNGLEWVA

FMSYDGSNKKYADSVKGRFTISRDN

[S/D]KNTLYLQM[N/D]SLR[A/D]EDTAVYYCARDRGIAAGGNYYYYG

MDVWGQGTTVTVSS
```

In particular, the serine residue at position 75 of SEQ ID NO: 1 was substituted with an aspartic acid residue (S75D), the asparagine residue at position 84 of SEQ ID NO: 1 was substituted with an aspartic acid residue (N84D), and the alanine residue at position 88 of SEQ ID NO: 1 was substituted with an aspartic acid residue (A88D) to decrease the isoelectric point of the CNTO148 antibody. These amino acid substitutions had no effect on antigen binding capabilities of the CNTO148 antibody (see FIGS. 1A, 1B and 1C).

Another monospecific antibody that has been modified using the methods described herein is the monoclonal antibody that binds TIM3 (CD366) known as TIMB337. As described herein the heavy chain variable region of the TIMB337 antibody (TM3H24 HC) was modified at Kabat residues 74, 82a, and 84, which correspond to residues 75, 84, and 88, respectively of the SEQ ID NO: 2 (shown below) to decrease its isoelectric point. TIMB337 comprises a light chain variable region of SEQ ID NO: 5.

```
TIMB377 heavy chain variable region (TM3H24)-
                                        SEQ ID NO: 2
EVQLLESGGGLVQPGGSLRLSCAASGFTFSSYAMSWVRQAPGKGLEWVSA
ISGSGGSTYYADSVKGRFTISRDN[S/D]KNTLYLQM[N/D]SLR[A/D]
EDTAVYYCAKSPYAPLDYWGQGTLVTVSS;

TIMB377 light chain variable region-
                                        SEQ ID NO: 5
EIVLTQSPATLSLSPGERATLSCRASQSVNDYLAWYQQKPGQAPRLLIYD
ASNRATGIPARFSGSGSGTDFTLTISSLEPEDFAVYYCQQGGHAPITFGQ
GTKVEIK
```

Figure 15:
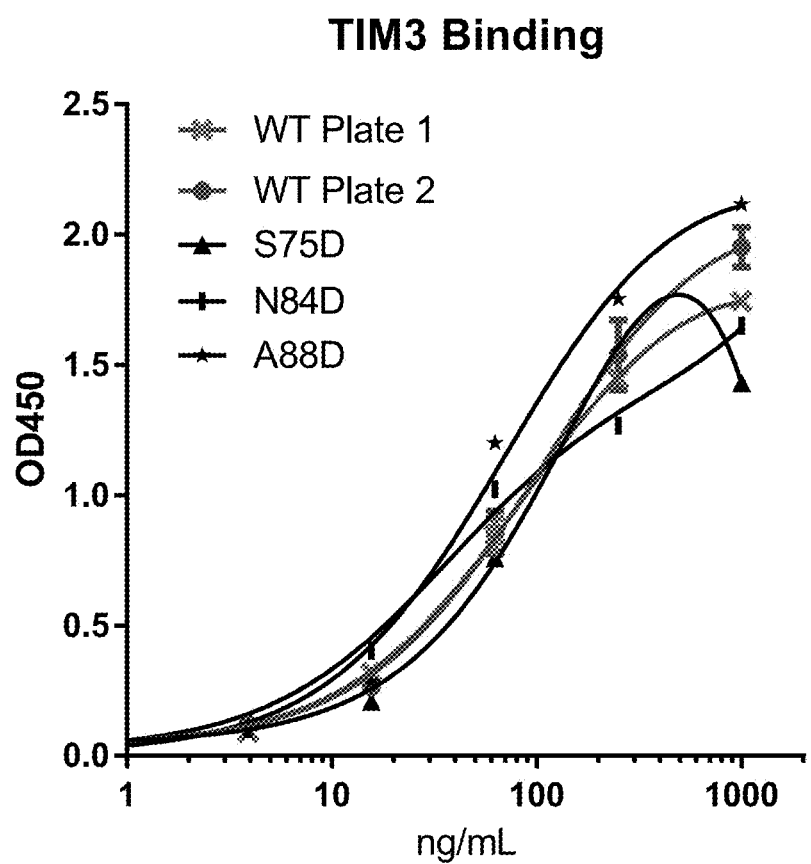
FIG. 15 shows human TIM3 binding ELISA of anti-TIM3 antibody single substitution variants.
Figure 16A:
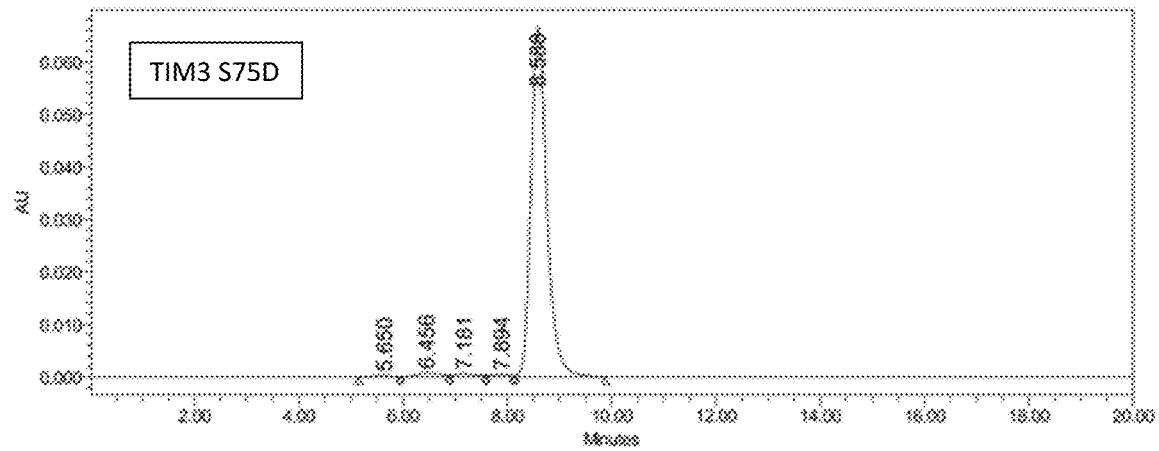
FIGS. 16A-16D shows analytical SE-HPLC analysis of anti-TIM3 single substitution variants.
Figure 16B:
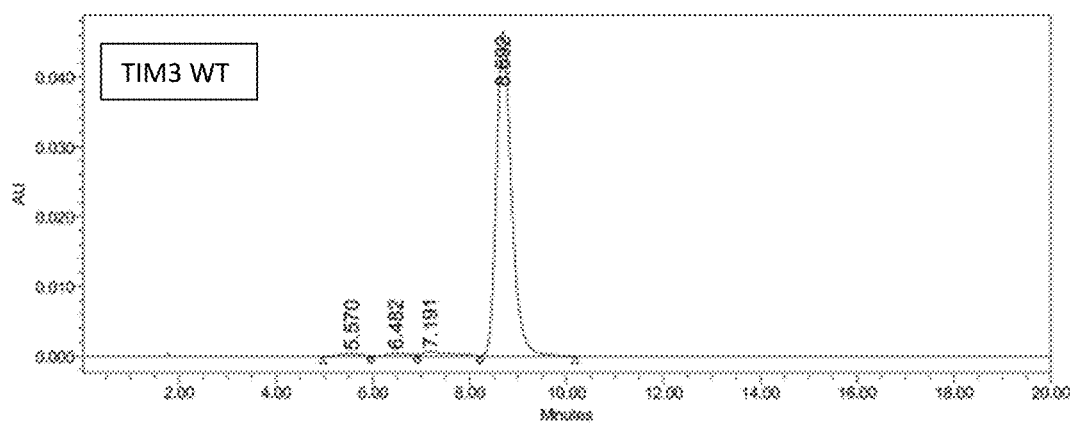
Figure 16C:
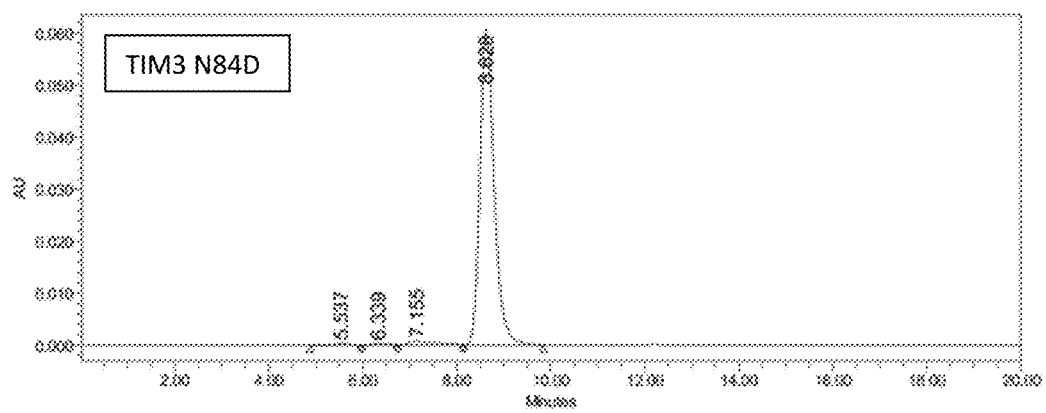
Figure 16D:
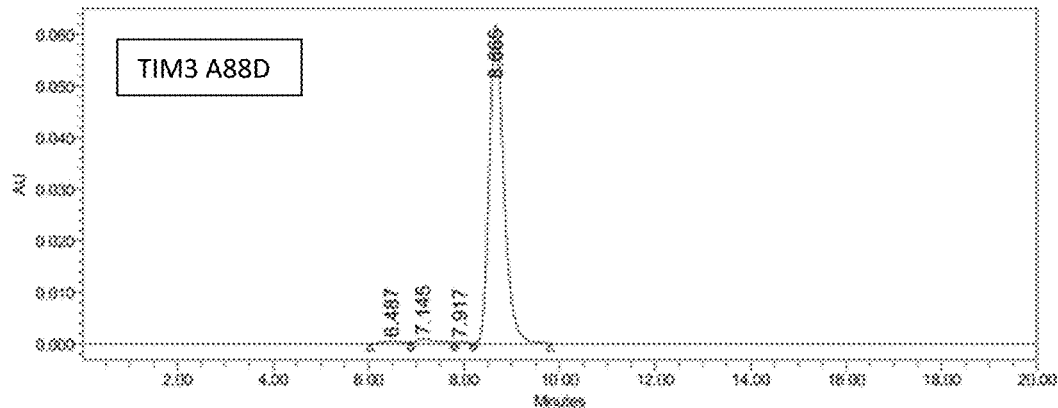
Figure 17A:
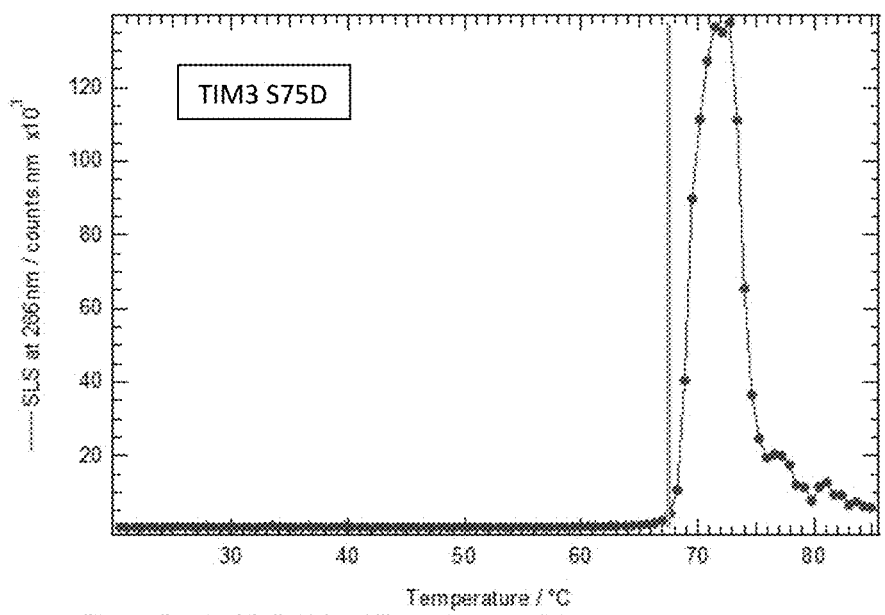
FIGS. 17A-17D shows onset of aggregation (colloidal stability) analysis of anti-TIM3 single substitution variants.
Figure 17B:
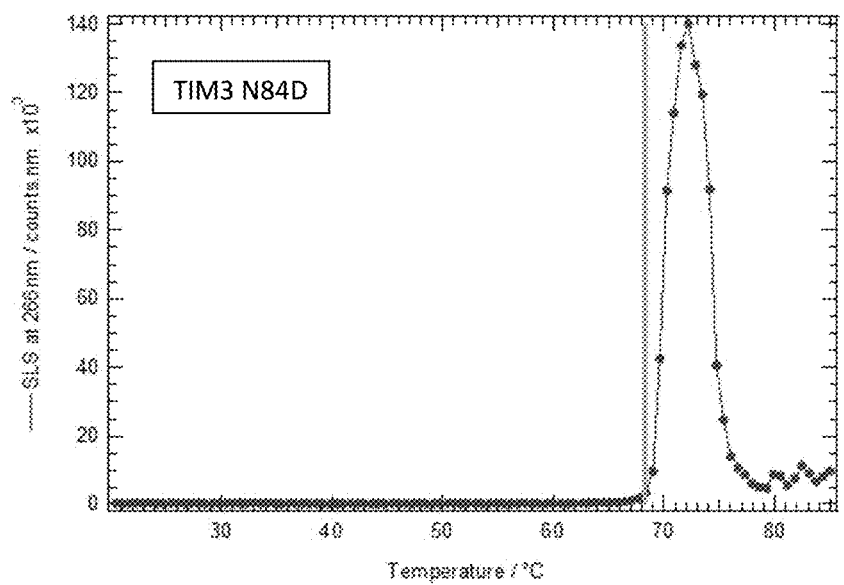
Figure 17C:
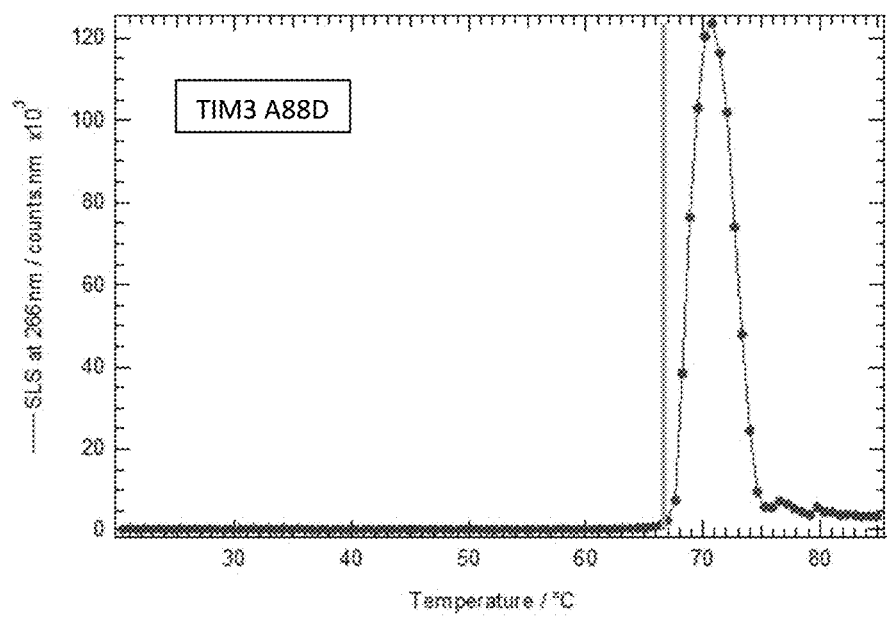
Figure 17D:
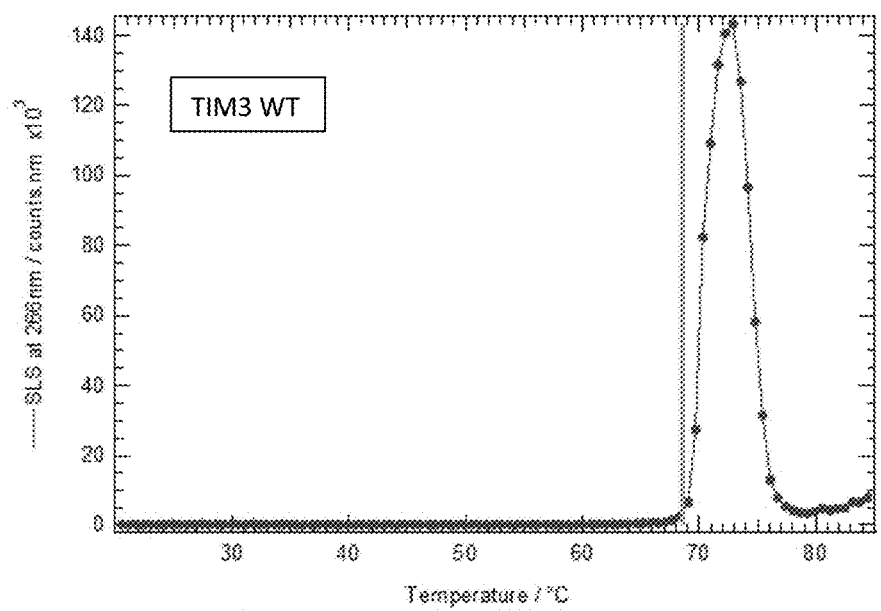
Figure 19A:
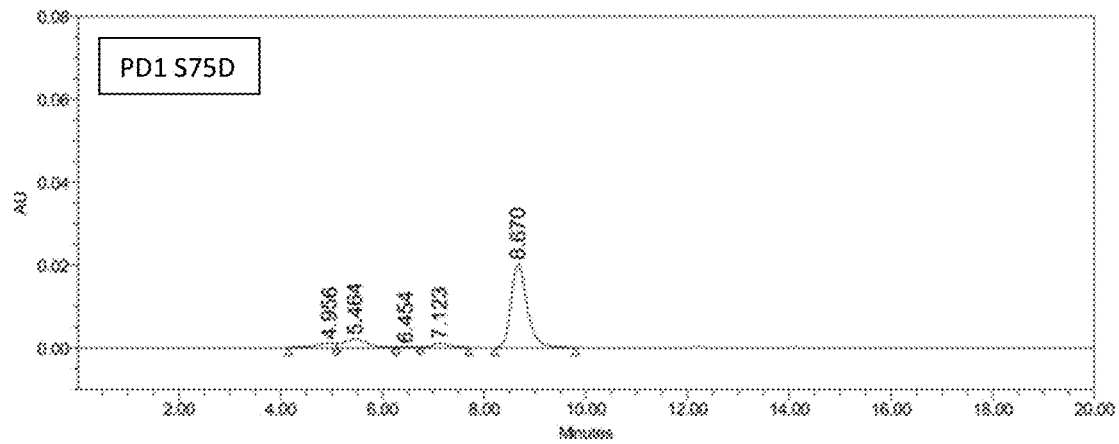
FIGS. 19A-19D show analytical SE-HPLC analysis of anti-PD1 antibody single substitution variants.
Figure 19B:
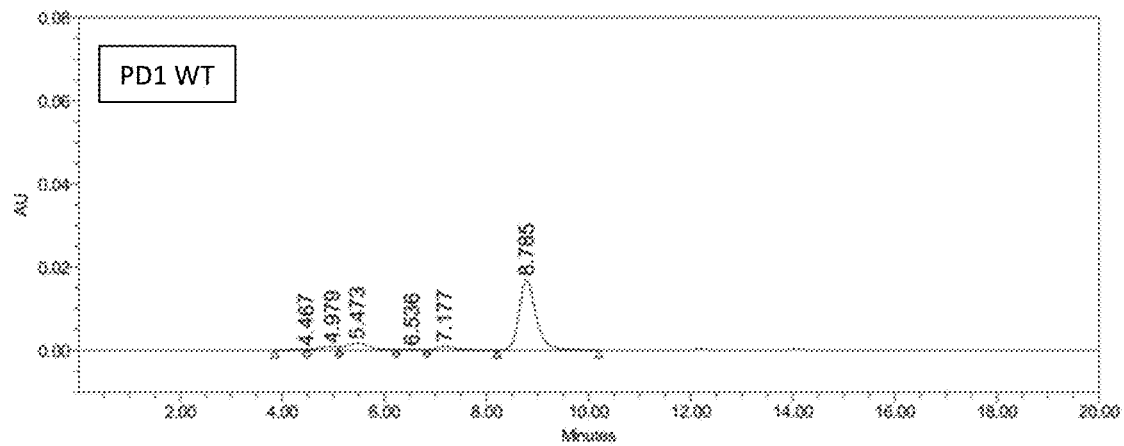
Figure 19C:
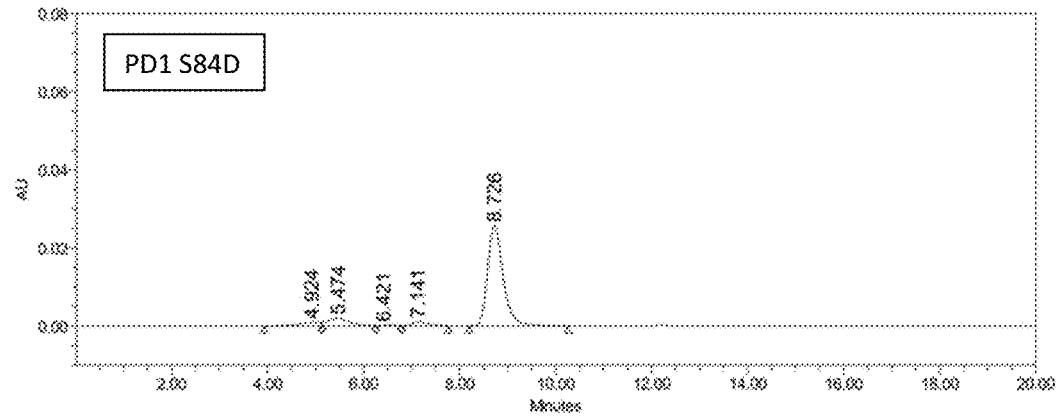
Figure 19D:
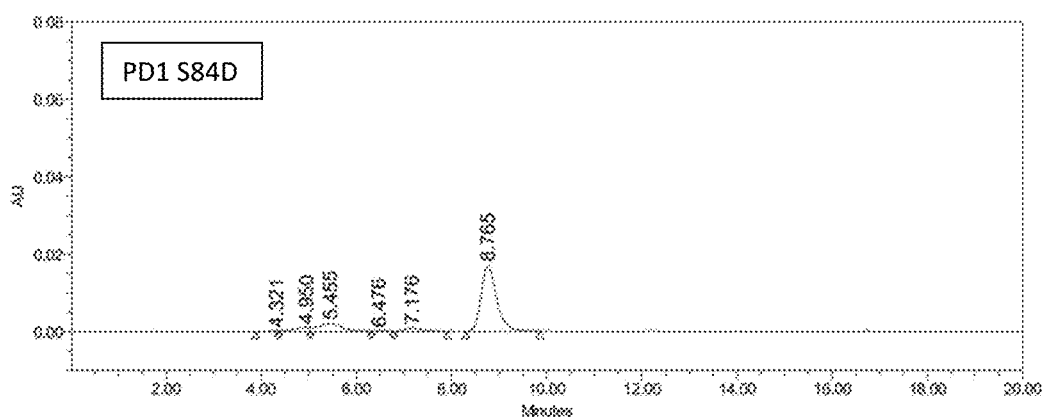
Figure 20A:
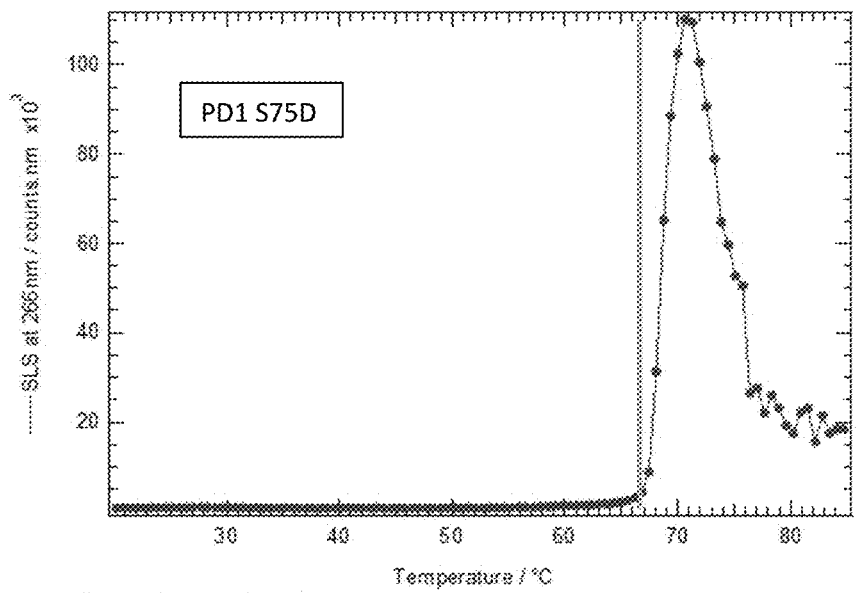
FIGS. 20A-20D show onset of aggregation (colloidal stability) analysis of anti-PD1 single substitution variants.
Figure 20B:
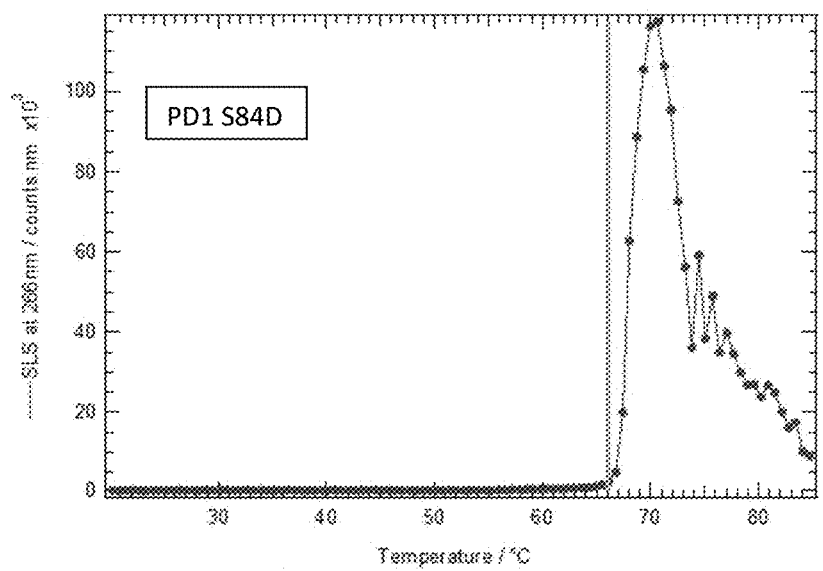
Figure 20C:
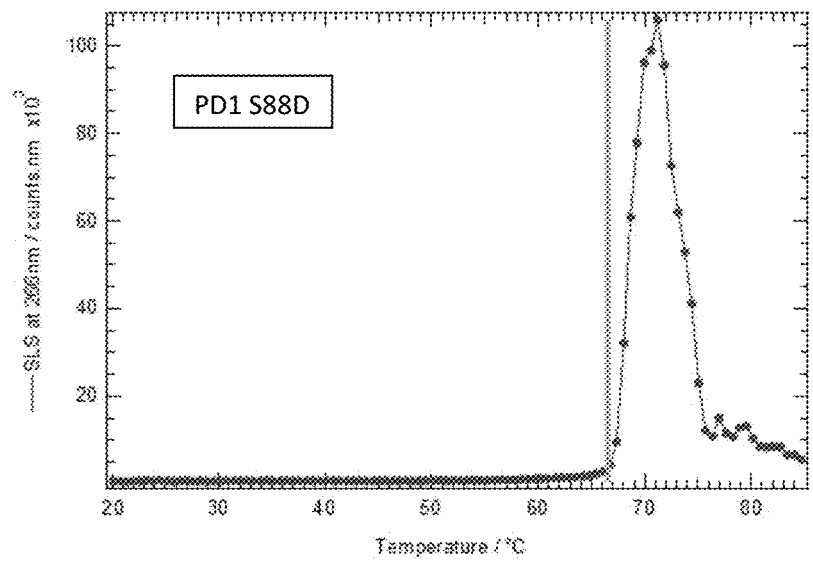
Figure 20D:
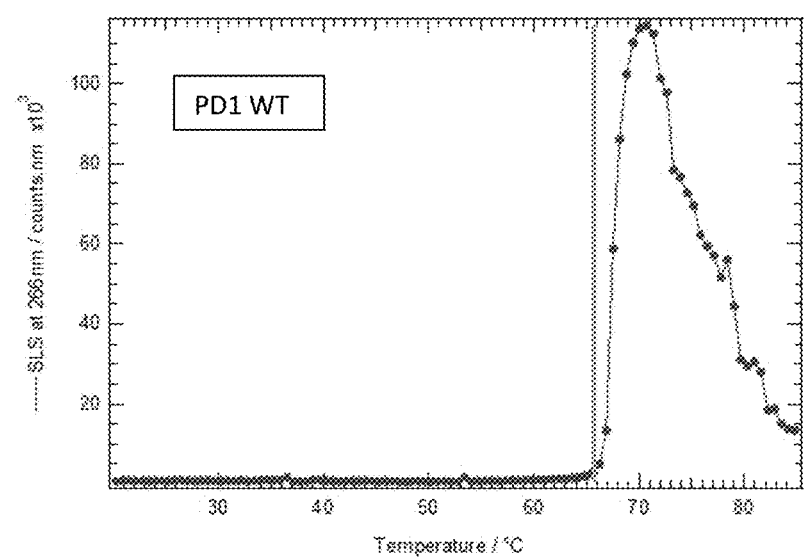

In particular, the serine residue at position 75 of SEQ ID NO: 2 was substituted with an aspartic acid residue (S75D), the asparagine residue at position 84 of SEQ ID NO: 2 was substituted with an aspartic acid residue (N84D), and the alanine residue at position 88 of SEQ ID NO: 2 was substituted with an aspartic acid residue (A88D) to decrease the isoelectric point of the TIMB337 antibody. These amino acid substitutions had no effect on antigen binding capabilities of the TIMB337 antibody (see FIG. 15). The amino acid sequences of TIMB337 $V_H$ variants are shown below.

```
S75D variant of TM3B337 VH
                                        SEQ ID NO: 6
EVQLLESGGGLVQPGGSLRLSCAASGFTFSSYAMSWVRQAPGKGLEWVSA
ISGSGGSTYYADSVKGRFTISRDNDKNTLYLQMNSLRAEDTAVYYCAKSP
YAPLDYWGQGTLVTVSS N84D variant of TM3B337 VH
                                        SEQ ID NO: 7
EVQLLESGGGLVQPGGSLRLSCAASGFTFSSYAMSWVRQAPGKGLEWVSA
ISGSGGSTYYADSVKGRFTISRDNSKNTLYLQMDSLRAEDTAVYYCAKSP
YAPLDYWGQGTLVTVSS A88D variant of TM3B337 VH
                                        SEQ ID NO: 8
EVQLLESGGGLVQPGGSLRLSCAASGFTFSSYAMSWVRQAPGKGLEWVSA
ISGSGGSTYYADSVKGRFTISRDNSKNTLYLQMNSLRDEDTAVYYCAKSP
YAPLDYWGQGTLVTVSS
```

Another monospecific antibody that has been modified using the methods described herein is the monoclonal antibody that binds PD-1 (CD279) known as PD1B244. As described herein the heavy chain variable region of the PD1B244 antibody (PD1H170 HC) was modified at Kabat residues 74, 82a, and 84, which correspond to residues 75, 84, and 88, respectively of the SEQ ID NO: 3 (shown below) to decrease its isoelectric point. PD1B2244 comprises a light chain variable region of SEQ ID NO: 9.

```
PD1B244 heavy chain variable region PD1H170-
                                        SEQ ID NO: 3
QVQLVQSGAEVKKPGSSVKVSCKASGGTFSSYAISWVRQAPGQGLEWMGG
IIPIFDTANYAQKFQGRVTITADE[S/D]TSTAYMEL[S/D]SLR[S/D]
EDTAVYYCARPGLAAAYDTGSLDYWGQGTLVTVSS
```

-continued

PD1B244 light chain variable region-
SEQ ID NO: 9
EIVLTQSPATLSLSPGERATLSCRASQSVRSYLAWYQQKPGQAPRLLIYD
ASNRATGIPARFSGSGSGTDFTLTISSLEPEDFAVYYCQQRNYWPLTFGQ
GTKVEIK In particular, the serine residue at position 75 of SEQ ID NO: 3 was substituted with an aspartic acid residue (S75D), the serine residue at position 84 of SEQ ID NO: 3 was substituted with an aspartic acid residue (S84D), and the serine residue at position 88 of SEQ ID NO: 3 was substituted with an aspartic acid residue (S88D) to decrease the isoelectric point of the PD1B244 antibody. These amino acid substitutions had no effect on antigen binding capabilities of the PD1B244 antibody (see FIG. 18). The amino acid sequences of PD1B244 $V_H$ variants are shown below.

S75D variant of PD1B244 VH
SEQ ID NO: 10
QVQLVQSGAEVKKPGSSVKVSCKASGGTFSSYAISWVRQAPGQGLEWMGG
IIPIFDTANYAQKFQGRVTITADEDTSTAYMELSSLRSEDTAVYYCARPG
LAAAYDTGSLDYWGQGTLVTVSS S84D variant of PD1B244 VH
SEQ ID NO: 11
QVQLVQSGAEVKKPGSSVKVSCKASGGTFSSYAISWVRQAPGQGLEWMGG
IIPIFDTANYAQKFQGRVTITADESTSTAYMELDSLRSEDTAVYYCARPG
LAAAYDTGSLDYWGQGTLVTVSS S88D variant of PD1B244 VH
SEQ ID NO: 12
QVQLVQSGAEVKKPGSSVKVSCKASGGTFSSYAISWVRQAPGQGLEWMGG
IIPIFDTANYAQKFQGRVTITADESTSTAYMELSSLRDEDTAVYYCARPG
LAAAYDTGSLDYWGQGTLVTVSS In another embodiment, the antibody having a modified isoelectric point is a multispecific antibody, e.g., a bispecific antibody. In accordance with this embodiment, the first and second polypeptides comprising the heavy chain variable region of the multispecific antibody are different. In accordance with this embodiment, the amino acid substitutions disclosed herein may be present in only one of the heavy chain variable regions. Alternatively, amino acid substitutions may be made in both heavy chain variable regions, these substitutions may be the same or different depending on the purpose of the modification. For example, if the isoelectric modification is made to alter the half life/clearance rate of the multispecific antibody, then similar substitutions in both heavy chain variable regions may be made to increase or decrease the pI of the antibody. Alternatively, different amino acid substitutions may be made in both heavy chain variable regions to increase or decrease the pI of the antibody.

In another embodiment, the amino acid substitutions are present in only one heavy chain variable region of a multispecific antibody, e.g., a bispecific antibody. This is approach is desired when the bispecific antibody is generated from two parental antibodies having similar pIs. When two parental antibodies having the same or similar isoelectric points are utilized to generate a bispecific antibody, the separation and purification of the bispecific antibody produced therefrom using the standard cell recombination and expression techniques is severely hampered. Accordingly, modification of the parental antibodies to increase the difference in pIs between them will result in the production of a bispecific antibody that can be more readily separated and distinguished from its parental antibodies, thereby increasing the yield and purity of bispecific antibody production.

Accordingly, another aspect of the present disclosure is directed to a method of enhancing separation of a bispecific antibody from its two parental antibodies. This method includes providing a first and second parental antibody, each parental antibody comprising a heavy chain variable region. The method further includes substituting, in at least one of the first and second parental antibodies, one or more amino acid residues in the heavy chain variable region (VH) at positions 7, 9, 11, 14, 41, 70, 74, 82a, 84, and 113, according to Kabat numbering system, wherein the substituting increases or decreases the isoelectric point of the first parental antibody relative to the second parental antibody. The method further involves producing the bispecific antibody from the two parental antibodies after said substituting, and separating the bispecific antibody produced from its two parental antibodies, where the separation of the bispecific antibody from its two parental antibodies is enhanced as a result of said substituting.

In accordance with this aspect, when one or more amino acid residues of the $V_H$ region at positions 7, 9, 11, 14, 41, 74, 84, and 113 (Kabat numbering) of the first parental antibody are neutrally charged amino acid residues, one or more of these amino acid residues may be substituted with one or more positively charged amino acid residues. This substitution will increase the isoelectric point of the first parental antibody relative to the isoelectric point of the second parental antibody. Alternatively, when the one or more amino acid residues of the $V_H$ region at positions 7, 9, 11, 14, 41, 74, 84, and 113 (Kabat numbering) of the first parental antibody are negatively charged amino acid residues, the amino acid residues may be substituted by exchanging the one or more negatively charged amino acid residues with one or more neutral or positively charged amino acid residues. This substitution will also increase the isoelectric point of the first parental antibody relative to the second parental antibody.

In another embodiment, when the one or more amino acid residues of the $V_H$ region at positions 9, 70, 74, 82a, and 84 (Kabat numbering) of the first parental antibody are neutrally charged amino acid residues, one or more of these amino acid residues may be substituted by exchanging said one or more neutrally charged amino acid residues with one or more negatively charged amino acid residues. This substitution will to decrease the isoelectric point of the first parental antibody relative to the second parental antibody. In a further embodiment, when the one or more amino acid residues of the $V_H$ region at positions 9, 70, 74, 82a, and 84 (Kabat numbering) of the first parental antibody are positively charged amino acid residues, one or more of these amino acid residues may be substituted by exchanging said one or more positively charged amino acid residues with one or more neutral or negatively charged amino acid residues. This substitution will also decrease the isoelectric point of the first parental antibody relative to the second parental antibody.

As described above, the number of amino acid residues that are modified or substituted in the first or second parental antibody are not limited. In one embodiment, the substitutions that create a 0.1 pH unit, 0.2 pH unit, 0.3 pH unit, 0.4 pH unit, or 0.5 pH unit, 0.6 pH unit, 0.7 pH unit, 0.8 pH unit, 0.9 pH unit, 1.0 pH unit change in the isoelectric point of the first parental antibody relative to the second parental antibody are made. In another embodiment, substitution that create a >1.0 pH unit change in the isoelectric point of the first parental antibody relative to the second parental antibody are made. These changes can be achieved with 1, 2, 3, 4, 5, 6, 7, 8, 9 or 10 amino acid substitutions. The amino acid residue substitutions described above may be carried out in the $V_H$ region of either one of the first or second parental antibodies or, alternatively, in both of the first or second parental antibodies. When amino acid substitutions are made to both the first and second parental antibodies, the one or more amino acid substitutions in the $V_H$ region of the first parental antibody will decrease the isoelectric point of the first parental antibody, while the one or more amino acid substitutions in the $V_H$ region of the second parental antibody will increase the isoelectric point of the second parental antibody. The amino acid substitutions made to both the first and second parental antibodies may be made at the same amino acid residue position (albeit be different substitutions) or be made at different amino acid residue positions.

In one embodiment, the $V_H$ amino acid residue at position 74 (Kabat numbering) in the first parental antibody is exchanged with a negatively charged amino acid residue to decrease the isoelectric point of the first parental antibody relative to the second parental antibody.

In another embodiment, the $V_H$ amino acid residue at position 82a (Kabat numbering) in the first parental antibody is exchanged with a negatively charged amino acid residue to decrease the isoelectric point of the first parental antibody relative to the second parental antibody.

In another embodiment, the $V_H$ amino acid residue at position 84 (Kabat numbering) in the first parental antibody is exchanged with a negatively charged amino acid residue to decrease the isoelectric point of the first parental antibody relative to the second parental antibody.

In a further embodiment, the $V_H$ amino acid residue at at least two of the positions selected from positions 74, 82a, and 84 (Kabat numbering) in the first parental antibody are exchanged with a negatively charged amino acid residue to decrease the isoelectric point of the first parental antibody relative to the second parental antibody.

In yet another embodiment, the $V_H$ amino acid residue at all three positions 74, 82a, and 84 (Kabat numbering) in the first parental antibody are exchanged with a negatively charged amino acid residue to decrease the isoelectric point of the first parental antibody relative to the second parental antibody.

As described above, the modification of the isoelectric points of the first and second parental antibodies results in the production of a bispecific antibody having an isoelectric point that is different from each of the parental antibodies. Therefore, separation and ultimately the recovery of the bispecific antibody of interest is significantly enhanced using ion exchange chromatography methods.

Methods of making bispecific antibodies are known in the art, and the method of the present disclosure can generally be incorporated into any of these known methods to enhance the separation and purification of the bispecific antibodies. Traditional production of full length bispecific antibodies is based on the coexpression of two immunoglobulin heavy chain-light chain pairs, where the two chains have different specificities (Millstein et al., Nature 305:537-539 (1983), which is hereby incorporated by reference in its entirety). As a result of the random assortment and recombination of immunoglobulin heavy and light chains, these hybridomas (quadromas) produce a potential mixture of 10 different antibody molecules, of which only one has the correct bispecific structure. Using the methods disclosed herein to increase the difference in the isoelectric points of the parental antibodies will significantly enhance the separation and purification of the desired bispecific antibody form the parental antibodies and other byproducts.

Other methods for making bispecific antibodies include, without limitation, the "knobs and holes" technique, which involves amino acid engineering that creates steric influences to favor heterodimeric formation and disfavor homodimeric formation, as described in U.S. Pat. No. 8,216,805 to Carter, see also Ridgway et al., Protein Engineering 9(7):617 (1996); and Atwell et al., J. Mol. Biol. 1997 270:26 all of which are hereby incorporated by reference in their entirety. In addition, as described in Merchant et al., Nature Biotech. 16:677 (1998), which is hereby incorporated by reference in its entirety, these "knobs and holes" mutations can be combined with disulfide bonds to skew formation to heterodimerization.

An additional technique used to generate bispecific antibodies is often referred to as "electrostatic steering" or "charge pairs" as described in Gunasekaran et al., J. Biol. Chem. 285(25):19637 (2010), which is hereby incorporated by reference in its entirety. In this method, electrostatics are used to skew the formation towards the desired heterodimerization.

Separating the bispecific antibody from the parental antibodies is done using standard separation techniques known in the art. For example, ion-exchange chromatography, is commonly used to separate a bispecific antibody from its parental antibodies. Briefly, the mixture of parental and bispecific antibodies are bound to a cation exchange material (or, alternatively, an anion exchange material) using a loading buffer, wherein the loading buffer is at a first conductivity and pH. The cation exchange material is washed with an intermediate buffer at a second conductivity and/or pH which is greater than that of the loading buffer so as to elute the contaminant (i.e., parental antibodies) from the ion exchange material. The cation exchange material is washed with a wash buffer which is at a third conductivity and/or pH which is less than that of the intermediate buffer and then washed with an elution buffer at a fourth conductivity and/or pH which is greater than that of the intermediate buffer so as to elute the desired bi-specific antibody from the ion exchange material.

Separation and purification of bispecific antibodies can also be achieved using other chromatographic techniques such as hydrophobic interaction chromatography, affinity chromatography, size exclusion/gel filtration chromatography, and reversed-phase chromatography carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. For general guidance in suitable purification techniques, see e.g. ROBERT SCOPES, Protein Purification: Principles and Practice, 3rd Ed (Springer-Verlag 1994), which is hereby incorporated by reference in its entirety.

The antibodies described herein containing the one or more amino acid substitutions suitable for increasing or decreasing the pI of the antibody, may further comprise one or more additional amino acid substitutions previously identified as being useful for modifying the surface charge and pI of an antibody, including, but not limited to amino acid substitutions identified in U.S. Patent Application Publication No. 20140294823 to Moore and U.S. Patent Application Publication No. 20090263392 to Igawa et al., which are hereby incorporated by reference in their entirety. Likewise, the antibodies described herein may further comprise additional amino acid substitutions in the Fc region known to alter a variety of additional functionalities such as FcγR binding and/or FcRn binding. Optimized Fc variants are known in the art, see e.g., U.S. Pat. No. 8,188,231 to Lazar, U.S. Pat. No. 9,040,041 to Desjarlais et al., and U.S. Pat. No. 8,802,820 to Chamberlain et al., all of which are hereby incorporated by reference in their entirety.

As described above, the antibodies described herein can be prepared by any of a variety of techniques using isolated polynucleotides, vectors, and host cells. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA*, 77: 4216-4220 (1980), which is hereby incorporated by reference in its entirety). Other suitable mammalian host cells include, without limitation, NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

The present disclosure is also directed to an antibody having a modified isoelectric point produced by the methods described herein. As described supra, the isoelectric point of virtually any antibody can be modified using the methods described herein, so long as the antibody contains a variable heavy region.

A fourth aspect of the disclosure is directed to a multi-specific antibody that includes a first polypeptide comprising a heavy chain variable region and a second polypeptide comprising a heavy chain variable region, wherein the isoelectric point of the first polypeptide is less than the isoelectric point of the second polypeptide as a result of one or more amino acid residues at positions 9, 70, 74, 82a, and 84 (Kabat numbering) of the heavy chain variable region of the first polypeptide comprising a neutral or negatively charged amino acid residue and one or more amino acid residues at the corresponding positions of the heavy chain variable region of the second polypeptide comprising a differentially charged amino acid residue when compared to the first polypeptide.

Methods of producing antibodies as well as modes of making amino acid substitutions are described above. In one embodiment, the neutral or negatively charged amino acid residues at positions 9, 70, 74, 82a and 84 of the first polypeptide are introduced into the first polypeptide by way of amino acid substitution.

In accordance with this aspect of the disclosure, an exemplary bi-specific antibody disclosed herein is an antibody that binds TNFα and αVβ3. This antibody has a first polypeptide comprising a heavy chain variable region that, together with its light chain bind TNFα (CNTO148). The isoelectric point of this first heavy chain polypeptide is less than the isoelectric point of the second heavy chain polypeptide of the antibody, which, together with its light chain bind αVβ33.

In one embodiment, the first polypeptide heavy chain variable region comprises the amino acid sequence of SEQ ID NO: 1, where the residue at position 75 (corresponding to Kabat residue 74) is a negatively charged amino acid residue, such as an aspartic acid residue (CNTO148 S75D). Alternatively, the heavy chain variable region comprises the amino acid sequence of SEQ ID NO: 1, where the amino acid residue at position 84 (corresponding to Kabat residue 82a) is a negatively charged amino acid residue, such as an aspartic acid residue (CNTO148 N84D). In yet another embodiment, the heavy chain variable region comprises the amino acid sequence of SEQ ID NO: 1, where the amino acid residue at position 88 (corresponding to Kabat residue 84) is a negatively charged amino acid residue, such as an aspartic acid residue (CNTO148 A88D).

In yet another embodiment, the heavy chain variable region comprises more than one amino acid substitution that decreases the pI of the bispecific antibody. In particular, in one embodiment, the heavy chain variable region comprises the amino acid sequence of SEQ ID NO: 1, wherein the amino acid residues as positions 84 and 88 (corresponding to Kabat residues 82a and 84) are negatively charged amino acid residues, such as aspartic acid residues (CNTO148 N84D and A88D). In another embodiment, the heavy chain variable region comprises the amino acid sequence of SEQ ID NO: 1, wherein the amino acid residues as positions 75 and 88 (corresponding to Kabat residues 74 and 84) are negatively charged amino acid residues, such as aspartic acid residues (CNTO148 S75D and A88D). In another embodiment, the heavy chain variable region comprises the amino acid sequence of SEQ ID NO: 1, wherein the amino acid residues as positions 75 and 84 (corresponding to Kabat residues 74 and 82a) are negatively charged amino acid residues, such as aspartic acid residues (CNTO148 S75D and N84D). In yet another embodiment, the heavy chain variable region comprises the amino acid sequence of SEQ ID NO: 1, wherein the amino acid residues as positions 75, 84, and 88 (corresponding to Kabat residues 74, 82a, and 84) are negatively charged amino acid residues, such as aspartic acid residues (CNTO148 S75D, N84D, and A88D).

As indicated above, this exemplary bispecific antibody has a second polypeptide comprising a heavy chain variable region that, together with its light chain bind αVβ3. This second polypeptide comprises the heavy chain variable region of the CNTO95 antibody, having the amino acid sequence of SEQ ID NO: 4 (shown below). In one embodiment, one or more amino acid residues at positions 7, 9, 11, 14, 41, 74, 84, and 113 of this heavy chain variable region are substituted to comprise a neutral or positively charged amino acid residue.

CNT095 heavy chain variable region (C95H22)-
SEQ ID NO: 4
QVQLVESGGGVVQPGRSRRLSCAASGFTFSRYTMEIWVRQAPGKGLEWVA
VISFDGSNKYYVDSVKGRFTISRDNSENTLYLQVNILRAEDTAVYYCARE
ARGSYAFDIWGQGTMVTVSS Another exemplary bi-specific antibody disclosed herein is an antibody that binds TIM3 (CD366) and PD-1 (CD279). This antibody has a first polypeptide comprising a heavy chain (TM3H24) having a variable region that, together with its light chain, bind TIM3. In one embodiment, the isoelectric point of this first heavy chain polypeptide is less than the isoelectric point of the second heavy chain polypeptide of the antibody, which, together with its light chain, bind PD-1. In accordance with this embodiment, this heavy chain variable region of comprises the amino acid sequence of SEQ ID NO: 2, where the residue at position 75 (corresponding to Kabat residue 74) is a negatively charged amino acid residue, such as an aspartic acid residue (TM3H24 S75D). Alternatively, the heavy chain variable region comprises the amino acid sequence of SEQ ID NO: 2, where the amino acid residue at position 84 (corresponding to Kabat residue 82a) is a negatively charged amino acid residue, such as an aspartic acid residue (TM3H24 N84D). In yet another embodiment, the heavy chain variable region comprises the amino acid sequence of SEQ ID NO: 2, where the amino acid residue at position 88 (corresponding to Kabat residue 84) is a negatively charged amino acid residue, such as an aspartic acid residue (TM3H24 A88D).

Alternatively, the second polypeptide comprising a heavy chain having a variable region (PD1H170), which, together with its light chain, bind PD-1, is modified to lower its pI relative to the pI of the TM3H24 heavy chain, and the over pI of the bispecific antibody. In accordance with this embodiment, the PD1H170 heavy chain variable region comprises the amino acid sequence of SEQ ID NO: 3, where the residue at position 75 (corresponding to Kabat residue 74) is a negatively charged amino acid residue, such as an aspartic acid residue (PD1H170 S75D). Alternatively, the heavy chain variable region comprises the amino acid sequence of SEQ ID NO: 3, where the amino acid residue at position 84 (corresponding to Kabat residue 82a) is a negatively charged amino acid residue, such as an aspartic acid residue (PD1H170 S84D). In yet another embodiment, the heavy chain variable region comprises the amino acid sequence of SEQ ID NO: 3, where the amino acid residue at position 88 (corresponding to Kabat residue 84) is a negatively charged amino acid residue, such as an aspartic acid residue (PD1H170 S88D).

Another aspect of the present disclosure is directed to a multi-specific antibody that includes a first polypeptide comprising a heavy chain variable region and a second polypeptide comprising a heavy chain variable region, wherein the isoelectric point of the first polypeptide is higher than the isoelectric point of the second polypeptide as a result of one or more amino acid residues at positions 7, 9, 11, 14, 41, 74, 84, and 113 (Kabat numbering) of the heavy chain variable region of the first polypeptide comprising a neutral or positively charged amino acid residue, and one or more amino acid residues at the corresponding positions of the heavy chain variable region of the second polypeptide comprise a differentially charged amino acid residue (i.e., a negatively or neutrally charged amino acid residue, respectively) when compared to the first polypeptide.

In one embodiment, the one or more amino acid residues at positions 9, 70, 74, 82a, and 84 (Kabat numbering) of the heavy chain variable region of the second polypeptide comprise a neutral or negatively charged amino acid residue, and one or more amino acid residues at the corresponding positions of the heavy chain variable region of the first polypeptide comprise a differentially charged amino acid residue (i.e., a negatively or neutrally charged residue, respectively) when compared to the first polypeptide.

In one embodiment, the neutral or positively charged amino acid residues at the one or more positions of 7, 9, 11, 14, 41, 74, 84, and 113 of the first heavy chain polypeptide are introduced into the first polypeptide by way of amino acid substitution. Likewise, the one or more neutral or negatively charged amino acid residues in the second heavy chain polypeptide are introduced into the second polypeptide by way of amino acid substitution.

The invention also provides an anti-TIM3 antibody comprising a heavy chain variable region (VH) of SEQ ID NOs: 6, 7 or 8 and a light chain variable region (VL) of SEQ ID NO: 5. The invention also provides an anti-TIM3 antibody comprising the $V_H$ of SEQ ID NO: 6 and the VL of SEQ ID NO: 5. The invention also provides an anti-TIM3 antibody comprising the $V_H$ of SEQ ID NO: 7 and the VL of SEQ ID NO: 5. The invention also provides an anti-TIM3 antibody comprising the $V_H$ of SEQ ID NO: 8 and the VL of SEQ ID NO: 5.

The invention also provides an anti-PD-1 antibody comprising a heavy chain variable region (VH) of SEQ ID NO: 10, 11 or 12 and a light chain variable region (VL) of SEQ ID NO: 9. The invention also provides an anti-PD-1 antibody comprising a heavy chain variable region (VH) of SEQ ID NO: 10 and a light chain variable region (VL) of SEQ ID NO: 9. The invention also provides an anti-PD-1 antibody comprising a heavy chain variable region (VH) of SEQ ID NO: 11 and a light chain variable region (VL) of SEQ ID NO: 9. The invention also provides an anti-PD-1 antibody comprising a heavy chain variable region (VH) of SEQ ID NO: 12 and a light chain variable region (VL) of SEQ ID NO: 9.

The invention also provides a bispecific PD1×TIM3 antibody comprising a first domain that binds PD-1 and a second domain that binds TIM3, wherein the first domain comprises a $V_H$ of SEQ ID NOs: 10, 11 or 12 and a VL of SEQ ID NO: 9, and the second domain comprises the $V_H$ of SEQ ID NOs: 6, 7 or 8 and the VL of SEQ ID NO: 5.

In some embodiments, the anti-PD-1, the anti-TIM3 or the bispecific PD-1×TIM3 antibodies are an IgG1 isotype. In some embodiments, the anti-PD-1, the anti-TIM3 or the bispecific PD-1×TIM3 antibodies are an IgG2 isotype. In some embodiments, the anti-PD-1, the anti-TIM3 or the bispecific PD-1×TIM3 antibodies are an IgG3 isotype. In some embodiments, the anti-PD-1, the anti-TIM3 or the bispecific PD-1×TIM3 antibodies are an IgG4 isotype.

In some embodiments, the antibody provided herein comprises at least one mutation in an antibody Fc that modulates antibody binding to an Fc receptor (FcR). In some embodiments, the FcR is FcγRI, FcγRIIa, FcγRIIb, FcγRIII or FcRn. In some embodiments, the antibody provided herein comprises a S228P mutation.

An exemplary IgG4 constant domain is show in SEQ ID NO: 13 (IgG4 with S228P mutation).

SEQ ID NO: 13
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

-continued

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

The bispecific PD-1/TIM3 antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Int. Patent Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. Substitutions that may be used are F405L in one heavy chain and K409R in the other heavy chain in IgG1 antibodies. In IgG4 antibodies, one wild-type heavy chain and F405L/R409K mutation in the other heavy chain may be used. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl) phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

In some embodiments, the anti-PD-1, the anti-TIM3 and the bispecific PD-1×TIM3 antibodies are antagonistic antibodies. A typical biological activity induced by the antagonistic antibodies provided herein is activation of antigen-specific CD4⁻ or CD8⁺ T cells. Various readouts may be used to assess the antagonistic nature of the antibodies provided herein, such as enhanced proliferation or enhanced production of interferon-γ (IFN-γ), IL-17 IL-2, IL-6, IL-22, IL-23 or GM-CSF by antigen-specific CD4⁺ or CD8⁺ T cells. In an exemplary assay, the effect of antibodies on T cells from normal donor that are stimulated by allogeneic dendritic cells or specific antigens, such as Tetanus toxoid or CMV are used. In this setting, changes in T cell function with antibody treatment can be detected by measuring supernatant cytokine levels or markers of T cell activation. In an exemplary assay, PBMCs determined to be reactive to CMV antigens are used as source of antigen-specific CD4⁻ or CD8⁺ T cells. $1.5 \times 10^6$ cells/ml or $2 \times 10^6$ cells/ml of CMV-reactive PBMCs are plated onto culture plates and 0.1-0.2 µg/ml CMV peptides added to cultures. CMV peptides may be purchased for example from JPT Technologies. Test antibodies are added at singe dose of 10 µg/ml, plates incubated for 6 days, and cell proliferation assessed by addition of 1 µCi/well methyl-3H-thymidine (PerkinElmer) for 6 hours and radioactivity measured in each sample. Alternatively, cytokine production by cells is measured using ELISA or known multiplex assays. "Antagonist" or "antagonistic" refers to an antibody which upon binding to PD-1, TIM-3 or both suppresses at least one biological activity that is mediated by PD-1 and/or TIM-3 ligand. The antibody is an antagonist when the at least one biological activity is suppressed by at least about 20%, 30%, 40%, 45%, 50%, 55%, 60%, 65%, 70%, 75%, 80%, 85%, 90%, 95%, or 100% greater than in the absence of the antagonist (e.g., negative control), or when the suppression is statistically significant when compared to the suppression in the absence of the antagonist. An exemplary TIM-3 ligand is galectin-9. PD-L1 is a ligand for PD-1.

The invention also provides a pharmaceutical composition comprising the anti-PD-1, the anti-TIM3 and the bispecific PD-1×TIM3 antibodies of the invention and a pharmaceutically acceptable carrier. For therapeutic use, the antibodies of the invention may be prepared as pharmaceutical compositions containing an effective amount of the antibodies as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies or the antigen-binding fragments thereof of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The antibodies of the invention have in vitro and in vivo diagnostic, as well as therapeutic and prophylactic utilities. For example, the antibodies of the invention may be administered to cells in culture, in vitro or ex vivo, or to a subject to treat, prevent, and/or diagnose a variety of disorders, such as cancers and infectious disorders.

The invention provides a method of enhancing an immune response in a subject, comprising administering to the subject the antibody or the antigen binding fragment thereof of the invention for a time sufficient to modify the immune response.

"Immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

"Enhance" or "enhancing" or "upmodulate" or "upmodulating" refers to a detectable increase in the level of an immune response in a subject compared with the level of a response in the subject in the absence of a treatment or compound, and/or compared with the level of a response in an otherwise identical but untreated subject.

In some embodiments, the subject is a human patient.

The antibodies of the invention are suitable for treating a subject having a disorder that may be treated by augmenting immune responses, such as T-cell mediated immune responses.

In some embodiments, the subject has cancer or a viral infection.

The invention also provides a method of treating cancer comprising administering to the subject in need thereof a therapeutically effective amount of the isolated antibody or the antigen binding fragment provided herein for a time sufficient to treat cancer.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Therapeutically effective amount" refers to an amount effective, at dosages and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

Cancer may be a hyperproliferative condition or disorder, a solid tumor, a hematological malignancy, a soft tissue tumor, or a metastatic lesion.

"Cancer" is meant to include all types of cancerous growths or oncogenic processes, metastatic tissues or malignantly transformed cells, tissues, or organs, irrespective of histopathology type or stage of invasiveness. Examples of cancers include solid tumors, hematological malignancies, soft tissue tumors, and metastatic lesions. Exemplary solid tumors include malignancies, e.g., sarcomas, and carcinomas (including adenocarcinomas and squamous cell carcinomas) of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, a rectal cancer, a renal-cell carcinoma, a liver cancer, a non-small cell carcinoma of the lung, a cancer of the small intestine and a cancer of the esophagus. Squamous cell carcinomas include malignancies, e.g., in the lung, esophagus, skin, head and neck region, oral cavity, anus, and cervix.

In some embodiments, cancer is a melanoma.

Metastatic lesions of cancers may also be treated or prevented using the methods and antibodies of the invention described herein.

Exemplary cancers whose growth may be inhibited or reduced using the antibodies of the invention include cancers that may be responsive to immunotherapy. Exemplary such cancers include a melanoma, a renal cancer, a prostate cancer, a breast cancer, a colon cancer, a gastrointestinal cancer, a stomach cancer, an esophageal cancer, a lung cancer, a metastatic malignant melanoma, a clear cell carcinoma, a hormone refractory prostate adenocarcinoma, a non-small cell lung cancer or cancer of the head and neck. Refractory or recurrent malignancies may be treated using the antibodies of the invention described herein.

Exemplary other cancers that may be treated with the antibodies of the invention ae an anal cancer, a basal cell carcinoma, a biliary tract cancer, a bladder cancer, a bone cancer, brain and CNS cancers, a carcinoma of the fallopian tubes, carcinoma of the vagina, a carcinoma of the vulva, a cutaneous or intraocular malignant melanoma, a astro-esophageal cancer, a testicular cancer, an ovarian cancer, a pancreatic cancer, a rectal cancer, an uterine cancer, a primary CNS lymphoma; a neoplasm of the central nervous system (CNS), a cervical cancer, a choriocarcinoma, a rectum cancer, a connective tissue cancer, a cancer of the digestive system, an endometrial cancer, an eye cancer; an intra-epithelial neoplasm, a kidney cancer, a larynx cancer, a liver cancer; a small cell lung cancer, a neuroblastoma, an oral cavity cancer (e.g., lip, tongue, mouth, and pharynx), a nasopharyngeal cancer, a retinoblastoma, a rhabdomyosarcoma, a cancer of the respiratory system, a sarcoma, a thyroid cancer, a cancer of the urinary system, a hepatocarcinoma, a cancer of the anal region, a carcinoma of the fallopian tubes, a carcinoma of the vagina, a carcinoma of the vulva, a cancer of the small intestine, a cancer of the endocrine system, a cancer of the parathyroid gland, a cancer of the adrenal gland, a sarcoma of soft tissue, a cancer of the urethra, a cancer of the penis, solid tumors of childhood, a tumor angiogenesis, a spinal axis tumor, a brain stem glioma, a pituitary adenoma, Kaposi's sarcoma, Merkel cell cancer, an epidermoid cancer, a squamous cell cancer, an environmentally induced cancers including those induced by asbestos, as well as other carcinomas and sarcomas, and combinations of said cancers.

Exemplary hematological malignancies that may be treated with the antibodies of the invention include leukemias, lymphomas and myeloma, such as a precursor B-cell lymphoblastic leukemia/lymphoma and a B-cell non-Hodgkin's lymphoma, an acute promyelocytic leukemia, an acute lymphoblastic leukemia (ALL), a B-cell chronic lymphocytic leukemia (CLL)/small lymphocytic lymphoma (SLL), a B-cell acute lymphocytic leukemia, a B-cell prolymphocytic leukemia, a lymphoplasmacytic lymphoma, a mantle cell lymphoma (MCL), a follicular lymphoma (FL), including low-grade, intermediate-grade and high-grade FL, a cutaneous follicle center lymphoma, a marginal zone B-cell lymphoma (MALT type, nodal and splenic type), a hairy cell leukemia, a diffuse large B-cell lymphoma (DLBCL), Burkitt's lymphoma (BL), a plasmacytoma, a multiple myeloma (MM), a plasma cell leukemia, a post-transplant lymphoproliferative disorder, Waldenstrom's macroglobulinemia, plasma cell disorders, an anaplastic large-cell lymphoma (ALCL), a T-cell acute lymphocytic leukemia, a primary systemic amyloidosis (e.g. light chain amyloidosis), a pro-lymphocytic/myelocytic leukemia, an acute myeloid leukemia (AML), a chronic myeloid leukemia (CML), a large granular lymphocytic (LGL) leukemia, a NK-cell leukemia and Hodgkin's lymphoma.

"Plasma cell disorder" refers to disorders characterized by clonal plasma cells, and includes a multiple myeloma, a light chain amyloidosis and Waldenstrom's macroglobulinemia. Light chain amyloidosis and Waldenstrom's macroglobulinemia can arise independently from multiple myeloma.

They may also present simultaneously with multiple myeloma, and develop either before or after the development of multiple myeloma.

Exemplary B-cell non-Hodgkin's lymphomas are a lymphomatoid granulomatosis, a primary effusion lymphoma, an intravascular large B-cell lymphoma, a mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

Patients having cancer including metastatic cancer that express PD-L1 may be treated with the antibodies of the invention. The cancer may be a melanoma, a renal cell carcinoma, a squamous non-small cell lung cancer (NSCLC), a non-squamous NSCLC, a colorectal cancer, a castration-resistant prostate cancer, an ovarian cancer, a gastric cancer, an adenocarcinoma (ACA), a squamous cell carcinoma (SCC), a hepatocellular carcinoma (HCC), a pancreatic carcinoma, a squamous cell carcinoma of the head and neck, carcinomas of the esophagus, gastrointestinal tract and breast.

In some embodiments, the subject has a tumor that expresses PD-L1.

In some embodiments, the subject is refractory and/or relapsed after treatment with the PD-L1 antibody. in some embodiments, the PD-L1 antibody is avelumab, durvalumab or atezolizumab. Various qualitative and/or quantitative methods may be used to determine relapse or refractory nature of the disease. Symptoms that may be associated with relapse or resistance are, for example, a decline or plateau of the well-being of the patient or re-establishment or worsening of various symptoms associated with solid tumors, and/or the spread of cancerous cells in the body from one location to other organs, tissues or cells.

The invention also provides a method of treating a viral infection comprising administering to the subject in need thereof a therapeutically effective amount of the isolated antibody or the antigen binding fragment provided herein for a time sufficient to treat viral infection.

Exemplary viral infections that may be treatable by the antibodies of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

Embodiment 1. An anti-TIM3 antibody comprising a heavy chain variable region (VH) of SEQ ID NOs: 6, 7 or 8 and a light chain variable region (VL) of SEQ ID NO: 5.

Embodiment 2. An anti-TIM3 antibody comprising the $V_H$ of SEQ ID NO: 6 and the VL of SEQ ID NO: 5.

Embodiment 3. An anti-TIM3 antibody comprising the $V_H$ of SEQ ID NO: 7 and the VL of SEQ ID NO: 5.

Embodiment 4. An anti-TIM3 antibody comprising the $V_H$ of SEQ ID NO: 8 and the VL of SEQ ID NO: 5.

Embodiment 5. An anti-PD-1 antibody comprising the $V_H$ of SEQ ID NO: 10, 11 or 12 and the VL of SEQ ID NO: 9.

Embodiment 6. An anti-PD-1 antibody comprising the $V_H$ of SEQ ID NO: 10 and the VL of SEQ ID NO: 9.

Embodiment 9. An anti-PD-1 antibody comprising the $V_H$ of SEQ ID NO: 11 and the VL of SEQ ID NO: 9.

Embodiment 10. An anti-PD-1 antibody comprising the $V_H$ of SEQ ID NO: 12 and the VL of SEQ ID NO: 9.

Embodiment 11. A bispecific PD-1×TIM3 antibody comprising a first domain that binds PD-1 and a second domain that binds TIM3, wherein the first domain comprises the $V_H$ of SEQ ID NOs: 10, 11 or 12 and the VL of SEQ ID NO: 9, and the second domain comprises the $V_H$ of SEQ ID NOs: 6, 7 or 8 and the VL of SEQ ID NO: 5.

Embodiment 12. The bispecific PD-1×TIM3 antibody according to Embodiment 11, wherein the first domain comprises the $V_H$ of SEQ ID NO: 10 and the VL of SEQ ID NO: 9 and the second domain comprises the $V_H$ of SEQ ID NO: 6 and the VL of SEQ ID NO: 5.

Embodiment 13. The bispecific PD-1×TIM3 antibody according to Embodiment 11, wherein the first domain comprises the $V_H$ of SEQ ID NO: 11 and the VL of SEQ ID NO: 9 and the second domain comprises the $V_H$ of SEQ ID NO: 6 and the VL of SEQ ID NO: 5.

Embodiment 14. The bispecific PD-1×TIM3 antibody according to Embodiment 11, wherein the first domain comprises the $V_H$ of SEQ ID NO: 12 and the VL of SEQ ID NO: 9 and the second domain comprises the $V_H$ of SEQ ID NO: 6 and the VL of SEQ ID NO: 5.

Embodiment 15. The bispecific PD-1×TIM3 antibody according to Embodiment 11, wherein the first domain comprises the $V_H$ of SEQ ID NO: 10 and the VL of SEQ ID NO: 9 and the second domain comprises the $V_H$ of SEQ ID NO: 7 and the VL of SEQ ID NO: 5.

Embodiment 16. The bispecific PD-1×TIM3 antibody according to Embodiment 11, wherein the first domain comprises the $V_H$ of SEQ ID NO: 11 and the VL of SEQ ID NO: 9 and the second domain comprises the $V_H$ of SEQ ID NO: 7 and the VL of SEQ ID NO: 5.

Embodiment 17. The bispecific PD-1×TIM3 antibody according to Embodiment 11, wherein the first domain comprises the $V_H$ of SEQ ID NO: 12 and the VL of SEQ ID NO: 9 and the second domain comprises the $V_H$ of SEQ ID NO: 7 and the VL of SEQ ID NO: 5.

Embodiment 18. The bispecific PD-1×TIM3 antibody according to Embodiment 11, wherein the first domain comprises the $V_H$ of SEQ ID NO: 10 and the VL of SEQ ID NO: 9 and the second domain comprises the $V_H$ of SEQ ID NO: 8 and the VL of SEQ ID NO: 5.

Embodiment 19. The bispecific PD-1×TIM3 antibody according to Embodiment 11, wherein the first domain comprises the $V_H$ of SEQ ID NO: 11 and the VL of SEQ ID NO: 9 and the second domain comprises the $V_H$ of SEQ ID NO: 8 and the VL of SEQ ID NO: 5.

Embodiment 20. The bispecific PD-1×TIM3 antibody according to Embodiment 11, wherein the first domain comprises the $V_H$ of SEQ ID NO: 12 and the VL of SEQ ID NO: 9 and the second domain comprises the $V_H$ of SEQ ID NO: 8 and the VL of SEQ ID NO: 5.

Embodiment 21. The antibody according to any one of Embodiments 1-20, wherein the antibody is an IgG4 isotype.

Embodiment 22. The antibody according to any one of Embodiments 1-21, comprising a S228P mutation when compared to the wild-type IgG4 of SEQ ID NO: 13.

Embodiment 23. The antibody according to any one of Embodiments 1-22, wherein the antibody is an antagonistic antibody.

Embodiment 24. A pharmaceutical composition comprising the antibody of any one of Embodiments 1-23.

Embodiment 25. The antibody of any one of Embodiments 1-23 or the pharmaceutical composition of Embodiment 24 for use in therapy.

Embodiment 24. The antibody of any one of Embodiments 1-23 or the pharmaceutical composition of Embodiment 24 for use in treating a subject having cancer.

Embodiment 25. The antibody or the pharmaceutical composition for use according to Embodiment 24, wherein cancer is a solid tumor or a hematological malignancy.

EXAMPLES

The following examples are provided to illustrate embodiments of the present invention but are by no means intended to limit its scope.

Example 1

Isoelectric Point Modification of Monoclonal and Bi-Specific Anti-TNFα Antibody

To identify amino acid residues within the surface of the variable region which could be substituted to increase or decrease surface charge, the CNTO148 antibody was employed. CNTO148 is a monoclonal antibody that binds TNFα. The antibody crystal structures are available. The isoelectric point of the CNTO148 antibody is ~9. Amino acid substitutions in the variable heavy region at positions 9, 70, 74, 82a, and 84 (Kabat numbering) (corresponding to amino acid positions 9, 71, 75, 84, and 88 of SEQ ID NO: 1) were initially tested to determine their ability to decrease the isoelectric point (pI) of the CNTO148 antibody. These substitutions were introduced either singly or in combination (see Example 4) via modification of the nucleic acid molecule encoding the heavy chain variable region. The variants were expressed using Expi293 cells.

TABLE 1

CNTO148 Antibody Variants

| Kabat position | Mutation | Surface exposure (%) | Location | Structure Comment |
|---|---|---|---|---|
| 9 | G9E | 29 | Opposite paratope | On surface |
| 70 | S71E | 22 | Side outside the paratope | On surface |
| 74 | S75D | 76 | Side outside the paratope | On surface |
| 82a | N84D | 31 | Opposite paratope | On surface |
| 84 | A88D | 29 | Opposite paratope | Protrudes in a pocket |

The variants were characterized using capillary isoelectric focusing (cIEF), capillary sodium dodecyl sulfate electrophoresis (cSDS) or sodium dodecyl sulfate-polyacrylamide gel electrophoresis (SDS-PAGE), and size exclusion high performance liquid chromatography (SE-HPLC). cIEF was done using the iCE3 analyzer from Protein Simple according to the manufacturer's protocol with either, pH 5-8 or pH 3-10, combined with pH 8-10.5 ampholytes. cSDS was done with the Lab Chip GXII from Caliper, using a Protein Express chip and the HT Protein Express Reagent Kit. SDS-PAGE was done using a Novex NuPAGE 1-12% Bis-Tris Gel, Invitrogen SeeBlue Plus2 Prestained Standard (1×), and 1×MES Running Buffer. SE-HPLC was done on a Waters Alliance using a TOSOH Bioscience Bioassist G35W, 7.8 mm ID, 30 cm column.

The variants were also characterized for changes in antigen binding. Antigen binding was measured using Maxisorp plates (Nunc) coated with F(ab')2 fragment donkey anti-human Fc from Jackson Immunoresearch and blocked with Superblock (Pierce). Serial dilutions of the variants were then added to the plate and allowed to bind. For measuring CNTO148 binding to TNF, biotinylated human TNF was added, followed by streptavidin-HRP (Jackson Immunoresearch), and bound TNF was detected using TMB substrate (Fitzgerald).

The temperature of unfolding ($T_m$) and temperature of aggregation onset ($T_{agg}$) of the samples were also analyzed using either the Activa Optim 2, or the updated UNCLE instrument. These instruments measure intrinsic fluorescence with increasing temperature as an indication of protein unfolding and light scattering with increasing temperature as an indication of aggregation onset. The temperature at which a protein begins to unfold or aggregate can indicate its structural stability. For this analysis, temperature steps from 20° C. to 85° C. at 0.3° C. per minute were used.

Results

Figure 1B:
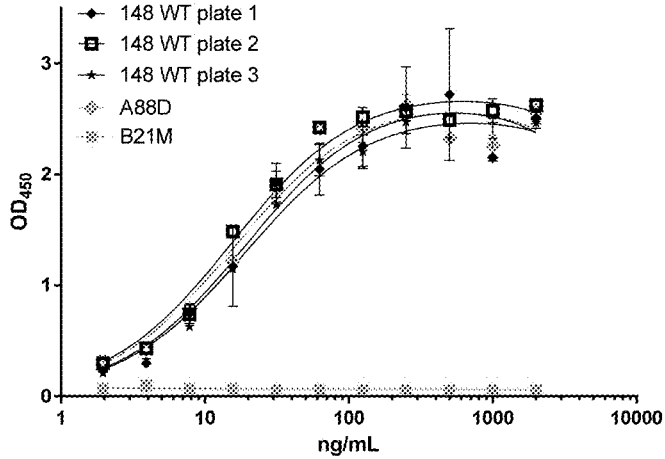
Figure 1C:
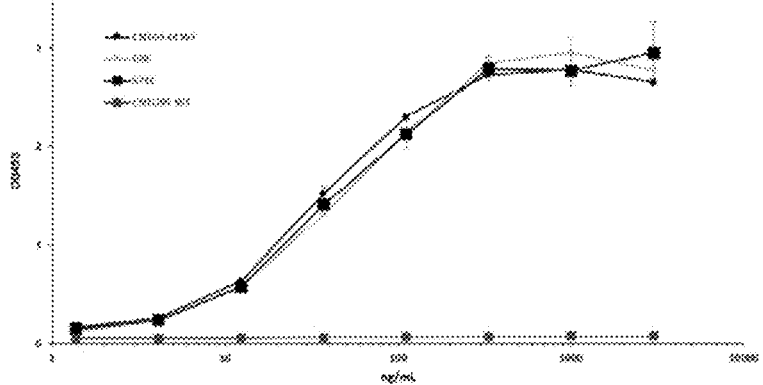
Figure 2A:
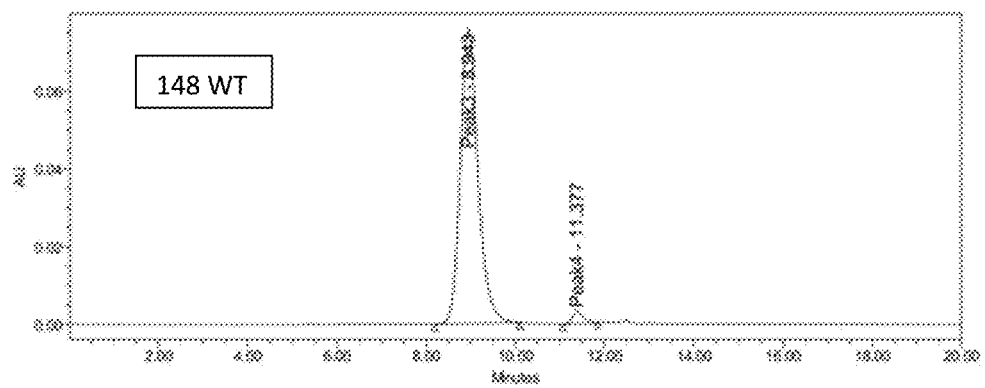
FIGS. 2A-2C shows analytical size exclusion high performance liquid chromatography (SE-HPLC) analysis of CNTO148 single substitution variants. In particular.
Figure 2B:
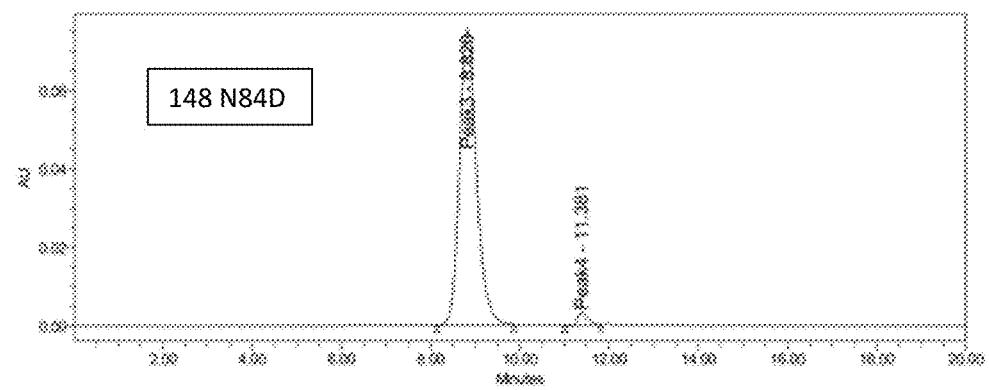
Figure 2C:
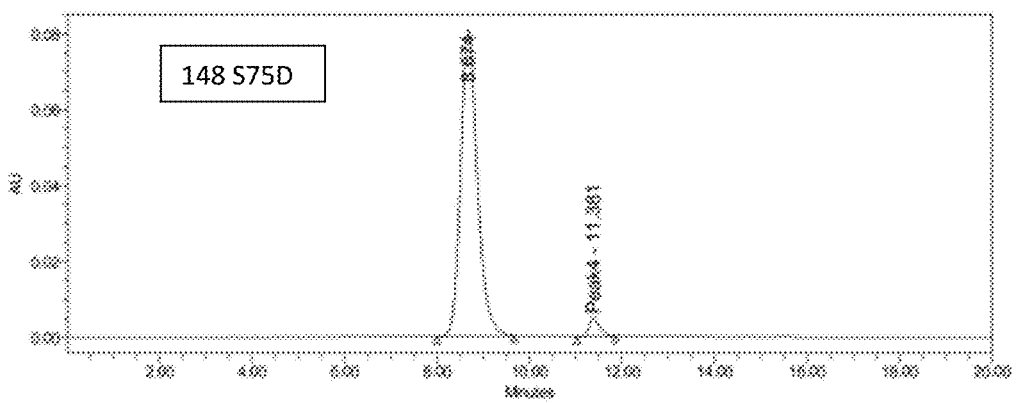
Figure 3A:
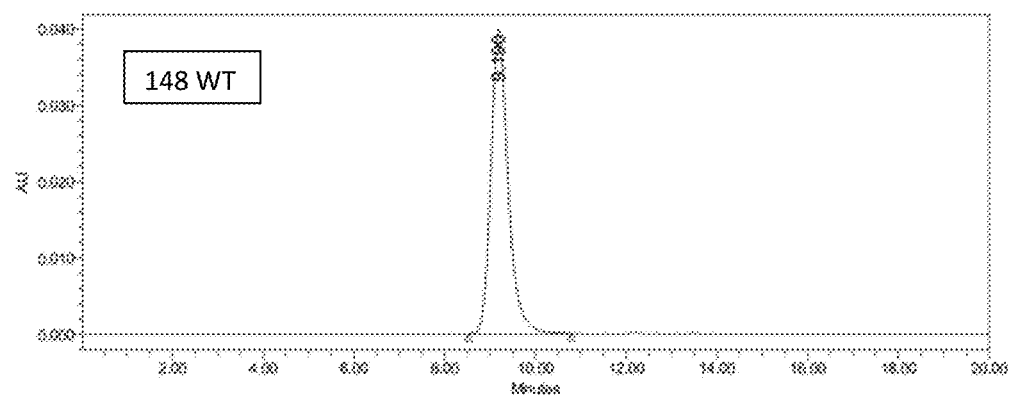
FIGS. 3A-3B shows analytical SE-HPLC analysis of CNTO148 wildtype and A88D variant. In particular.
Figure 3B:
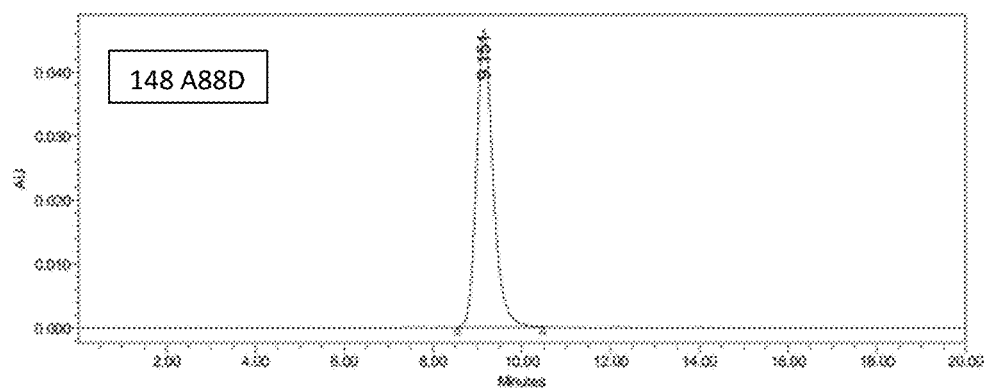
Figure 4A:
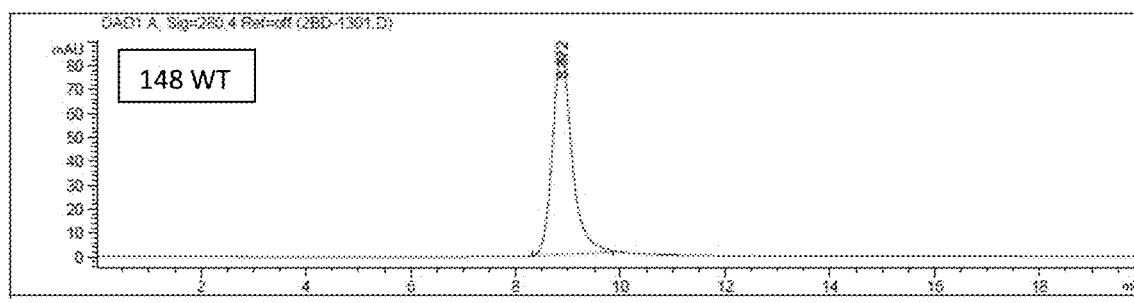
FIGS. 4A-4C shows analytical SE-HPLC analysis of CNTO148 wildtype, G9E, and S71E variants. In particular.
Figure 4B:
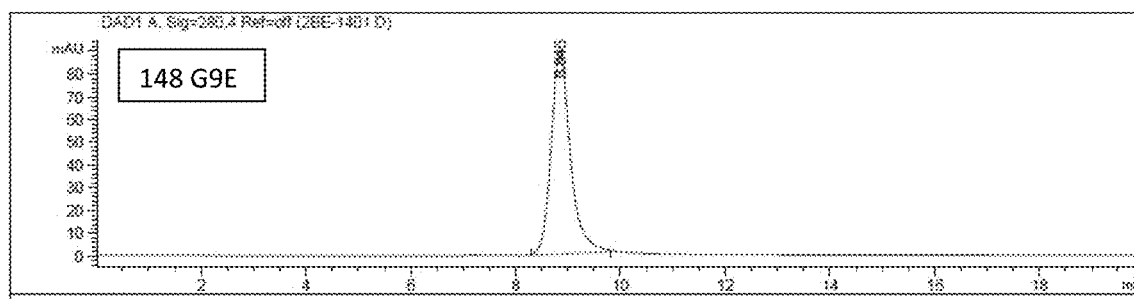
Figure 4C:
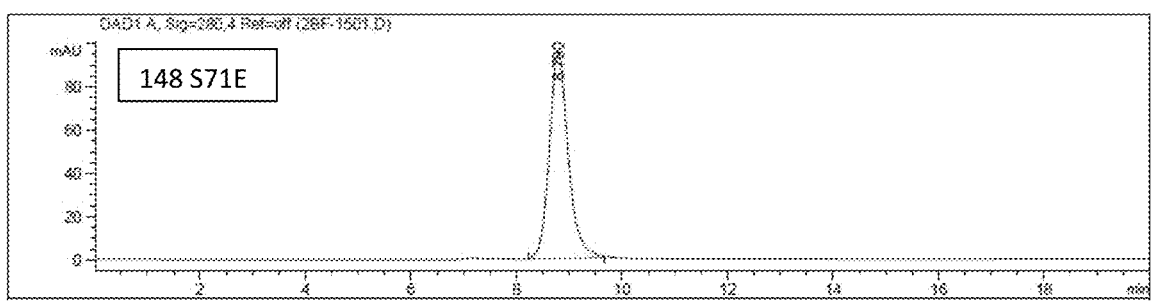

The characterization of CNTO148 variants is summarized in Table 2 below. The experimentally measured pIs of the CNTO148 S75D and N84D variants was 8.9 and 9.0, respectively, compared to the wildtype (WT) with a pI of 9.1. In a separate experiment the pI of the CNTO148 A88D variant was 9.1 compared to the WT with a pI of 9.2. In yet another experiment the pI of the CNTO148 G9E and S71E variants were 8.7 and 8.7 respectively, compared to the WT with a pI of 8.9. The differences in the pI of WT CNTO148 between experiments were likely due normal day-to-day variability and minor changes in the composition of electrolytes. The S75D, N84D, A88D, G9E, and S71E variants bound TNFα at least as well as the WT control FIG. 1A shows binding of the of S75D and N84D variants compared to wildtype (148 WT and CNTO148), FIG. 1B compares the A88D variant to wildtype CNTO148, and FIG. 1C compares the binding of the G9E and S71E variants, to WT CNTO148. CNTO95 was used a negative control. The variants also gave an SE-HPLC profile that was very similar to the WT. FIGS. 2A-2C show the SE-HPLC profiles for CNTO148 wildtype (FIG. 2A), N84D (FIG. 2B), and S75D (FIG. 2C), and FIGS. 3A-3B show a comparison of the SE-HPLC profiles for CNTO148 wildtype (FIG. 3A) and the A88D variant (FIG. 3B). FIGS. 4A-4C show a comparison of the SE-HPLC profiles for CNTO148 wildtype (FIG. 4A), G9E (FIG. 4B), and S71E (FIG. 4C).

TABLE 2

CNTO148 Variant Characterization Summary

| Kabat position | Mutation | Banding Pattern | % monomer | cIEF Charge Profile | Ag Binding | Stability (Tm and Tagg) |
|---|---|---|---|---|---|---|
| 9 | G9E | WT-like | WT-like | WT-like | WT-like | Decreased |
| 70 | S71E | WT-like | WT-like | WT-like | WT-like | WT-like |
| 74 | S75D | WT-like | WT-like | WT-like | WT-like | WT-like |
| 82a | N84D | WT-like | WT-like | WT-like | WT-like | WT-like |
| 84 | A88D | WT-like | WT-like | WT-like | WT-like | WT-like |

Figure 5A:
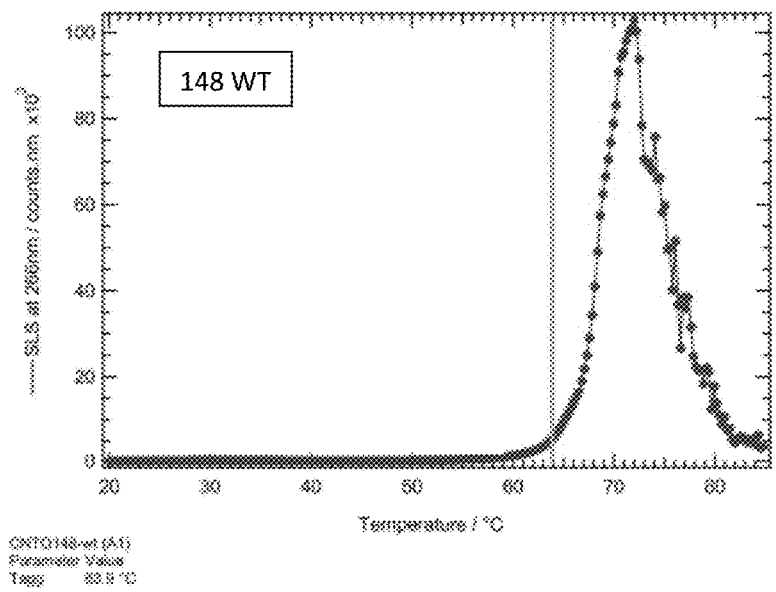
FIGS. 5A-5C are graphs showing onset of aggregation (colloidal stability) analysis of CNTO148 single substitution variants.
Figure 5B:
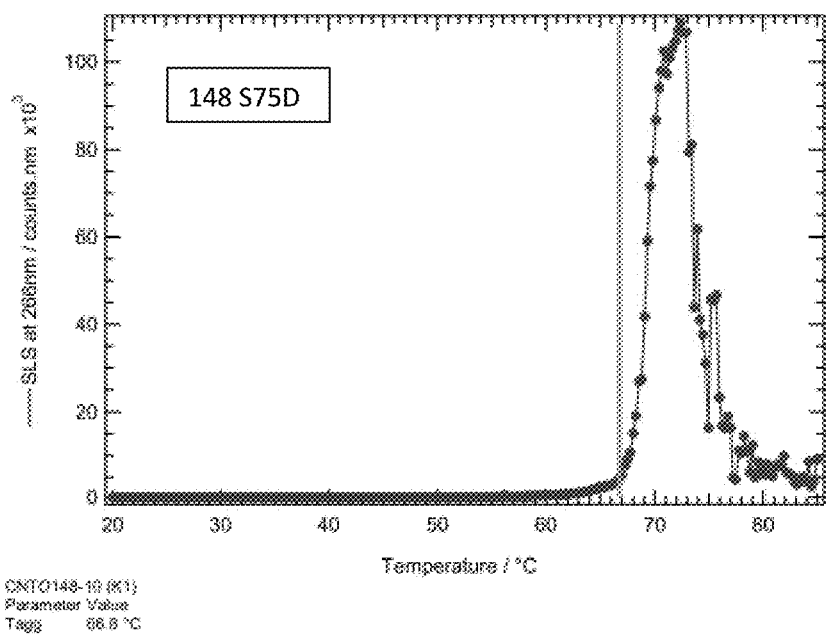
Figure 5C:
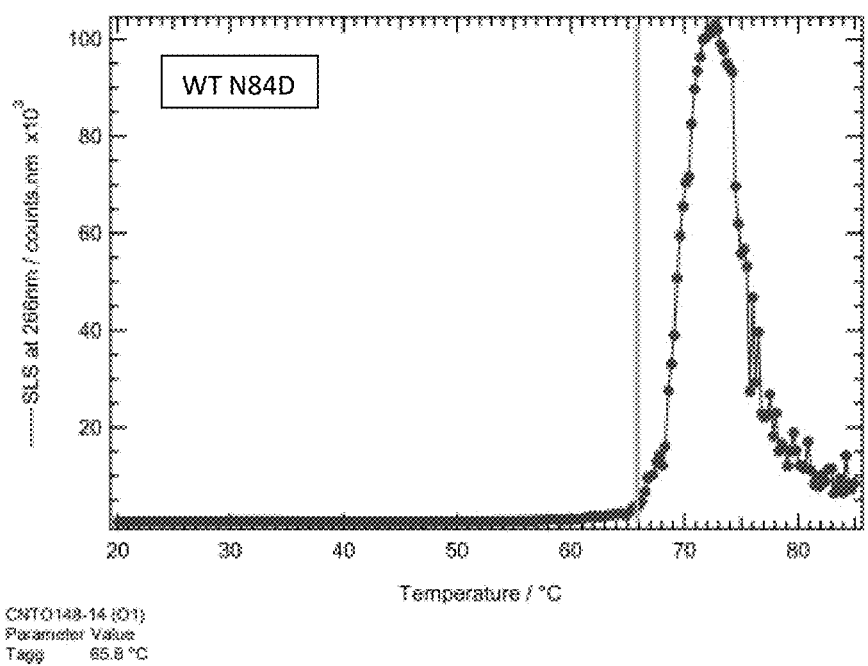
Figure 6A:
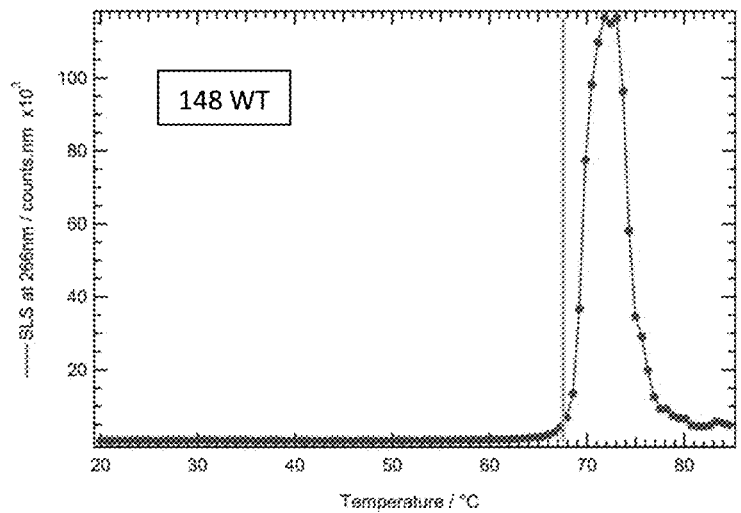
FIGS. 6A and 6B are graphs showing onset of aggregation (colloidal stability) analysis of CNTO148 wildtype and A88D variant.
Figure 6B:
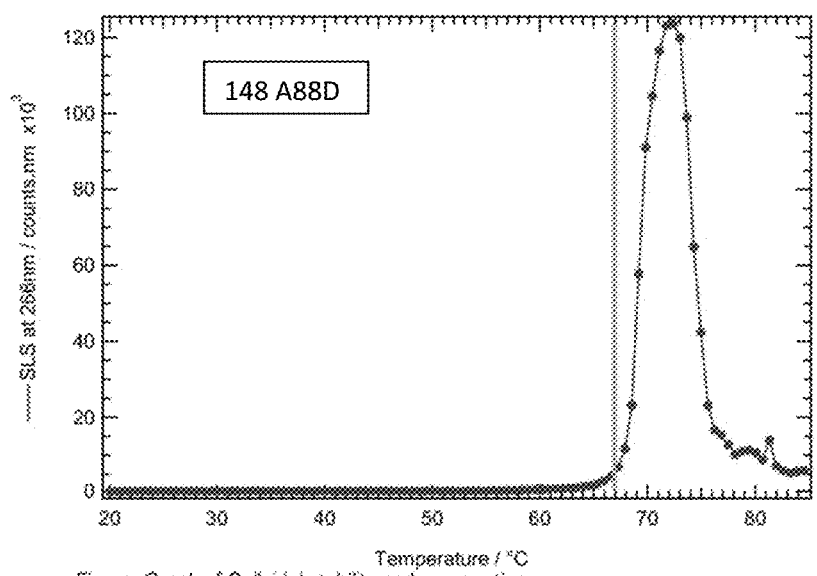
Figure 7A:
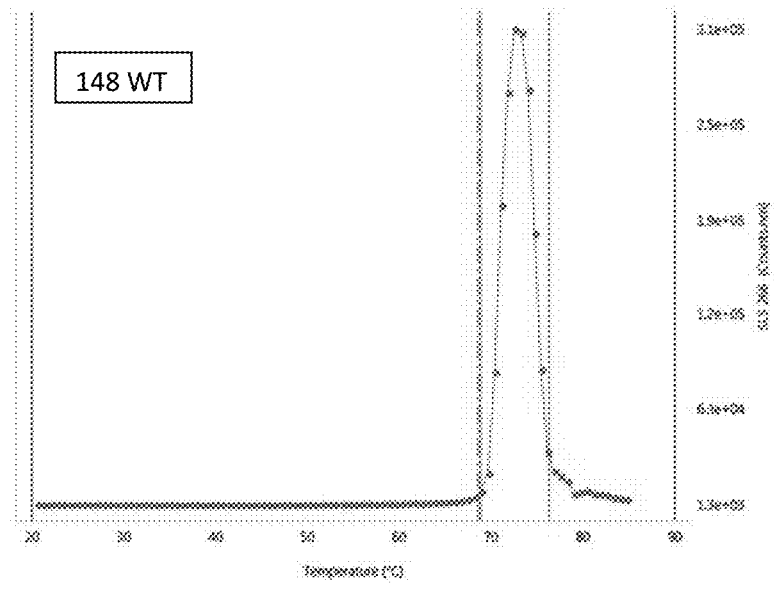
FIGS. 7A-7C are graphs showing onset of aggregation (colloidal stability) analysis of CNTO148 wildtype, G9E, and S71E variants.
Figure 7B:
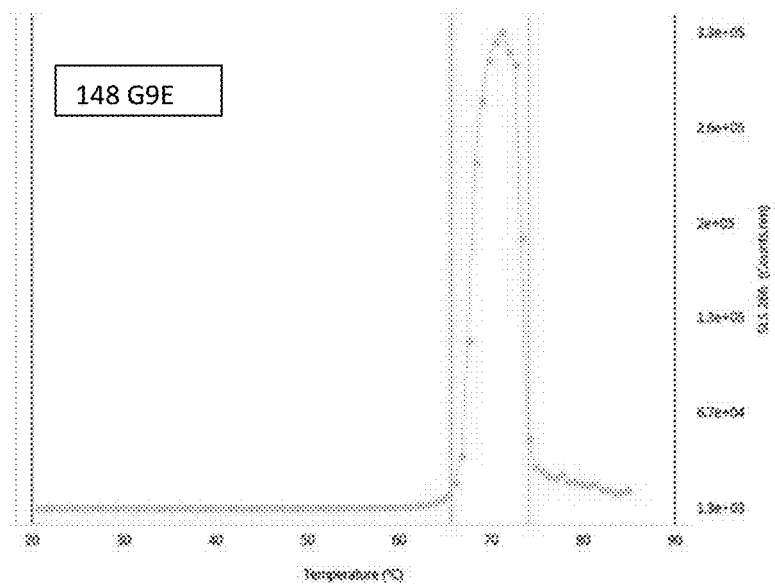
Figure 7C:
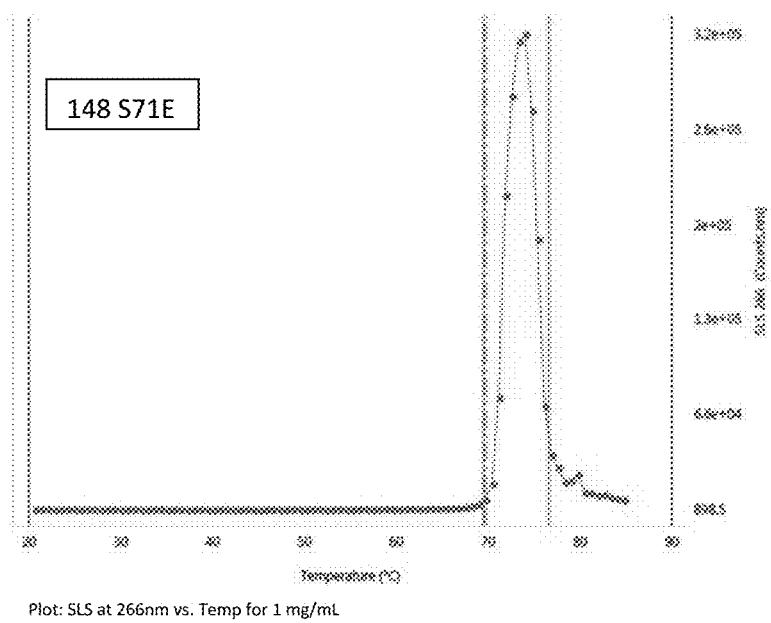

The temperature at onset of aggregation was measured as an indication of colloidal stability. The onset of aggregation ($T_{agg}$) for the S75D and N84D variants occurred at 66.8° C. and 65.8° C. (see FIGS. 5B and 5C, respectively), which was similar if not somewhat higher than the onset of aggregation for wildtype CNTO148 which occurred at 63.9° C. (see FIG. 5A) in this experiment. In a separate experiment the onset of aggregation for the A88D variant was found to occur at 66.9° C. (FIG. 6B), which was similar to the wildtype construct at 67.6° C. (FIG. 6A). In another experiment the onset of aggregation for the G9E and S71E variants was found to occur at 65.7° C. (FIG. 7B) and 69.5° C. (FIG. 7C) respectively, compared to the wildtype CNTO148 at 68.6° C. (FIG. 7A).

Figure 8A:
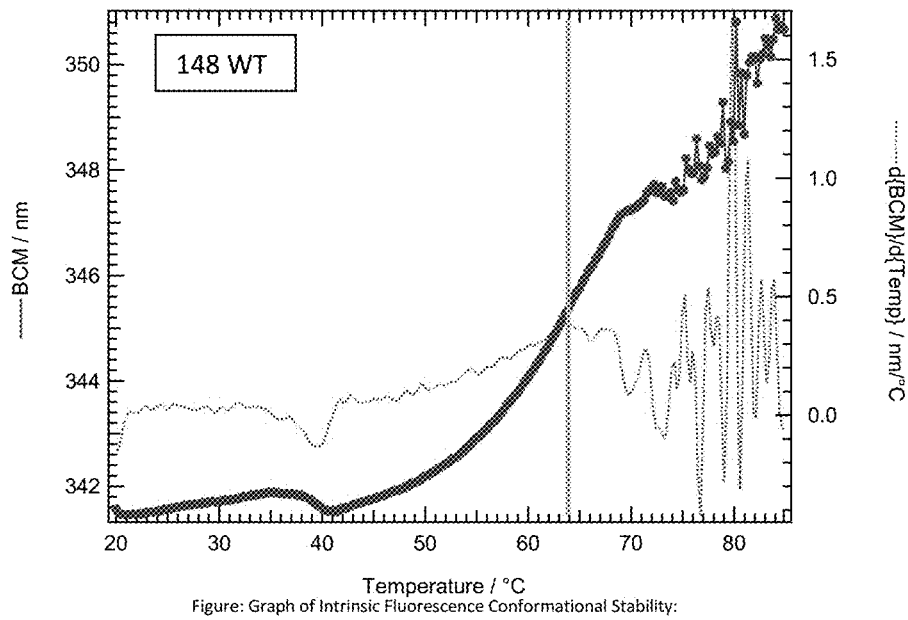
FIGS. 8A-8C are graphs showing temperature of unfolding (conformational stability) analysis of CNTO148 single substitution variants.
Figure 8B:
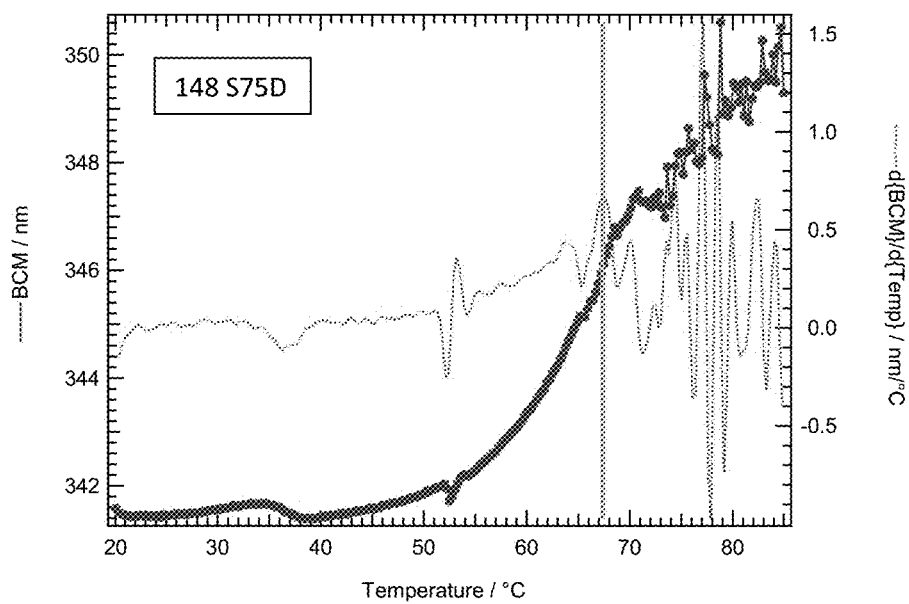
Figure 8C:
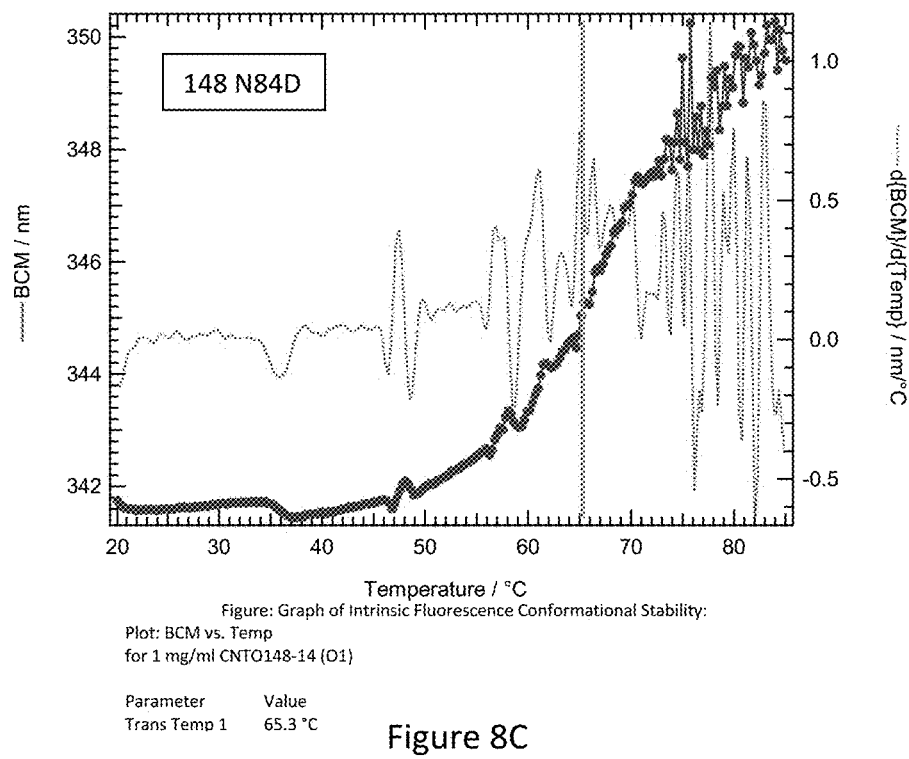
Figure 9A:
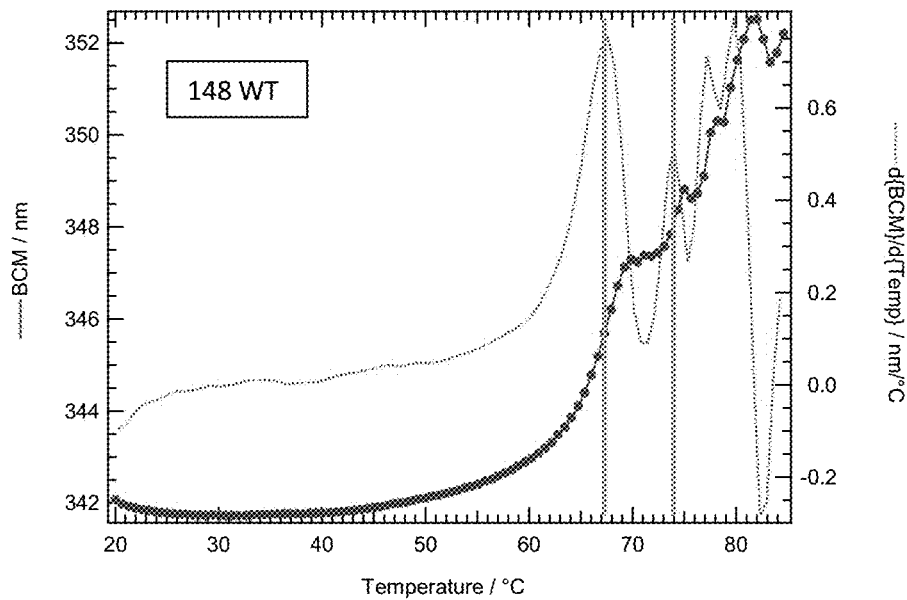
FIGS. 9A and 9B are graphs showing the temperature of unfolding (conformational stability) analysis of CNTO148 wildtype and A88D variant.
Figure 9B:
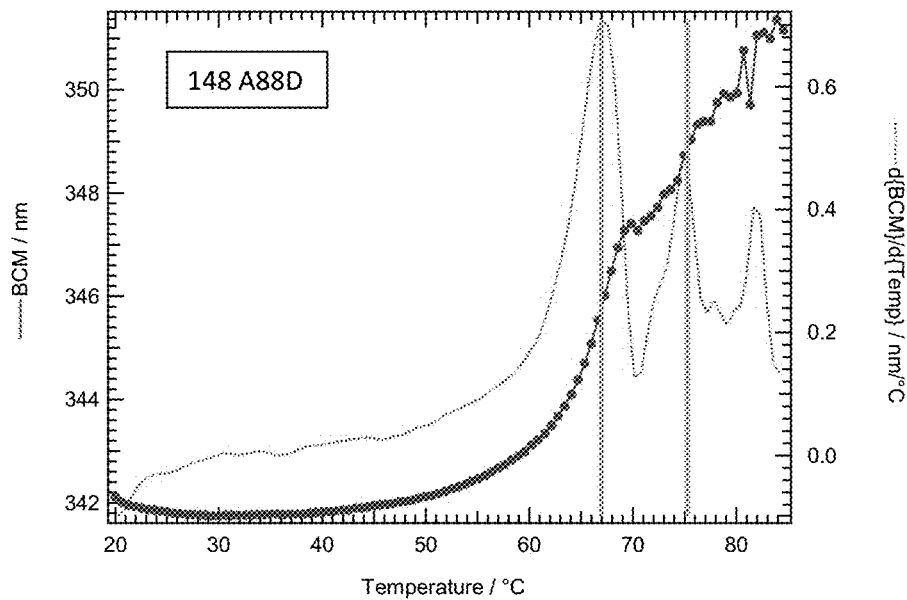
Figure 10A:
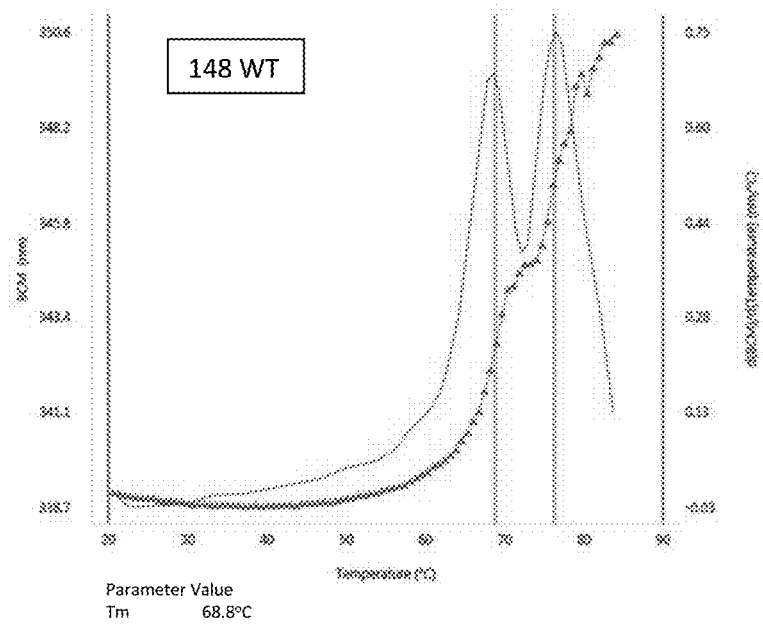
FIGS. 10A-10C are graphs showing the temperature of unfolding (conformational stability) analysis of CNTO148 wildtype, G9E, and S71E variants.
Figure 10B:
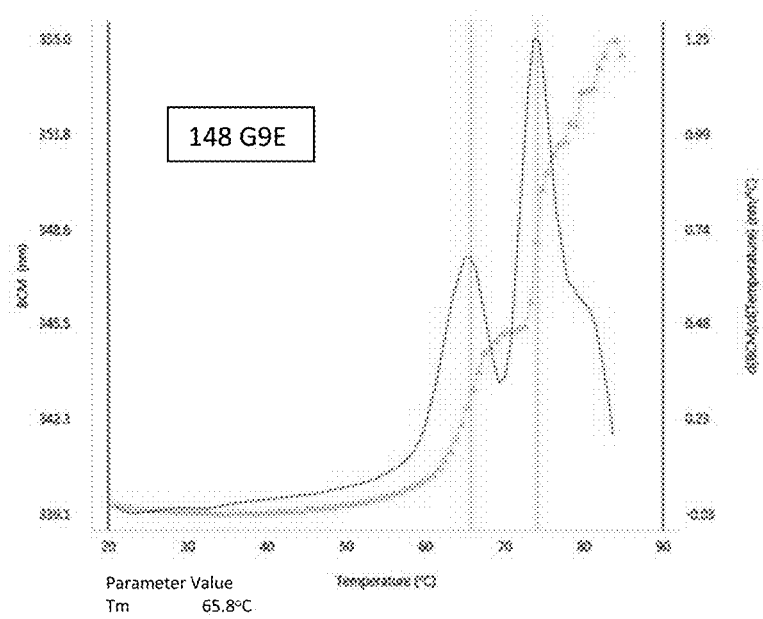
Figure 10C:
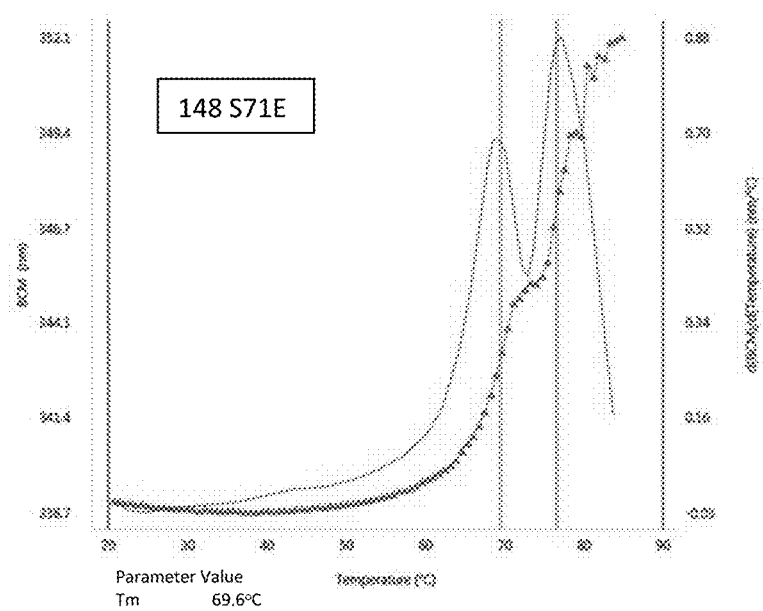

The temperature of unfolding was measured as an indication of conformational stability. The unfolding temperature ($T_{agg}$) of the S75D and N84D variants occurred at 67.3° C. (FIG. 8B) and 65.3° C. (FIG. 8C), respectively, which was similar to the unfolding temperature of the wildtype CNTO148 which occurred at 63.9° C. (FIG. 8A). In a separate experiment the unfolding temperature for the A88D variant occurred at 66.9° C. (FIG. 9B), which was similar to the wildtype construct in the experiment which occurred at 67.3° C. (FIG. 9A). In yet another experiment the unfolding temperature for the G9E and S71E variants were found to occur at 65.8° C. (FIG. 10B) and 69.6° C. (FIG. 10C) respectively, compared to the wildtype CNTO148 in this experiment which occurred at 68.8° C. (FIG. 10A). Variants that demonstrated a greater than 2° C. reduction in $T_m$ and $T_{agg}$ were regarded as having reduced stability. Of these variants, only the G9E variant demonstrated reduced binding compared to the WT; it had a lower Tm by 3° C. and a lower onset of aggregation by 2.9° C.

Example 2

Isoelectric Point Modification of Monoclonal and Bi-Specific Anti-αVβ3 Antibody

To identify amino acid residues within the surface of the variable region which could be substituted to increase or decrease surface charge, the CNTO95 antibody was employed. CNTO95 is a monoclonal antibody that binds αVβ33. The crystal structures are available. The isoelectric point of the CNTO95 antibody is ~9. Amino acid substitutions in the variable heavy region at positions 7, 9, 11, 14, 41, 74, 84, and 113 (Kabat numbering) (corresponding to amino acid positions 7, 9, 11, 14, 41, 71, 88, and 119 of SEQ ID NO: 4) were initially tested to determine their ability to decrease the isoelectric point (pI) of the CNTO95 antibody. These substitutions were introduced either singly or in combination via modification of the nucleic acid molecule encoding the heavy chain variable region. The variants were expressed using Expi293.

TABLE 3

CNTO95 Antibody Variants

| Kabat position | Mutation | Surface exposure (%) | Location | Structure Comment |
|---|---|---|---|---|
| 7 | S7R | 42 | Side outside the paratope | On surface |
| 9 | G9R | 41 | Side outside the paratope | On surface |
| 11 | V11R | 30 | Faces CH1 | On surface |
| 14 | P14R | 29 | On the bottom | On surface |
| 41 | P41R | 48 | Faces CH1 | On surface |
| 74 | S71K | 29 | Side outside the paratope | On surface |
| 84 | A88R | 52 | Faces CH1 | On surface |
| 113 | S119R | 58 | Part of V-CH1 elbow | On surface |

The variants were characterized using capillary isoelectric focusing (cIEF), sodium dodecyl sulfate-polyacrylamide gel electrophoresis (SDS-PAGE), and size exclusion high performance liquid chromatography (SE-HPLC). cIEF was done using the iCE3 analyzer from Protein Simple according to the manufacturer's protocol with pH 3-10 and pH 8-10.5 ampholytes. SDS-PAGE was done using a Novex NuPAGE 1-12% Bis-Tris Gel, Invitrogen SeeBlue Plus2 Prestained Standard (1×), and 1×MES Running Buffer. SE-HPLC was done on a Waters Alliance using a TOSOH Bioscience Bioassist G35W, 7.8 mm ID, 30 cm column.

The variants were also characterized for changes in antigen binding. Antigen binding was measured using Maxisorp plates (Nunc) coated with F(ab')2 fragment donkey anti-human Fc from Jackson Immunoresearch and blocked with Superblock (Pierce). Serial dilutions of the variants were then added to the plate and allowed to bind. For measuring CNTO95 binding to αVβ3, biotinylated human αVβ3 was added, followed by streptavidin-HRP (Jackson Immunoresearch), and bound αVβ3 was detected using TMB substrate (Fitzgerald).

The samples were also analyzed using the updated UNCLE instrument. This instrument measures intrinsic fluorescence with increasing temperature as an indication of protein unfolding and light scattering with increasing temperature as an indication of aggregation onset. The temperature at which a protein begins to unfold or aggregate can indicate its structural stability. For this analysis, temperature steps from 20° C. to 85° C. at 0.3° C. per minute were used.

Results

Figure 11:
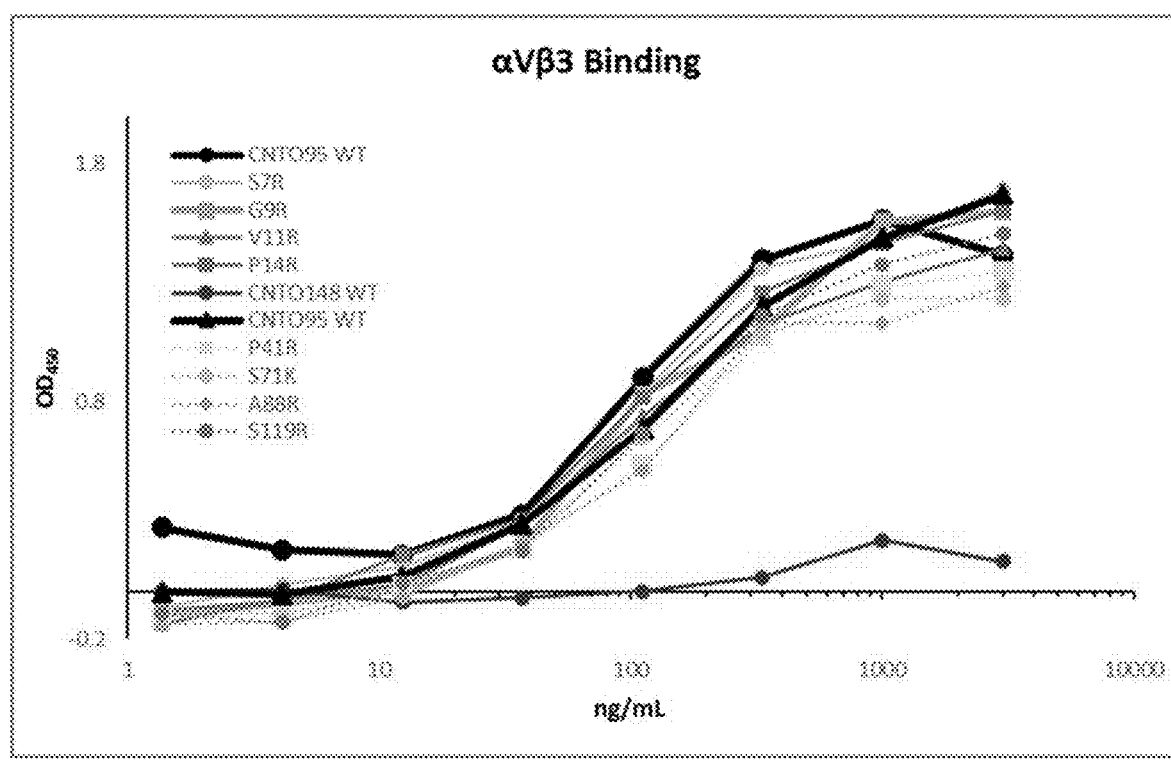
FIG. 11 is a graph of human αVβ3 binding ELISA of CNTO95 antibody single substitution variants.
Figure 12A:
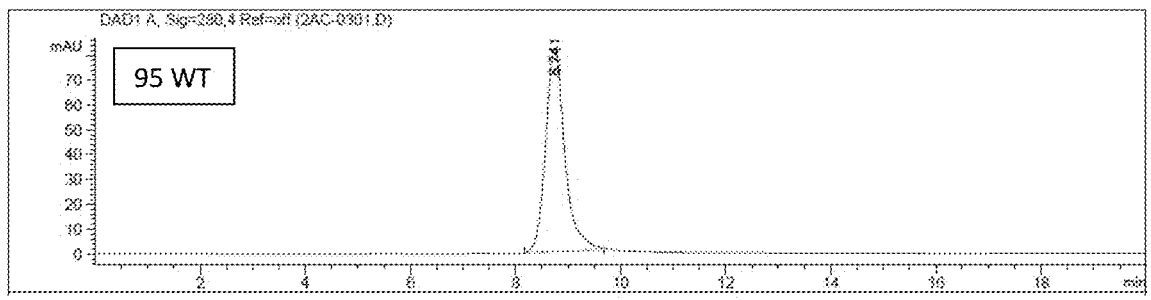
FIGS. 12A-12I shows analytical size exclusion high performance liquid chromatography (SE-HPLC) analysis of CNTO95 single substitution variants. In particular.
Figure 12B:
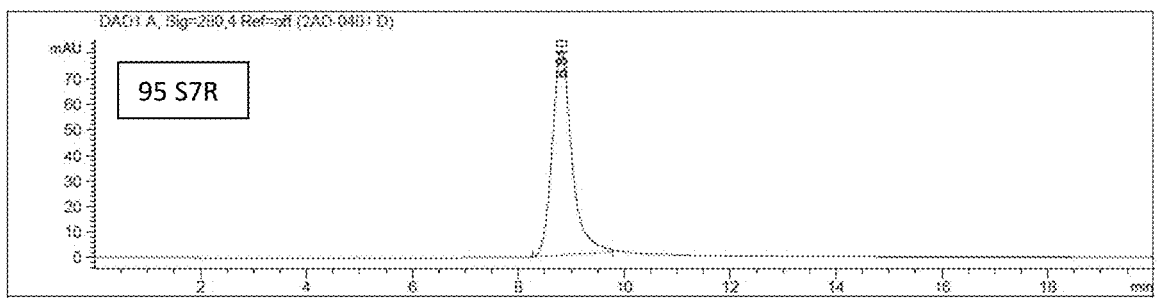
Figure 12C:
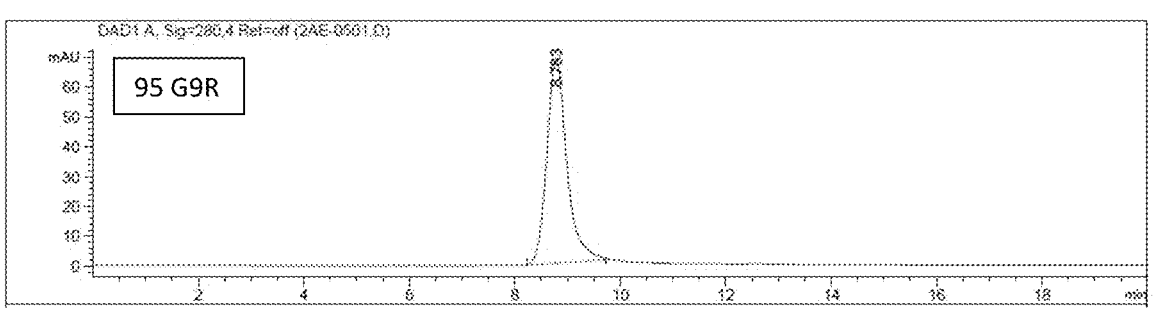
Figure 12D:
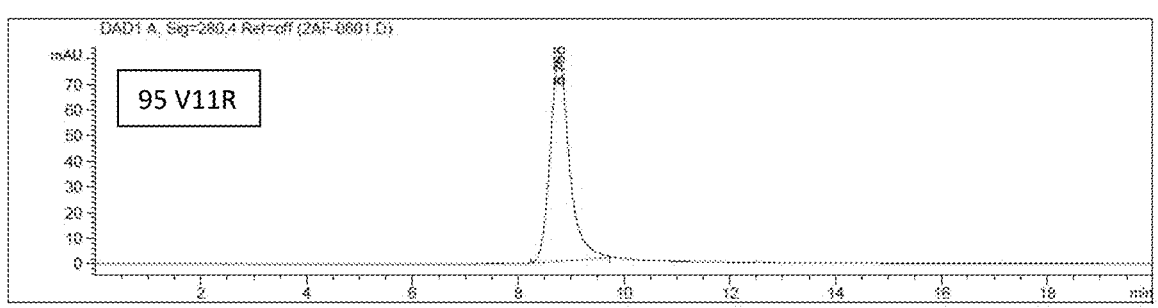
Figure 12E:
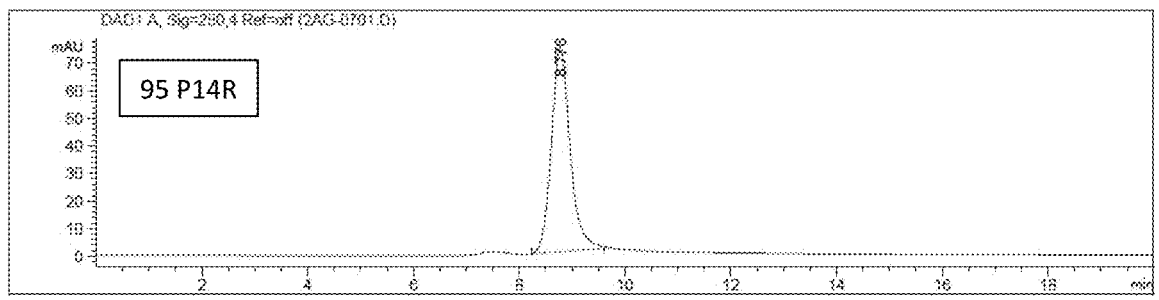
Figure 12F:
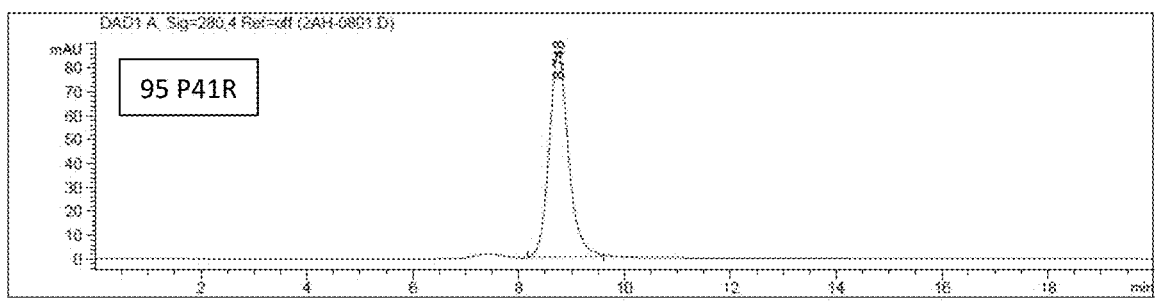
Figure 12G:
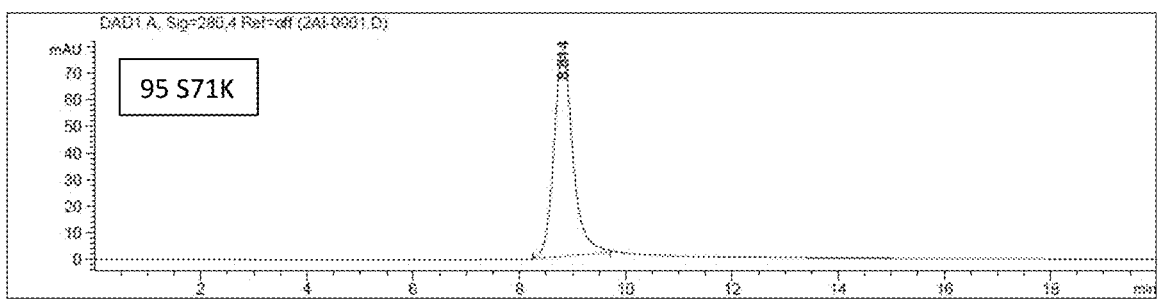
Figure 12H:
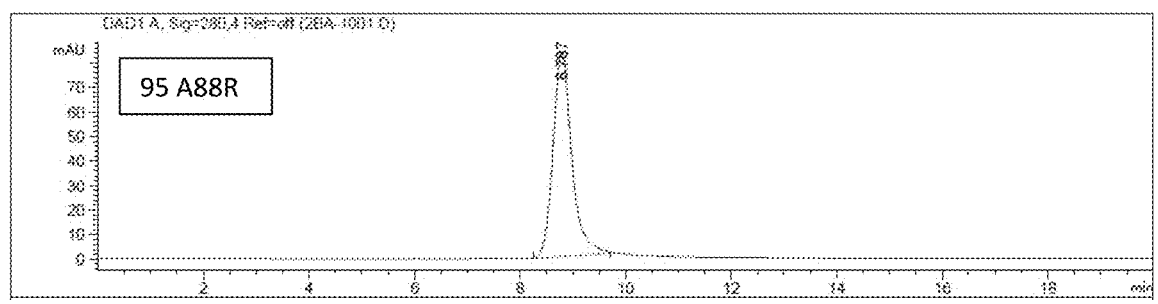
Figure 12I:
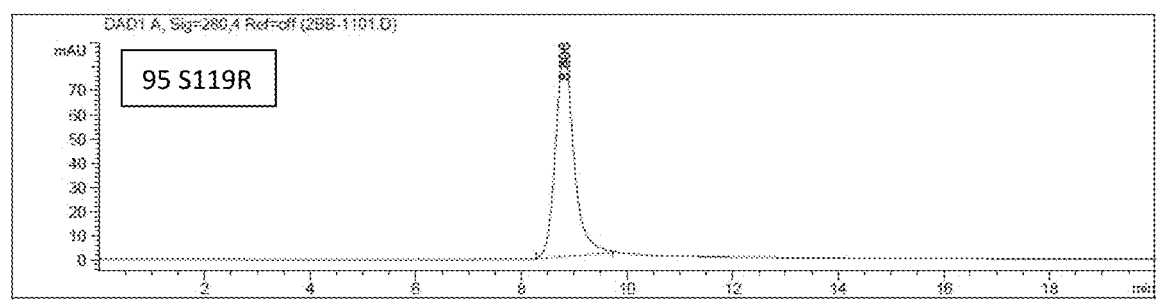

The characterization of CNTO95 variants is summarized in Table 4 below. The pIs of CNTO95 S7R, G9R, V11R, P14R, P41R, S71K, A88R, and S119R variants were 9.2, 9.2, 9.2, 9.2, 9.2, 9.1, 9.2, and 9.2, respectively, compared to the CNTO95 wildtype with a pI of 9.05. All the variants bound αVβ3 at least as well as the WT control. FIG. 11 shows binding of the above variants compared to wildtype (CNTO95). CNTO148 was used as a negative control. The variants also gave an SE-HPLC profile that was very similar to the WT. FIGS. 12A-12I show the SE-HPLC profiles for CNTO95 wildtype (FIG. 12A), S7R (FIG. 12B), G9R (FIG. 12C), V11R (FIG. 12D), P14R (FIG. 12E), P41R (FIG. 12F), S71K (FIG. 12G), A88R (FIG. 12H) and S119R (FIG. 12I).

TABLE 4

CNTO95 Variant Characterization Summary

| Kabat position | Mutation | Banding Pattern | % monomer | cIEF Charge Profile | Ag Binding | Stability ($T_m$ and $T_{agg}$) |
|---|---|---|---|---|---|---|
| 7 | S7R | WT-like | WT-like | WT-like | WT-like | WT-like |
| 9 | G9R | WT-like | WT-like | WT-like | WT-like | Greatly Decreased |
| 11 | V11R | WT-like | WT-like | WT-like | WT-like | Decreased |
| 14 | P14R | WT-like | Slight Aggregation | WT-like | WT-like | Decreased |
| 41 | P41R | WT-like | Slight Aggregation | WT-like | WT-like | Decreased |
| 74 | S71K | WT-like | WT-like | WT-like | WT-like | Decreased |
| 84 | A88R | WT-like | WT-like | WT-like | WT-like | WT-like |
| 113 | S119R | WT-like | WT-like | WT-like | WT-like | WT-like |

Figure 13A:
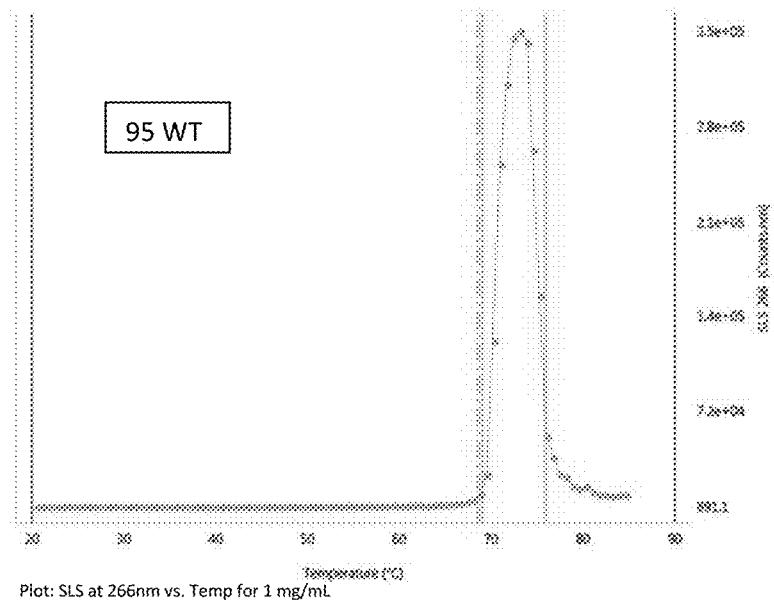
FIGS. 13A-13I are graphs showing onset of aggregation (colloidal stability) analysis of CNTO95 single substitution variants.
Figure 13B:
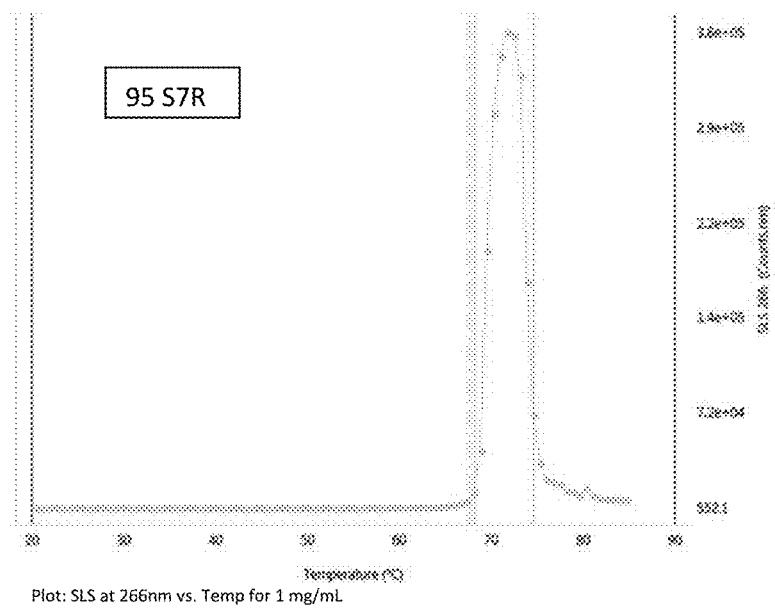
Figure 13C:
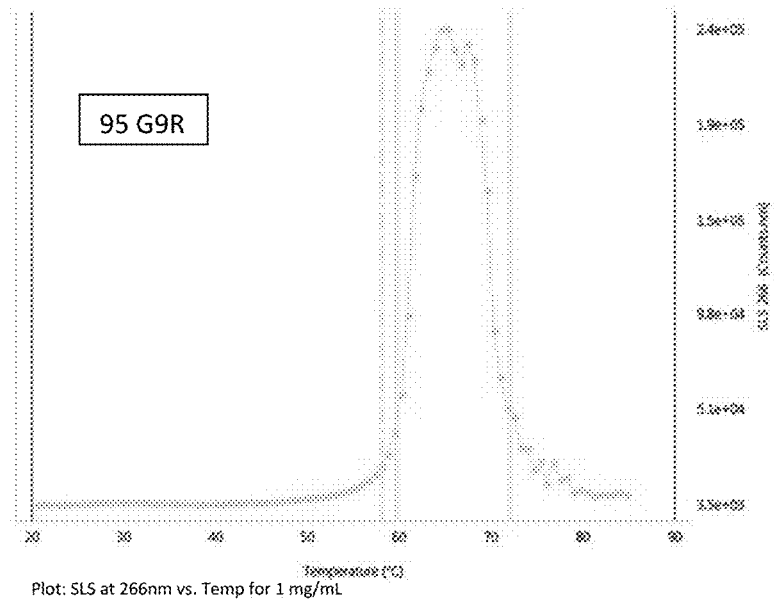
Figure 13D:
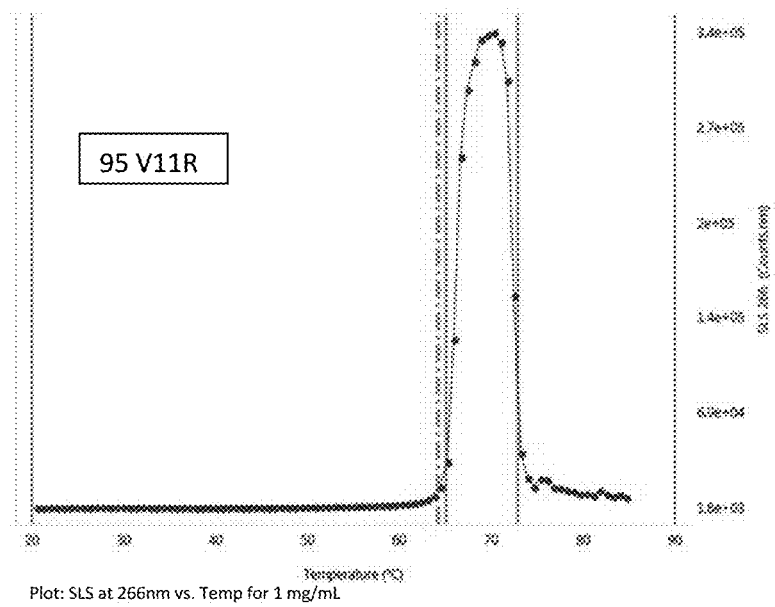
Figure 13E:
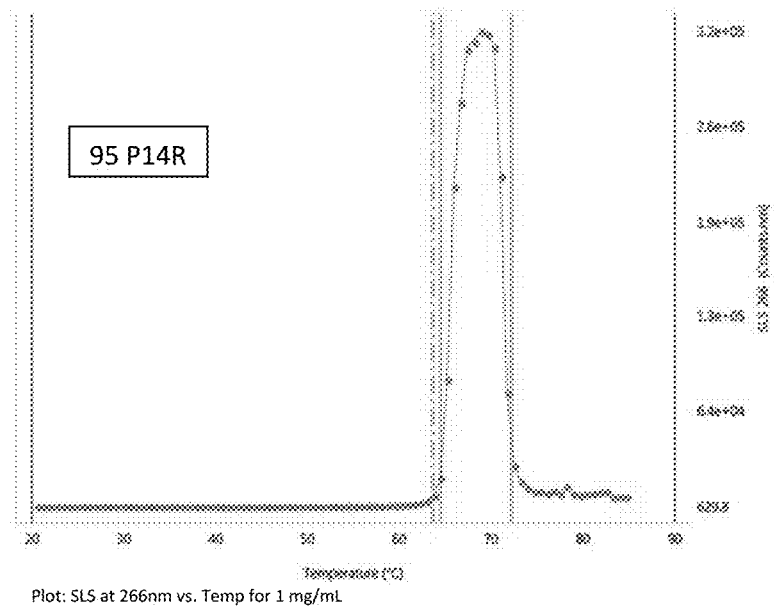
Figure 13F:
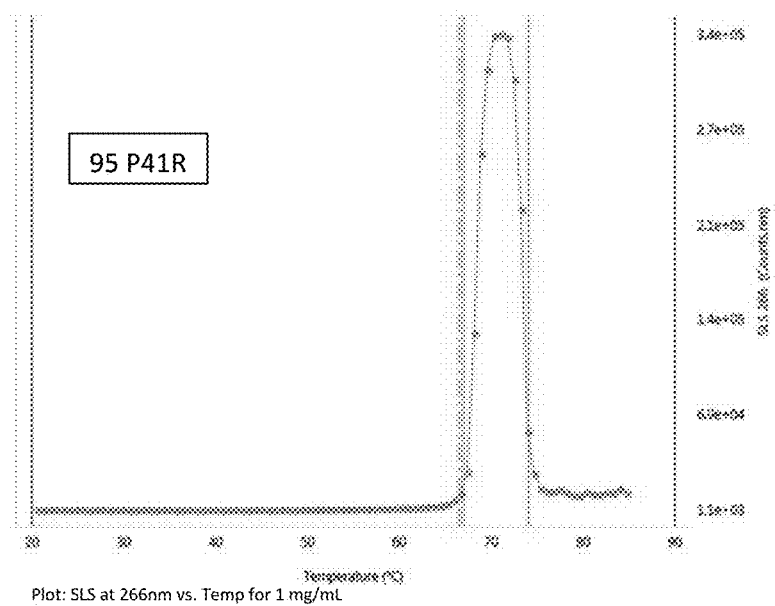
Figure 13G:
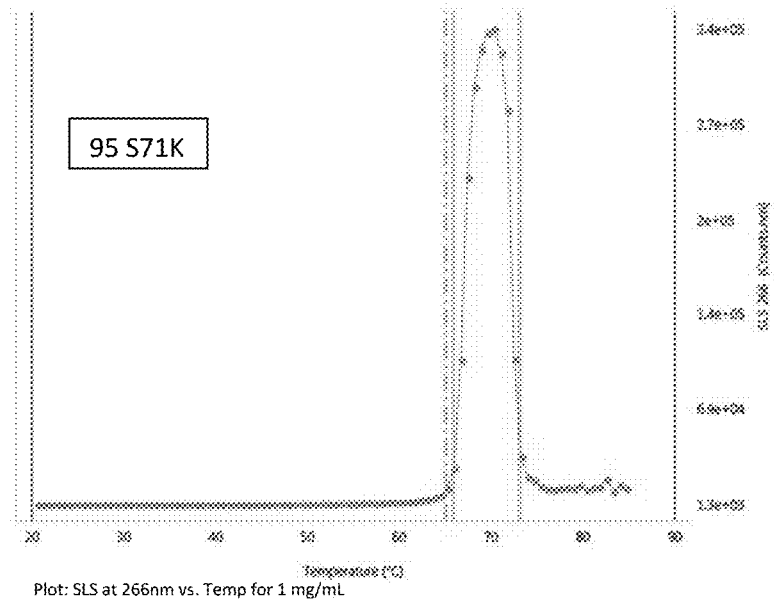
Figure 13H:
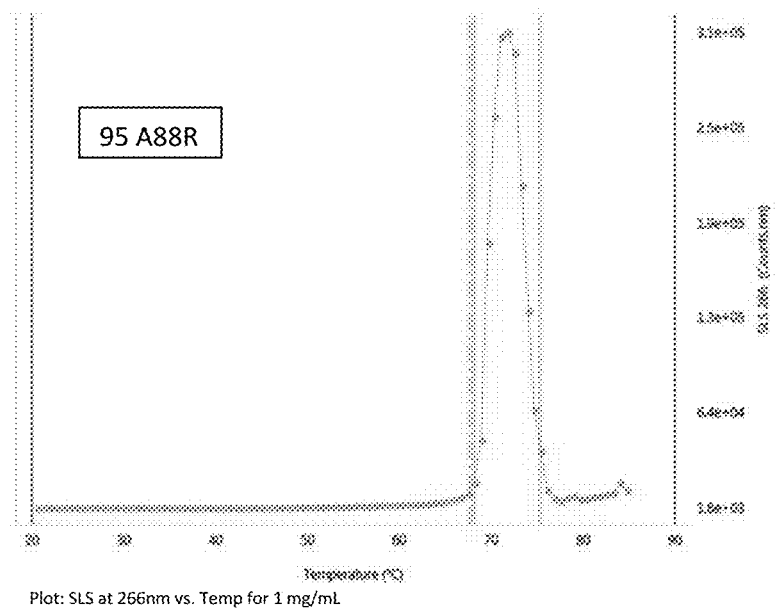
Figure 13I:
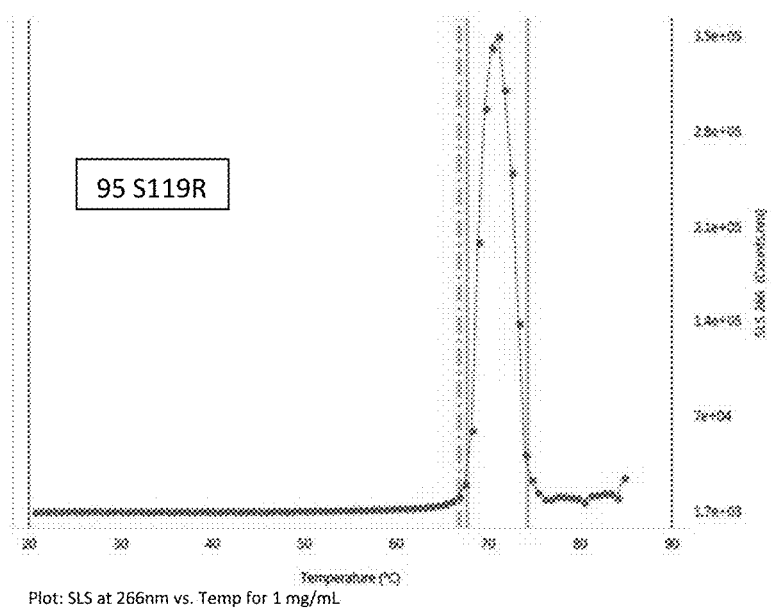

The onset of aggregation ($T_{agg}$) for the S7R, G9R, V11R, P14R, P41R, S71K, A88R, and S119R variants occurred at 67.2° C. (FIG. 13B), 57.9° C. (FIG. 13C), 63.9° C. (FIG. 13D), 63.5° C. (FIG. 13E), 66.4° C. (FIG. 13F), 64.9° C. (FIG. 13G), 67.6° C. (FIG. 13H), and 66.7° C. (FIG. 13I), compared to the onset of aggregation for wildtype CNTO95 which occurred at 68.2° C. (see FIG. 13A).

Figure 14A:
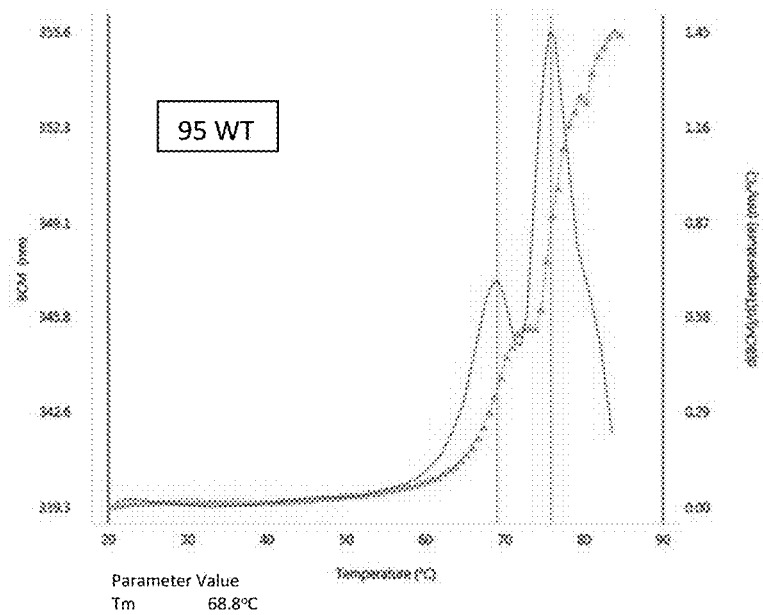
FIGS. 14A-14I are graphs showing the temperature of unfolding (conformational stability) analysis of CNTO95 single substitution variants.
Figure 14B:
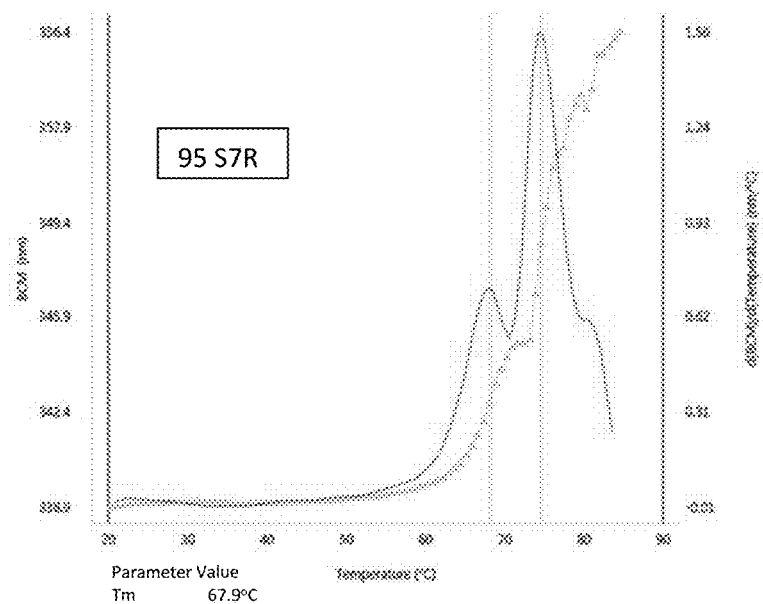
Figure 14C:
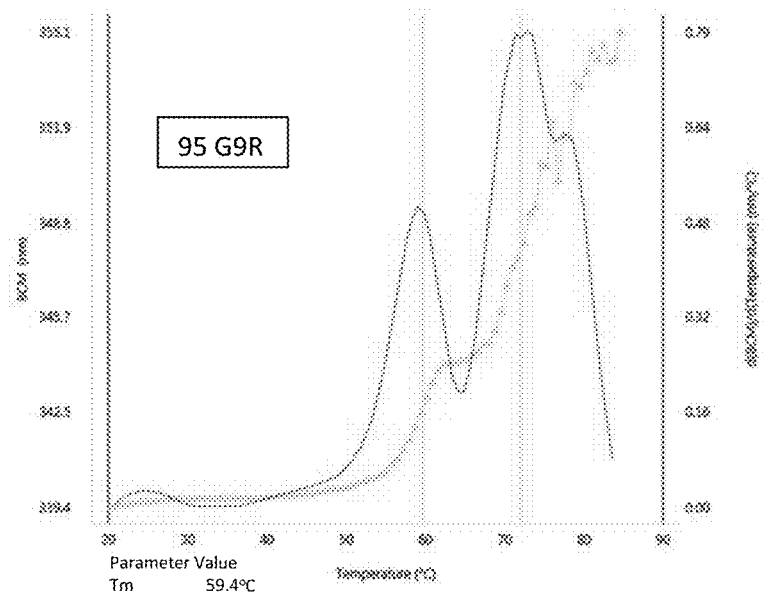
Figure 14D:
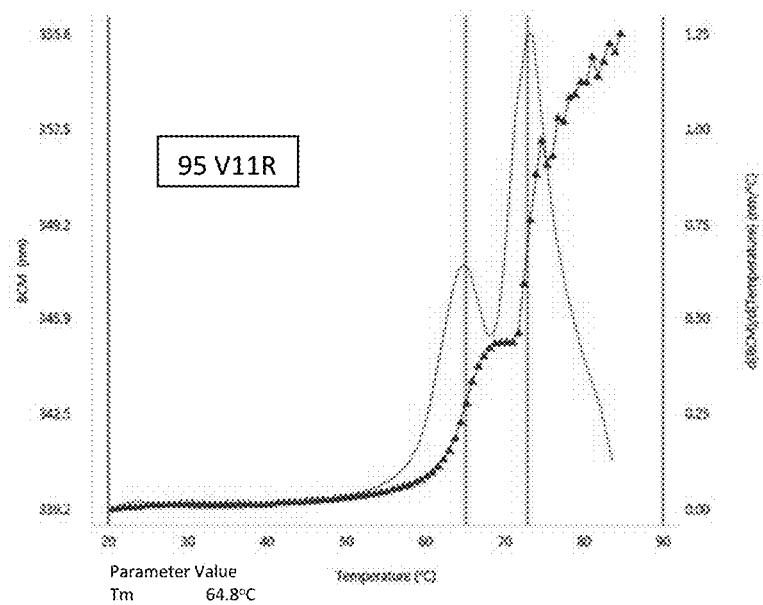
Figure 14E:
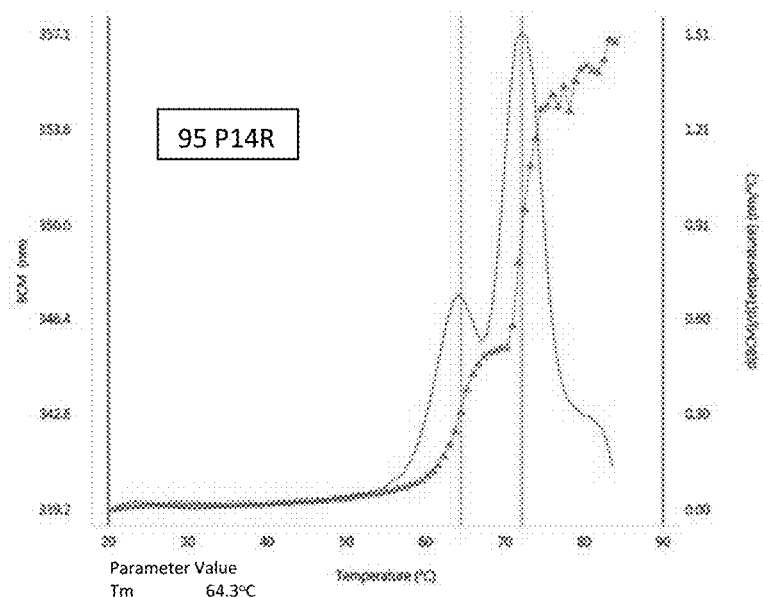
Figure 14F:
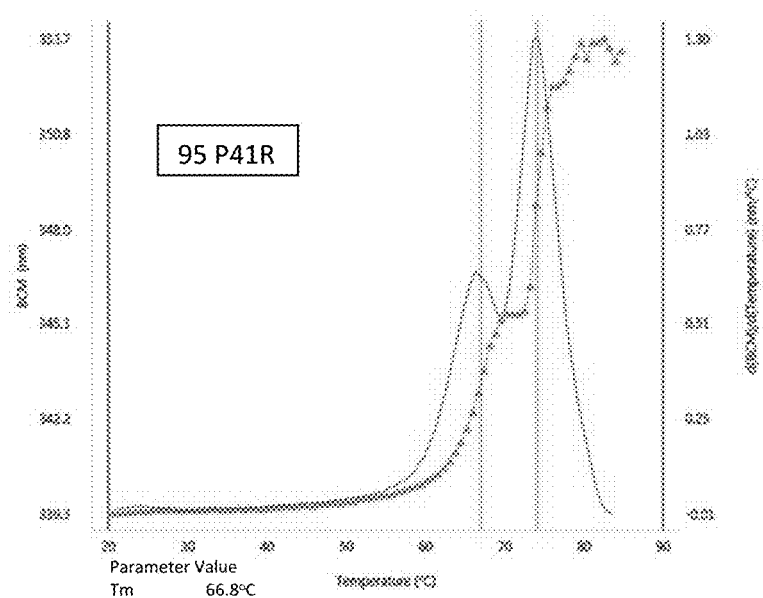
Figure 14G:
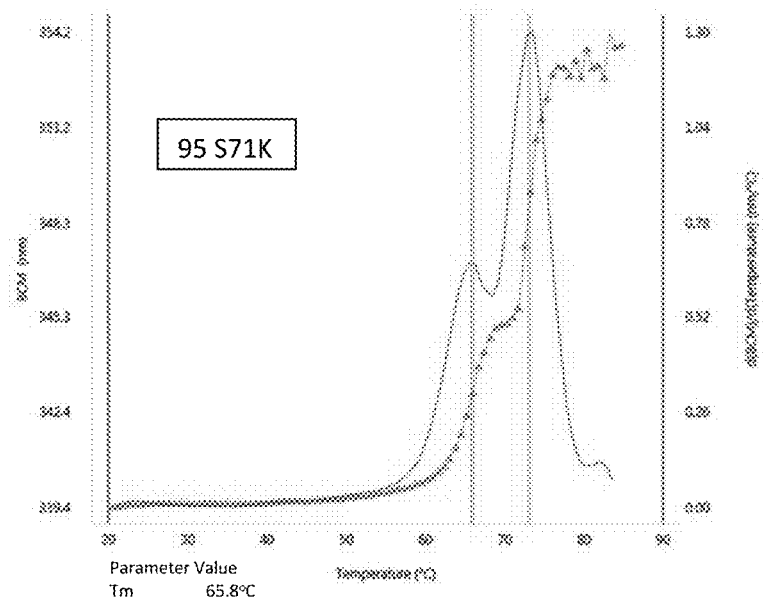
Figure 14H:
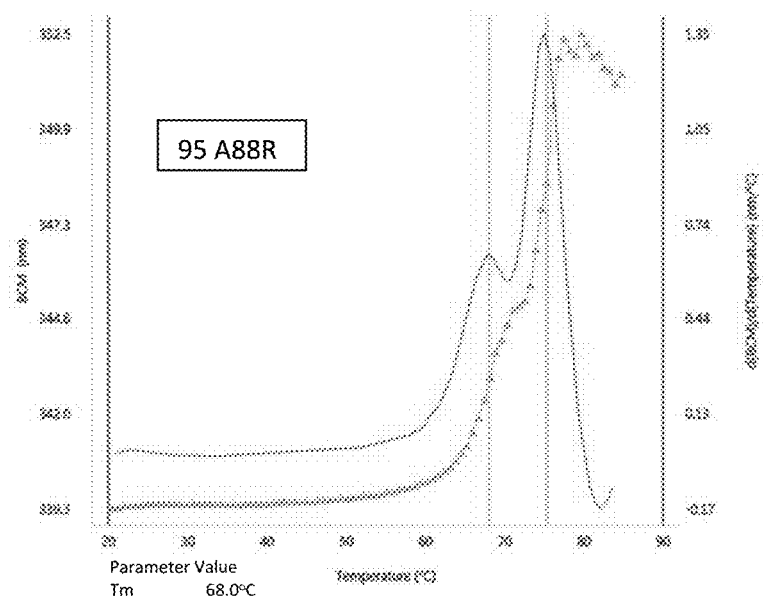
Figure 14I:
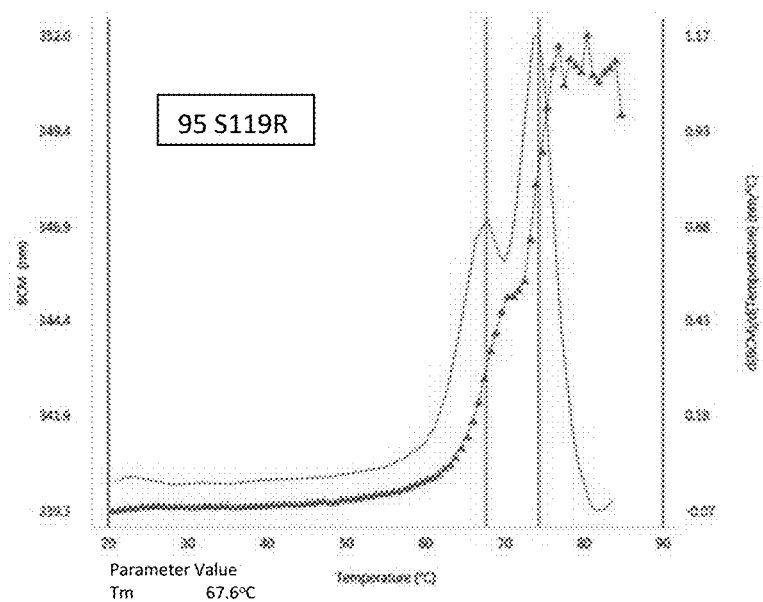

The unfolding temperature ($T_m$) of the S7R, G9R, V11R, P14R, P41R, S71K, A88R, and S119R variants occurred at 67.9° C. (FIG. 14B), 59.4° C. (FIG. 14C), 64.8° C. (FIG. 14D), 64.3° C. (FIG. 14E), 66.8° C. (FIG. 14F), 65.8° C. (FIG. 14G), 68.0° C. (FIG. 14H), and 67.6° C. (FIG. 14I), respectively, compared to the unfolding temperature of the wildtype CNTO95 which occurred at 68.8° C. (FIG. 14A). Variants that demonstrated a greater than 2° C. reduction in $T_m$ and $T_{agg}$ were regarded as having reduced stability and those that demonstrated a reduction greater than 5° C. were regarded as having greatly reduced stability. Of these variants, only the G9R variant demonstrated greatly reduced stability; it had a lower $T_m$ by 9.4° C. and a lower onset of aggregation by 10.3° C. The V11R, P14R, P41R, and S71K variants demonstrated reduced stability. They had a lower $T_m$ by 4° C., 4.5° C., 2° C., and 3° C., respectively, and a lower $T_{agg}$ by 4.3° C., 4.7° C., 1.8° C., and 3.2° C., respectively.

Example 3

Isoelectric Point Modification of Monoclonal and Bi-Specific Anti-TIM3 and Anti-PD1 Antibodies To further examine the utility of amino acid substitutions at Kabat positions 74, 82a, and 84 in the heavy chain variable region to modify isoelectric point, variants of two additional antibodies, anti-TIM3 and anti-PD1 antibodies, were tested. TIMB337 is a monoclonal antibody that binds TIM3 (CD366), and PD1B244 is a monoclonal antibody that binds PD-1 (CD279). The pIs of TIMB337 and PD1B244 are 7.26 and 7.06 (for the IgG4 version); therefore, the difference in pI between these two homodimers and a bispecific formed by combining the two is less than 0.1 units. This was reflected on a CEX column where the resolution was observed to be 0.1.

Amino acid substitutions in the heavy chain variable regions of TIM337 and PD1B244 at positions 74, 82a, and 84 (Kabat numbering) (corresponding to amino acid positions 75, 84, and 88 of SEQ ID NO: 2 and SEQ ID NO: 3, respectively) were initially tested to determine their ability to decrease the isoelectric point (pI) of these antibodies (see Tables 5 and 6). These substitutions were introduced either singly or in combination via modification of the nucleic acid molecule encoding the heavy chain variable region. The variants were expressed using Expi293 cells in 24-well plates.

TABLE 5

TIMB337 Antibody Variants

| Kabat position | Mutation | Surface exposure (%) | Location | Structure Comment |
|---|---|---|---|---|
| 74 | S75D | 86 | Near CDR | protrudes |
| 82a | N84D | 33 | Near bottom loop | On surface |
| 84 | A88D | 45 | Bottom loop | On surface |

TABLE 6

PD1B244 Antibody Variants

| Kabat position | Mutation | Surface exposure (%) | Location | Structure Comment |
|---|---|---|---|---|
| 74 | S75D | 78 | Near CDR | Mostly exposed |
| 82a | S84D | 27 | Near bottom loop | Only the hydroxyl exposed |
| 84 | S88D | 33 | Bottom loop | On surface |

The TIMB377 and PD1B244 variants were expressed in 24 well plates and purified. The same panel of methods used for the characterization of the CNTO148 variants was used to analyze the TIMB377 and PD1B244 variants, including cSDS, SE-HPLC, cIEF. In this case cIEF was done with pH 3-10 and pH 5-8 ampholytes. Stability was measured using the Activa Optim2 as before. Antigen binding was also measured for each of the POC antibodies. An ELISA was used to measure TIM3 binding. Briefly, Maxisorp plates (Nunc) were coated with Streptavidin, and then blocked with PBS with 0.4% BSA. Biotinylated human TIM3-Fc fusion from R&D systems at a concentration of 1 ug/mL in PBS, 0.4% BSA was then bound. Serial dilutions of the variants were then added and allowed to bind. Next, peroxidase conjugated goat anti-human kappa (Southern Biotech) at a dilution of 1:5000 into PBS, 0.4% BSA was added (anti-FC was not used to avoid binding the TIM3-Fc fusion). Finally, TMB substrate (Fitzgerald) was used to for detection.

To measure the binding of charge variants to PD1 the Proteon SPR instrument was used. For this, a GLC type sensor chip was prepared by covalently immobilizing goat anti-human/anti-mouse Fc antibody (in Na acetate pH 4.5) over flow cells of all 6 channels (5000 RU). Next, anti-PD1 mAbs were diluted to 0.001 mg/ml in PBSTE and captured over all ligand channels (~180 RU). Finally, human PD1 antigen (100 nM-0.4 nM at 4-fold dilutions in PBSTE) was injected over the anti-PD1 mAb captured channels and the association/dissociation profiles were monitored for 4 and 30 minutes, respectively. Regeneration was performed at the end of each titration cycle using 0.85% $H_3PO_4$. Data was analyzed to check for capture and binding interactions.

Results

Analysis of the TIMB377 variants showed they all behaved similarly to the wildtype (see Table 7). The pI of all three S75D N84D and A88D variants was 8.5 compared to the WT with a pI of 8.7. All three variants bound TIM3 at least as well as the WT (FIG. 15), and they each gave an SE-HPLC profile that was very similar to the WT (FIGS. 16A-16D). In addition, the onset of aggregation for the S75D, N84D and A88D variants at 67.5° C., 68.2° C. and 66.7° C., was similar to the WT onset at 68.5° C. (FIGS. 17A-17D).

TABLE 7

TIMB377 Substitution Variant Characterization

| Kabat position | Mutation | cSDS banding pattern | % monomer | cIEF Charge Profile | Ag Binding | Stability (Optim2) |
|---|---|---|---|---|---|---|
| 74 | S75D | WT-like | WT-like | WT-like | WT-like | WT-like |
| 82a | N84D | WT-like | WT-like | WT-like | WT-like | WT-like |
| 84 | A88D | WT-like | WT-like | WT-like | WT-like | WT-like |

PD1B244 single-substitution variant characterization results are shown in Table 8 below. In these experiments wildtype anti-PD1 showed a tendency to aggregate as evidenced by SE-HPLC, which made it difficult to determine if the substitutions had an effect on aggregation. The wildtype purity by SE-HPLC was 78% monomer, while the single mutants ranged from 51% to 95% monomeric. Previous experiments characterizing the PD-1 antibody showed that aggregation of this antibody is sensitive to temperature and pH, therefore, variability in the proportion of monomer could be attributed to differences in experimental conditions during the processing of the samples. For this reason, the variable proportion of monomer seen in some of the variants was not considered a valid basis on which to exclude these substitutions from further evaluation and % monomer was not included in the final analysis of the PD-1 antibody mutants. It should be noted, however, that further studies demonstrated that through process optimization such aggregation can be minimized significantly and the experiments currently described were performed in PBS without such optimization.

The pIs of the S75D, S84D, and S88D variants were 8.6, 8.6 and 8.7 compared to the WT with a pI of 8.9. All three variants bound human PD1 with a KD that was similar to WT (FIG. 18). They also gave an SE-HPLC profile that was very similar to the WT. In this case, the SE-HPLC profile of the WT anti-PD1 antibody included several bands that eluted earlier than the presumptive monomer peak. The number and appearance of these peaks was not affected by the charge substitutions (FIGS. 19A-19D). In addition, the onset of aggregation for the S75D, S84D and S88D variants at 66.6° C., 66.1° C. & 66.5° C. were similar to the WT onset at 65.7° C. (FIGS. 20A-20D). Aside from the variable SE-HPLC results for % monomer, all other data demonstrate that the 3 single mutations tested were all WT-like.

TABLE 8

PD1B244 Substitution Variant Characterization

| Kabat position | Mutation | cSDS banding pattern | SE-HPLC profile | cIEF Charge Profile | Ag Binding | Stability (Optim2) |
|---|---|---|---|---|---|---|
| 74 | S75D | WT-like | WT-like | WT-like | WT-like | WT-like |
| 82a | S84D | WT-like | WT-like | WT-like | WT-like | WT-like |
| 84 | S88D | WT-like | WT-like | WT-like | WT-like | WT-like |

Example 4

CNTO148 Multiple Substitution Variant Characterization

The pIs of four multiple substitution CNTO148 variants composed of S75D, N84D or A88D are shown in the Table 9 below. For the CNTO148 antibody, combining two of the substitutions gave a reduction in pI of between 0.25 and 0.31 pH units. Combining all three resulted in a decrease of 0.45 pH units.

TABLE 9

Isoelectric Point of CNTO148 Combination Variants

| Position (sequential) | pI by dEF | pI decrease |
|---|---|---|
| WT | 9.22 | |
| N84D A88D | 8.97 | 0.25 |
| S75D A88D | 8.93 | 0.29 |
| S75D N84D A88D | 8.77 | 0.45 |
| S75D N84D | 8.91 | 0.31 |

Figure 21:
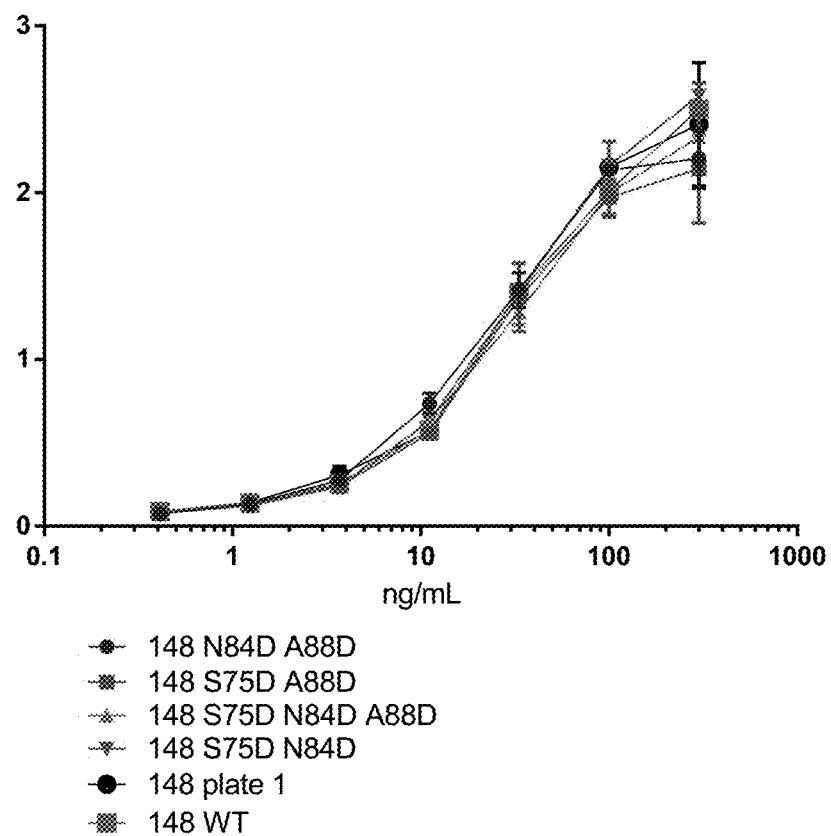
FIG. 21 shows human TNF binding ELISA of CNTO148 antibody substitution combination variants.
Figure 22A:
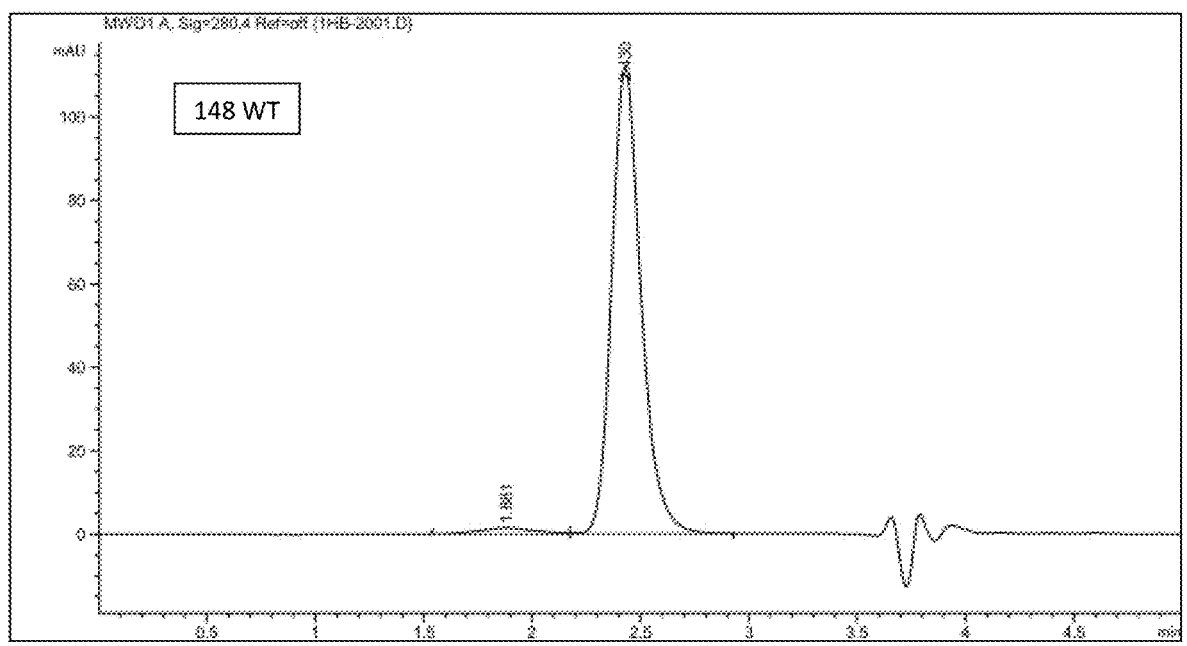
FIGS. 22A-22E show analytical size exclusion chromatography analysis of CNTO148 combination variants.
Figure 22B:
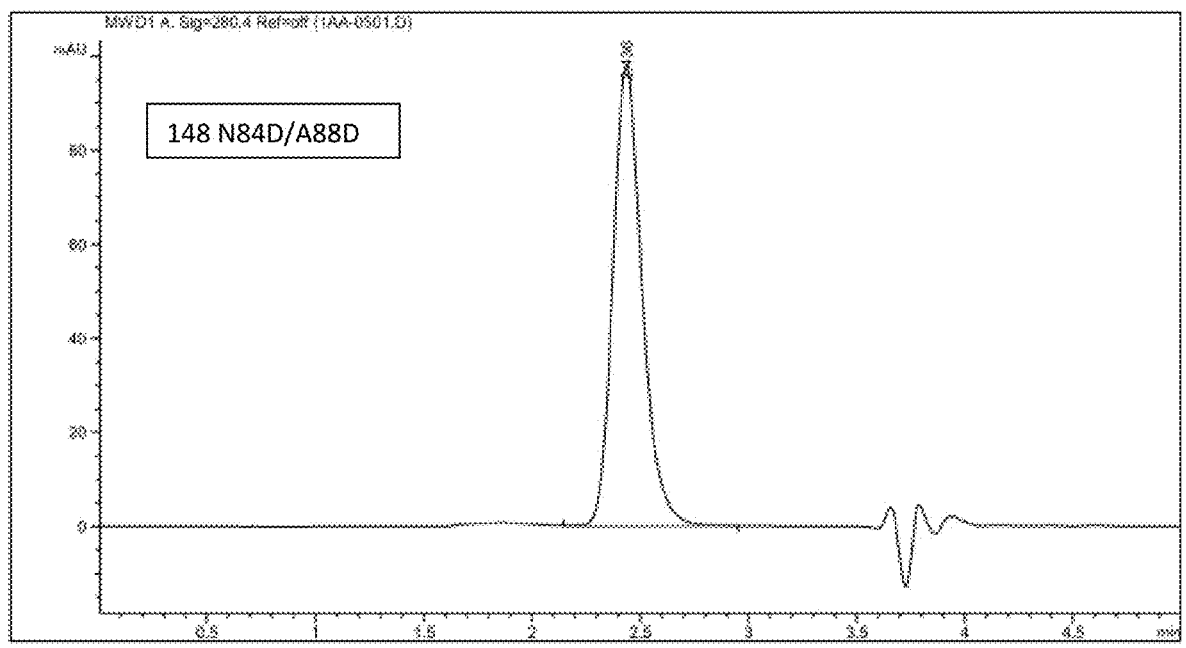
Figure 22C:
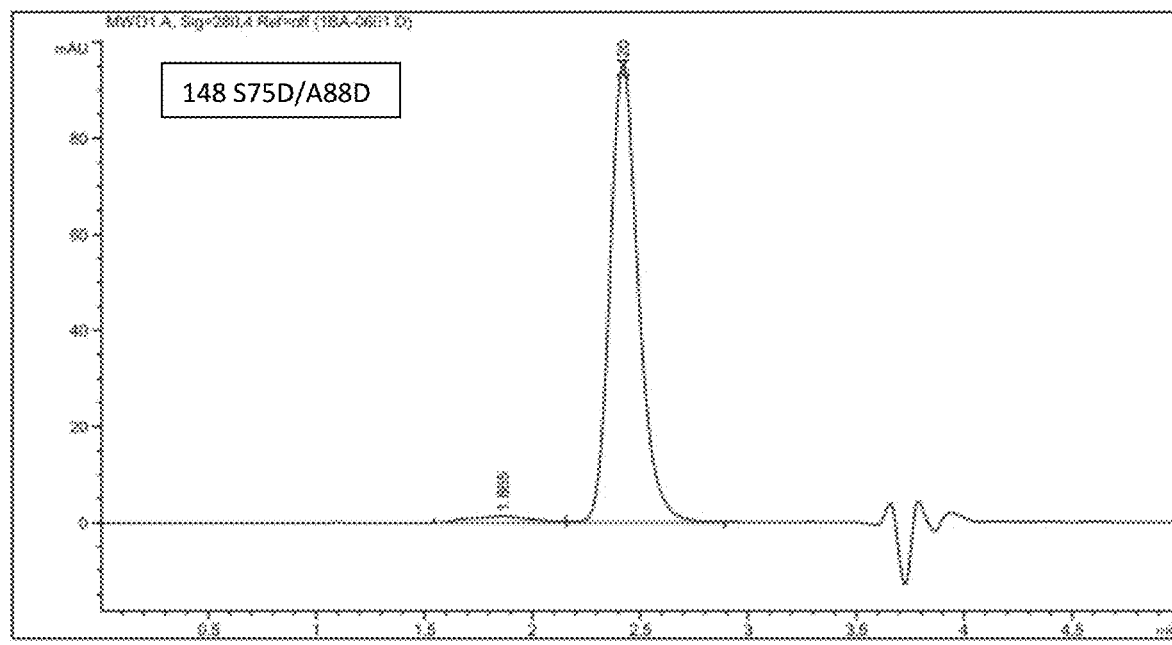
Figure 22D:
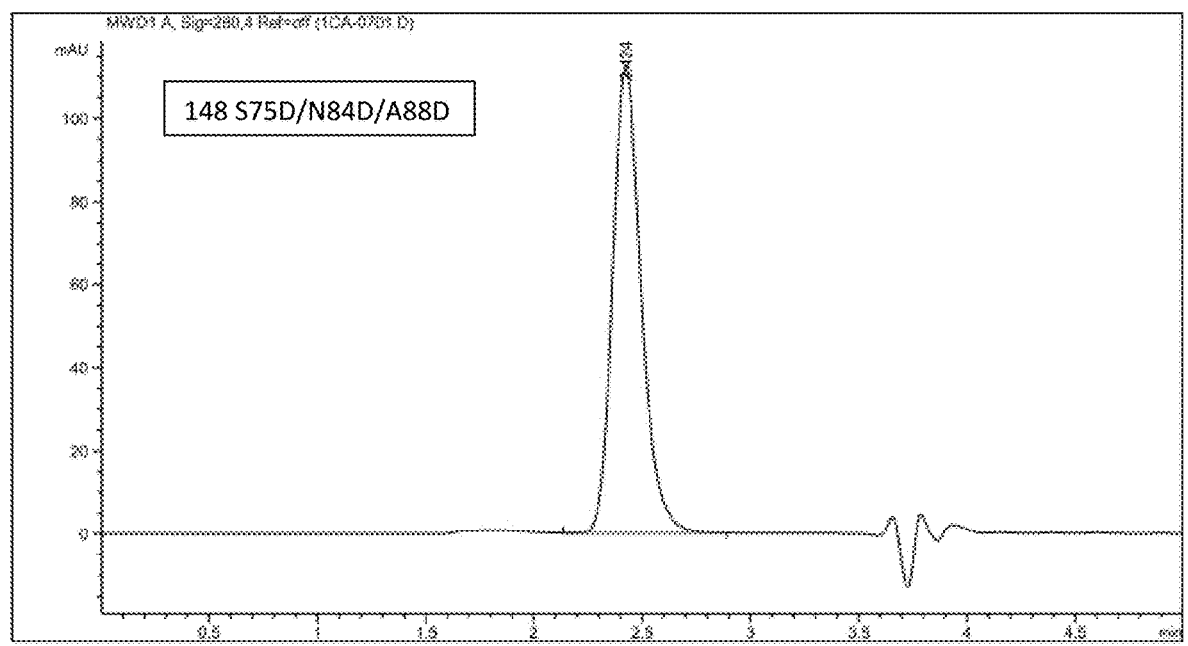
Figure 22E:
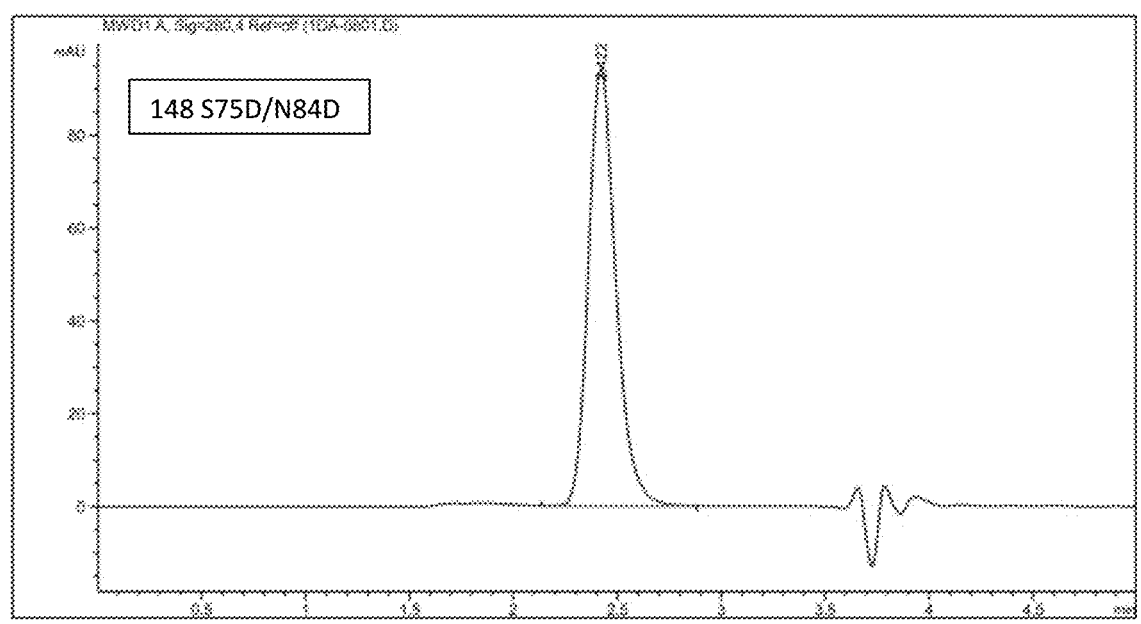
Figure 23A:
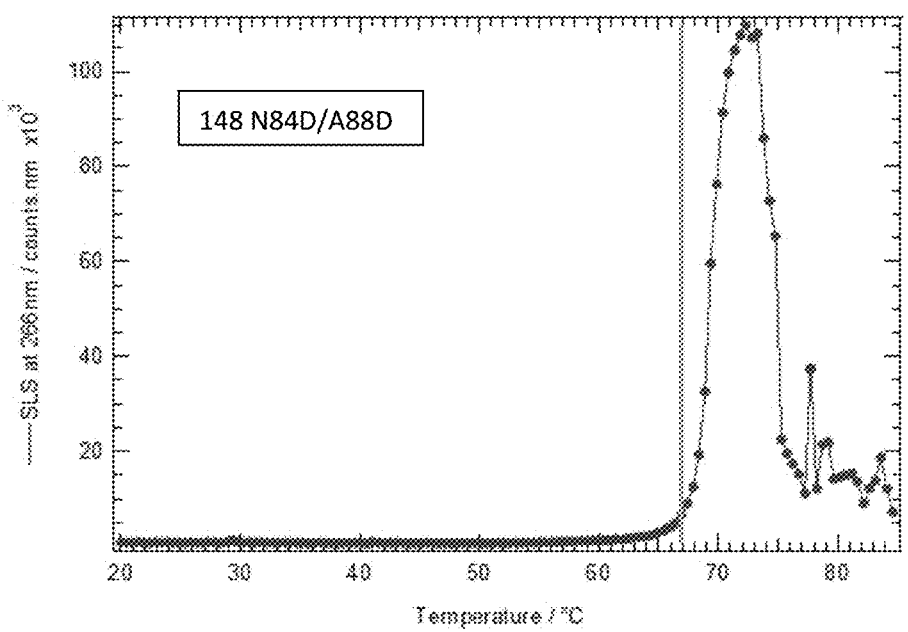
FIGS. 23A-23E show onset of aggregation (colloidal stability) analysis of a CNTO148 combination variants.
Figure 23B:
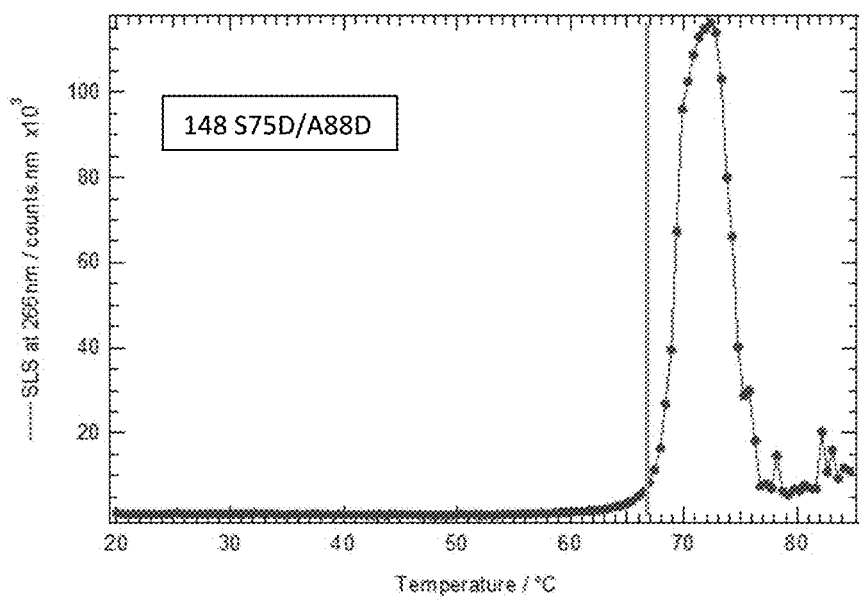
Figure 23C:
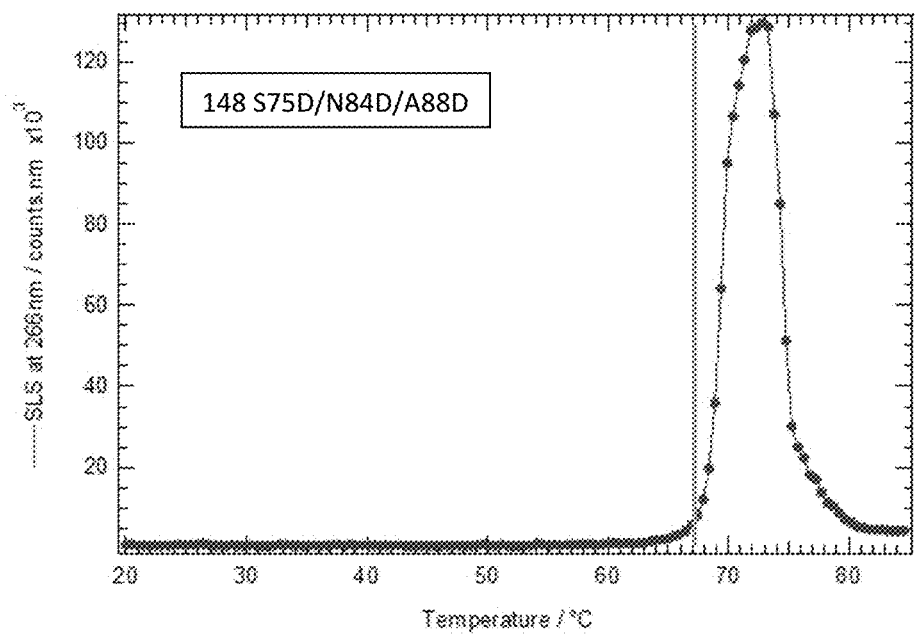
Figure 23D:
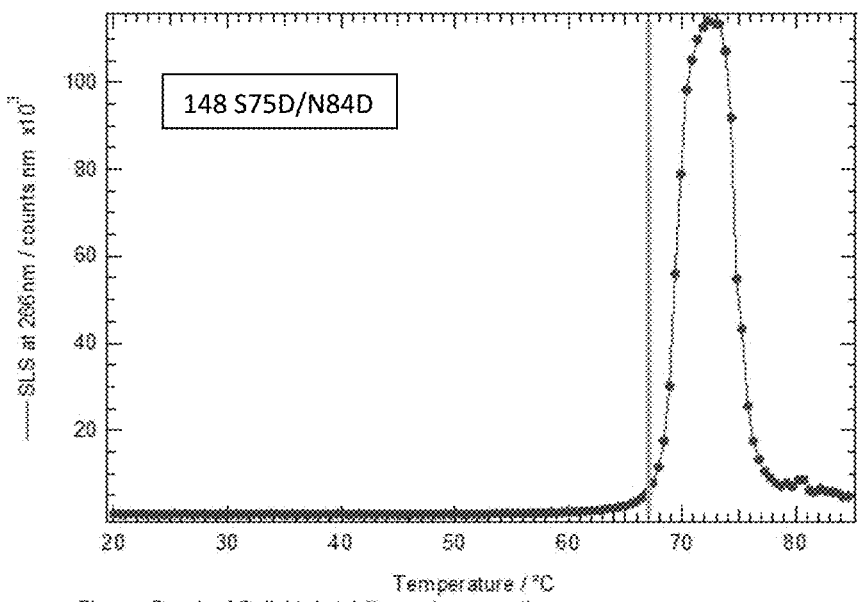
Figure 23E:
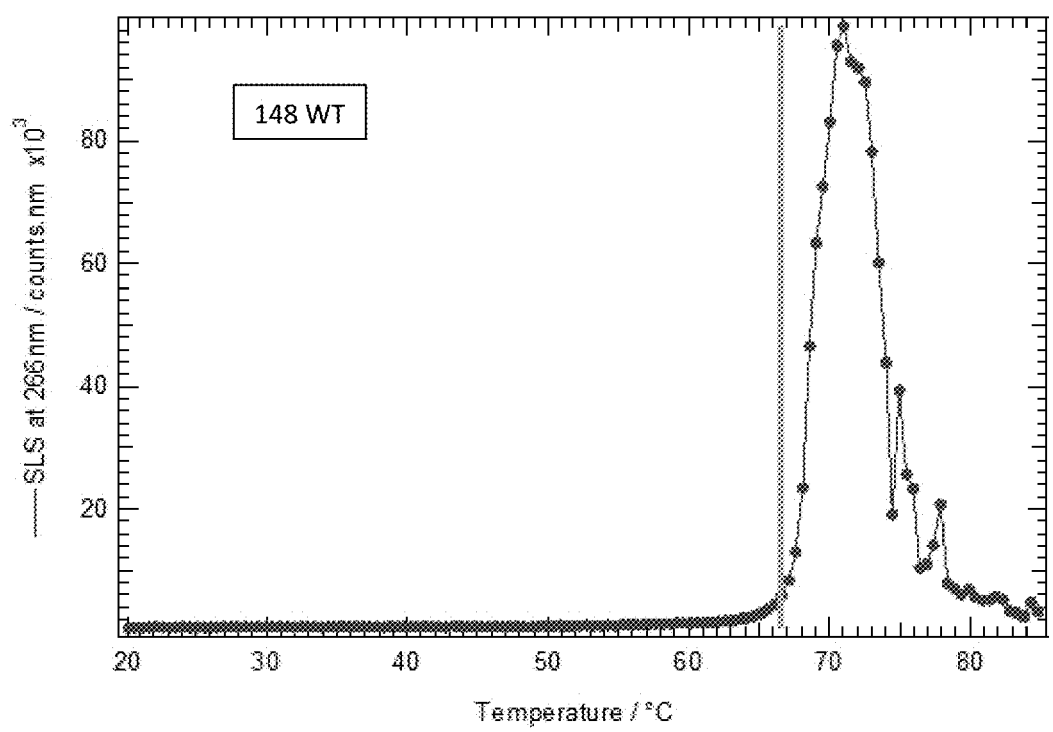
Figure 24A:
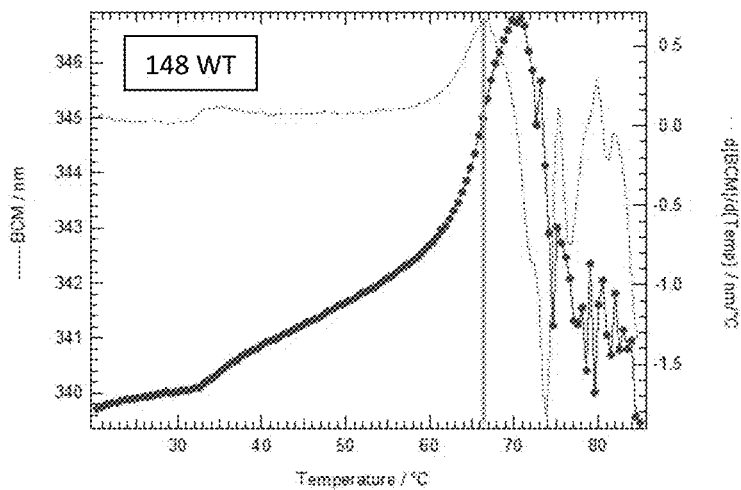
FIGS. 24A-24E are graphs showing temperature of unfolding (conformational stability) analysis of CNTO148 multiple substitution variants.
Figure 24B:
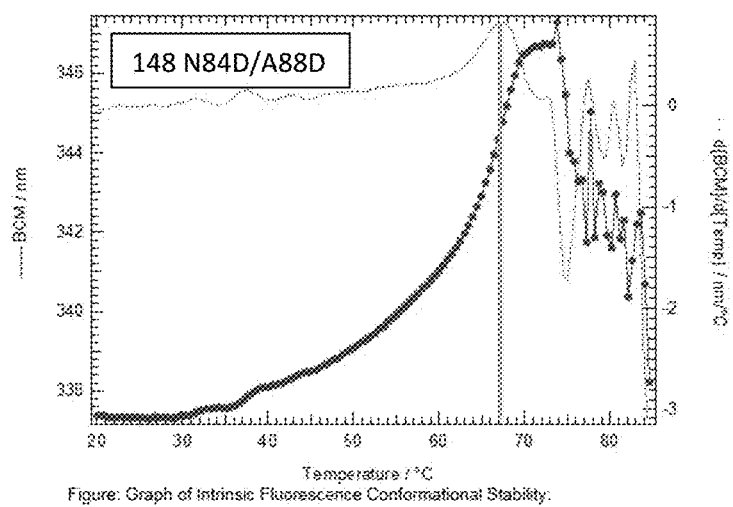
Figure 24C:
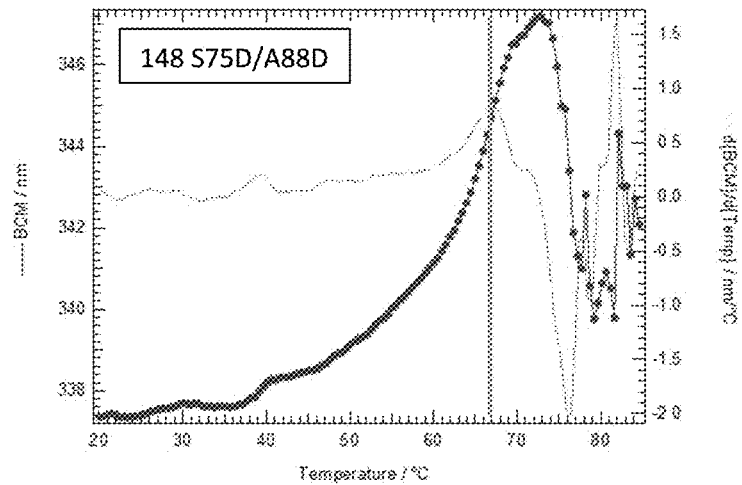
Figure 24D:
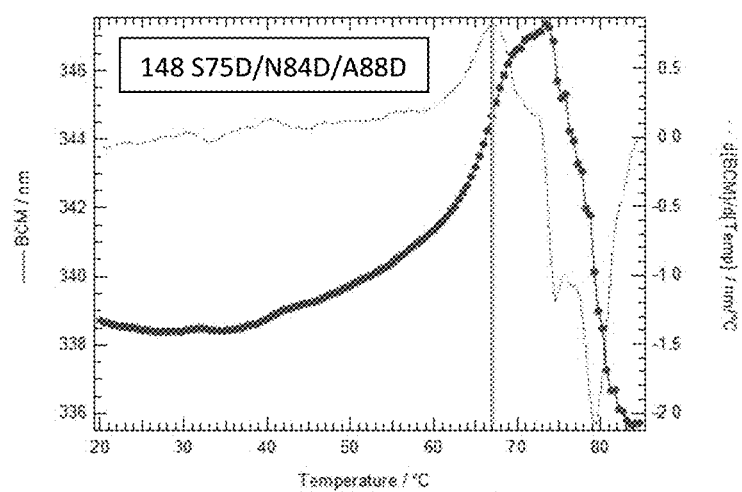
Figure 24E:
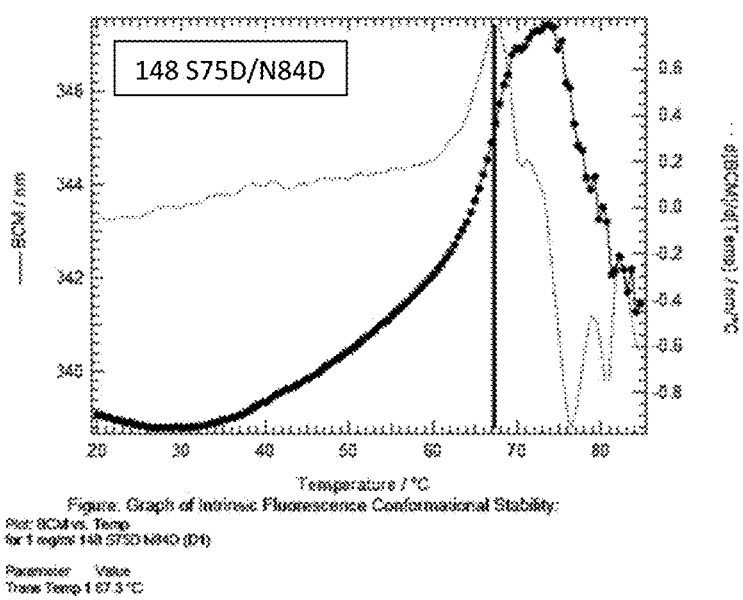

As shown in FIG. 21, all of the combination variants bound TNF similarly to the wildtype CNTO148. They also gave an SE-HPLC profile that was very similar to the WT (FIGS. 22A-22E). In addition, both the conformational and colloidal stability of the variants was similar to the WT (Table 10 below, FIGS. 23A-23E and FIGS. 24A-24E). The conformational stability of the variants (Tm) was within 0.5° C. of the WT and the colloidal stability (onset of aggregation) was within 0.7° C. of the WT.

TABLE 10

Protein Stability of CNTO148 Combination Variants

| | Conformational Stability | Colloidal Stability |
|---|---|---|
| WT | 66.8° C. | 66.5° C. |
| N84D A88D | 67.1° C. | 66.8° C. |
| S75D A88D | 66.8° C. | 66.8° C. |
| S75D N84D | 67.3° C. | 67.1° C. |
| S75D N84D A88D | 66.9° C. | 67.2° C. |

Although preferred embodiments are depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of decreasing the isoelectric point of an antibody that comprises
a first polypeptide comprising a heavy chain variable region ($V_H$) and
a second polypeptide comprising a $V_H$,
one or more amino acid residues at positions 82a and 84 in the $V_H$ of at least one of the first or second polypeptides, according to the Kabat numbering system, with a negatively charged amino acid residue to thereby decrease the isoelectric point of the antibody.

2. The method of claim 1, wherein, prior to the substituting, the one or more amino acid residues at positions 82a and 84 (Kabat numbering) are neutrally charged amino acid residues.

3. The method of claim 1, wherein, prior to the substituting, the one or more amino acid residues at positions 82a and 84 (Kabat numbering) are positively charged amino acid residues.

4. The method of claim 1, wherein the antibody is a multi-specific antibody and the first and second polypeptides comprise different heavy chain variable regions.

5. The method of claim 4, wherein said substituting is carried out in only one of the first or second polypeptides.

6. The method of claim 4, wherein said substituting is carried out in both of the first and second polypeptides.

7. The method of claim 6, wherein the one or more amino acid residue substitutions of the first polypeptide are different than the one or more amino acid residue substitutions of the second polypeptide.

8. The method of claim 1, wherein further comprising substituting the amino acid residue at position 74 (Kabat numbering) in at least one of the first or second polypeptides with a negatively charged amino acid residue.

9. The method of claim 1, wherein
the amino acid residue at position 82a (Kabat numbering) in at least one of the first or second polypeptides is substituted with the negatively charged amino acid residue.

10. The method of claim 1, wherein
the amino acid residue at position 84 (Kabat numbering) in at least one of the first or second polypeptides is substituted with the negatively charged amino acid residue.

11. The method of claim 1, wherein
the amino acid residues at both positions 82a and 84 (Kabat numbering) in at least one of the first or second polypeptides are substituted with the negatively charged amino acid residue.

12. The method of claim 8, wherein
the amino acid residues at positions 74, 82a, and 84 (Kabat numbering) in at least one of the first or second polypeptides are substituted with the negatively charged amino acid residue.

13. The method of claim 1, wherein the antibody is an IgG antibody.

14. The method of claim 1, wherein the antibody is a chimeric antibody, a humanized antibody, or a human antibody.

15. An antibody having a modified isoelectric point produced by the method of claim 1.

* * * * *

SEQUENCE LISTING

<160> NUMBER OF SEQ ID NOS: 13

<210> SEQ ID NO 1
<211> LENGTH: 126
<212> TYPE: PRT
<213> ORGANISM: Artificial Sequence
<220> FEATURE:
<223> OTHER INFORMATION: CNTO148 VH variants
<220> FEATURE:
<221> NAME/KEY: MISC_FEATURE
<222> LOCATION: (75)..(75)
<223> OTHER INFORMATION: Xaa is Ser or Asp
<220> FEATURE:
<221> NAME/KEY: MISC_FEATURE

```
<222> LOCATION: (84)..(84)
<223> OTHER INFORMATION: Xaa is Asn or Asp
<220> FEATURE:
<221> NAME/KEY: MISC_FEATURE
<222> LOCATION: (88)..(88)
<223> OTHER INFORMATION: Xaa is Ala or Asp

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Xaa Lys Asn Thr Leu Tyr
65                  70                  75                  80

Leu Gln Met Xaa Ser Leu Arg Xaa Glu Asp Thr Ala Val Tyr Tyr Cys
            85                  90                  95

Ala Arg Asp Arg Gly Ile Ala Ala Gly Gly Asn Tyr Tyr Tyr Tyr Gly
        100                 105                 110

Met Asp Val Trp Gly Gln Gly Thr Thr Val Thr Val Ser Ser
    115                 120                 125

<210> SEQ ID NO 2
<211> LENGTH: 117
<212> TYPE: PRT
<213> ORGANISM: Artificial Sequence
<220> FEATURE:
<223> OTHER INFORMATION: TIMB377 heavy chain variable region (TM3H24)
<220> FEATURE:
<221> NAME/KEY: MISC_FEATURE
<222> LOCATION: (75)..(75)
<223> OTHER INFORMATION: Xaa is Ser or Asp
<220> FEATURE:
<221> NAME/KEY: MISC_FEATURE
<222> LOCATION: (84)..(84)
<223> OTHER INFORMATION: Xaa is Ser Asn or Asp
<220> FEATURE:
<221> NAME/KEY: MISC_FEATURE
<222> LOCATION: (88)..(88)
<223> OTHER INFORMATION: Xaa is Ser Ala or Asp

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Xaa Lys Asn Thr Leu Tyr
65                  70                  75                  80

Leu Gln Met Xaa Ser Leu Arg Xaa Glu Asp Thr Ala Val Tyr Tyr Cys
            85                  90                  95

Ala Lys Ser Pro Tyr Ala Pro Leu Asp Tyr Trp Gly Gln Gly Thr Leu
        100                 105                 110

Val Thr Val Ser Ser
        115
```

-continued

```
<210> SEQ ID NO 3
<211> LENGTH: 123
<212> TYPE: PRT
<213> ORGANISM: Artificial Sequence
<220> FEATURE:
<223> OTHER INFORMATION: PD1B244 heavy chain variable region PD1H170
      variant
<220> FEATURE:
<221> NAME/KEY: MISC_FEATURE
<222> LOCATION: (75)..(75)
<223> OTHER INFORMATION: Xaa is Ser or Asp
<220> FEATURE:
<221> NAME/KEY: MISC_FEATURE
<222> LOCATION: (84)..(84)
<223> OTHER INFORMATION: Xaa is Ser or Asp
<220> FEATURE:
<221> NAME/KEY: MISC_FEATURE
<222> LOCATION: (88)..(88)
<223> OTHER INFORMATION: Xaa is Ser or Asp

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Xaa Thr Ser Thr Ala Tyr
65                  70                  75                  80

Met Glu Leu Xaa Ser Leu Arg Xaa Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 4
<211> LENGTH: 119
<212> TYPE: PRT
<213> ORGANISM: Artificial Sequence
<220> FEATURE:
<223> OTHER INFORMATION: CNTO95 heavy chain variable region (C95H22)

<400> SEQUENCE: 4

Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
```

<210> SEQ ID NO 5
<211> LENGTH: 107
<212> TYPE: PRT
<213> ORGANISM: Artificial Sequence
<220> FEATURE:
<223> OTHER INFORMATION: TIMB377 VL

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asp Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Gly His Ala Pro Ile
                85                  90                  95

Thr Phe Gly Gln Gly Thr Lys Val Glu Ile Lys
            100                 105

<210> SEQ ID NO 6
<211> LENGTH: 117
<212> TYPE: PRT
<213> ORGANISM: Artificial Sequence
<220> FEATURE:
<223> OTHER INFORMATION: S75D VRIANT OF TM3B337 VH

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial Sequence
<220> FEATURE:
<223> OTHER INFORMATION: N84D variant of TM3B337 VH

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: A88D variant of TM3B337 VH

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: PD1B244 VL

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln Gln Arg Asn Tyr Trp Pro Leu
                        85                  90                  95
Thr Phe Gly Gln Gly Thr Lys Val Glu Ile Lys
                100                 105

<210> SEQ ID NO 10
<211> LENGTH: 123
<212> TYPE: PRT
<213> ORGANISM: Artificial Sequence
<220> FEATURE:
<223> OTHER INFORMATION: S75D variant of PD1B244 VH

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Asp Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
                100                 105                 110

Trp Gly Gln Gly Thr Leu Val Thr Val Ser Ser
            115                 120

<210> SEQ ID NO 11
<211> LENGTH: 123
<212> TYPE: PRT
<213> ORGANISM: Artificial Sequence
<220> FEATURE:
<223> OTHER INFORMATION: S84D variant of PD1B244 VH

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asp Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
                100                 105                 110

Trp Gly Gln Gly Thr Leu Val Thr Val Ser Ser
            115                 120

<210> SEQ ID NO 12
<211> LENGTH: 123
```

```
<212> TYPE: PRT
<213> ORGANISM: Artificial Sequence
<220> FEATURE:
<223> OTHER INFORMATION: S88D variant of PD1B244 VH

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Asp Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 13
<211> LENGTH: 327
<212> TYPE: PRT
<213> ORGANISM: Artificial Sequence
<220> FEATURE:
<223> OTHER INFORMATION: IgG4 with S228P mutation

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210             215             220
Glu Pro Gln Val Tyr Thr Leu Pro Pro Ser Gln Glu Glu Met Thr Lys
225             230             235             240
Asn Gln Val Ser Leu Thr Cys Leu Val Lys Gly Phe Tyr Pro Ser Asp
                245             250             255
Ile Ala Val Glu Trp Glu Ser Asn Gly Gln Pro Glu Asn Asn Tyr Lys
            260             265             270
Thr Thr Pro Pro Val Leu Asp Ser Asp Gly Ser Phe Phe Leu Tyr Ser
        275             280             285
Arg Leu Thr Val Asp Lys Ser Arg Trp Gln Glu Gly Asn Val Phe Ser
    290             295             300
Cys Ser Val Met His Glu Ala Leu His Asn His Tyr Thr Gln Lys Ser
305             310             315             320
Leu Ser Leu Ser Leu Gly Lys
                325
```